US010472644B2

(12) United States Patent
Beuchat et al.

(10) Patent No.: US 10,472,644 B2
(45) Date of Patent: Nov. 12, 2019

(54) PROTEIN EXPRESSION IN PLANTS

(75) Inventors: Julien Beuchat, Saules (CH); Prisca Campanoni, Villars-Burquin (CH); Shunhong Dai, Creve Coeur, MO (US); Claudio Facchinetti, St-Blaise (CH); Nicolas Lugon-Moulin, Orbe (CH); Karen Oishi, Neuchatel (CH); Gustavo Ramirez, Venhuizen (NL); Sandrine Roesti, Grandson (CH); Helene Laparra, Neuchatel (CH); Rosa Cabrera, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 505 days.

(21) Appl. No.: 13/980,099

(22) PCT Filed: Jan. 17, 2012

(86) PCT No.: PCT/EP2012/050645

§ 371 (c)(1), (2), (4) Date: Feb. 27, 2014

(87) PCT Pub. No.: WO2012/098119

PCT Pub. Date: Jul. 26, 2012

(65) Prior Publication Data

US 2014/0296494 A1 Oct. 2, 2014

(30) Foreign Application Priority Data

Jan. 17, 2011 (EP) ..................................... 11151190

(51) Int. Cl.
*C12N 15/82* (2006.01)

(52) U.S. Cl.
CPC ..... *C12N 15/8257* (2013.01); *C12N 15/8205* (2013.01)

(58) Field of Classification Search
None
See application file for complete search history.

(56) References Cited

U.S. PATENT DOCUMENTS

| | | | | | |
|---|---|---|---|---|---|
| 5,786,464 | A | 7/1998 | Seed | | |
| 5,850,019 | A | 12/1998 | Maiti | | |
| 5,994,521 | A | 11/1999 | Maiti | | |
| 6,018,100 | A | 1/2000 | Rogers | | |
| 6,114,148 | A | 9/2000 | Seed | | |
| 6,420,547 | B1 | 7/2002 | Maiti | | |
| 6,613,961 | B1 * | 9/2003 | Ohkawa | B09C 1/105 | 424/93.7 |
| 6,930,182 | B1 | 8/2005 | Maiti | | |
| 7,737,327 | B2 | 6/2010 | Falcone | | |
| 2007/0044170 | A1 | 2/2007 | Mariolonnet | | |
| 2010/0251417 | A1 * | 9/2010 | D'Aoust | A01H 3/00 | 800/278 |
| 2010/0319094 | A1 * | 12/2010 | Maiti | C12N 15/8214 | 800/317.3 |
| 2011/0269201 | A1 * | 11/2011 | Gray | C12N 9/0006 | 435/161 |
| 2013/0198897 | A1 * | 8/2013 | Oishi | A01H 1/06 | 800/278 |
| 2013/0205448 | A1 * | 8/2013 | Carraro | C12N 15/8205 | 800/294 |

FOREIGN PATENT DOCUMENTS

| | | | | |
|---|---|---|---|---|
| CN | 101166827 A | | 4/2008 | |
| EP | 1 662 002 | | 5/2006 | |
| EP | 1 523 558 | | 7/2007 | |
| EP | 1945769 | | 2/2010 | |
| RU | 2301519 | | 6/2007 | |
| WO | WO 9317098 A1 | * | 9/1993 | C07K 14/005 |
| WO | WO-9317098 A1 | * | 9/1993 | C07K 14/005 |
| WO | WO 98/00534 | | 1/1998 | |
| WO | WO 98/05198 | | 2/1998 | |
| WO | WO 98/44097 | | 10/1998 | |
| WO | WO 98/54961 | | 12/1998 | |
| WO | WO1998054961 | * | 12/1998 | |
| WO | WO-1998054961 | * | 12/1998 | |
| WO | WO 99/48355 | | 9/1999 | |
| WO | WO 01/12828 | | 2/2001 | |
| WO | WO 01/18192 | | 3/2001 | |
| WO | WO 01/34822 | | 5/2001 | |
| WO | WO 01/38512 | | 5/2001 | |
| WO | WO 06/056483 | | 6/2006 | |

(Continued)

OTHER PUBLICATIONS

Ponti et al (An amphibian antimicrobial peptide variant expressed in Nicotiana tabacum confers resistance to phytopathogens. Biochem. J. 370:121-127, 2003).*

Matt et al (Growth of tobacco in short-day conditions leads to high starch, low sugars, altered diurnal changes in the Nia transcript and low nitrate reductase activity, and inhibition of amino acid synthesis. Planta. Dec. 1998; 207(1):27-41).*

Pogue et al (Production of pharmaceutical-grade recombinant aprotinin and a monoclonal antibody product using plant-based transient expression systems. Plant Biotechnology Journal 8, pp. 638-654, 2010. Received Sep. 2009).*

(Continued)

*Primary Examiner* — Medina A Ibrahim
*Assistant Examiner* — Wayne Zhong
(74) *Attorney, Agent, or Firm* — Mueting, Raasch & Gebhardt, P.A.

(57) ABSTRACT

The present invention relates to protein expression in plants, particularly the large-scale production of recombinant polypeptides in whole *Nicotiana tabacum* plants. The use of preselected combination of *N. tabacum* varieties and *Agrobacterium* strains, optionally including one or more improvements to the transient expression-based methods of the invention, enables the production of large quantities of a heterologous polypeptides economically and in a short period of time.

20 Claims, 8 Drawing Sheets

Specification includes a Sequence Listing.

(56) References Cited

FOREIGN PATENT DOCUMENTS

| | | | |
|---|---|---|---|
| WO | WO 06/056484 | 6/2006 | |
| WO | WO 06/119516 | 11/2006 | |
| WO | WO 2006/119516 | 11/2006 | |
| WO | WO 07/084922 | 7/2007 | |
| WO | WO 07/096192 | 8/2007 | |
| WO | WO 07/135480 | 11/2007 | |
| WO | WO 2010/038158 | 4/2010 | |
| WO | WO-2011117249 A1 * | 9/2011 | ............... A01H 1/06 |
| WO | WO 2011117249 A1 * | 9/2011 | ............... A01H 1/06 |

OTHER PUBLICATIONS

Pogue et al (Production of pharmaceutical-grade recombinant aprotinin and a monoclonal antibody product using plant-based transient expression systems. Plant Biotechnology Journal 8, pp. 638-654, 2010).*

Klement (The Hypersensitive Reaction to Infection by Bacterial Plant PA Thogens. Annual Review of Phytopathology 5: 17-44, 1967).*

Hellens et al (Transient expression vectors for functional genomics, quantification of promoter activity and RNA silencing in plants. Plant Methods, 1:13, p. 1-14, 2005).*

Park (Agrobacterium Tumefaciens-Mediated Transformation of Tobacco (*Nicotiana tabacum* L.) Leaf Disks: Evaluation of the Co-Cultivation Conditions to Increase β-Glucuronidase Gene Activity. Thesis. Aug. 2006).*

Meijer et al (Influence of Plant Position on Growth of Duckweed. Aquat. Plant Manage. 25: 28-30, 1987).*

Sheen et al (Biomass and Chemical Composition of Tobacco Plants Under High Density Growth. Beitriige zur Tabakforschung International • vol. 12 • No. 1 • Feb. 1983).*

Pe'rez-Donoso et al (Cell Wall-Degrading Enzymes Enlarge the Pore Size of Intervessel Pit Membranes in Healthy and Xylella fastidiosa-Infected Grapevines. Plant Physiology, Mar. 2010, vol. 152, pp. 1748-1759).*

Ohta et al (Construction and Expression in Tobacco of a b-Glucuronidase (GUS) Reporter Gene Containing an Intron within the Coding Sequence. Plant Cell Physiol. 31, 805-813, 1990).*

Lindbo (High-efficiency protein expression in plants from agroinfection-compatible Tobacco mosaic virus expression vectors. BMC Biotechnology, 7:52, p. 1-11, 2007).*

PCT/EP2012/050645 International Preliminary Examination Report dated Jul. 25, 2013.

Bendahamane et al., "Agrobacterium Transient Expression System as a Tool for the Isolation of Disease Resistance Genes: Application to the Rx2 Locus in Potato", *The Plant Journal*, (2000), 21(1), 73-81.

Kapila et al., "An Agrobacterium-Mediated Transient Gene Expression System for Intact Leaves", *Plant Science*, 122 (1997), 101-108.

Kongsuwan et al., "The Plasmid RK2 Replication Initiator Protein (TrfA) binds to the Sliding Clamp β Subunit of DNA Polymerase III: Implication for the Toxicity of a Peptide Derived from the Amino-Terminal Portion of 33-Kilodalton TrfA", *Journal of Bacteriology*, vol. 188, No. 15, Aug. 2006, p. 5501-5509.

Kowalczyk et al., "Positioning and the Specific Sequence of Each 13-mer Motif are Critical for Activity of the Plasmid RK2 Repliction Origin", Molecular Microbiology (2005), 57(5), pp. 1439-1449.

Potula et al., "Transient Expression, Purification and Characterization of Bioactive Human Fibroblast Growth Factor 8b in Tobacco Plants", *Transgenic Res* (2008), 17:19-32.

Rodriquez et al., "Transient Expression in Tobacco Leaves of an Aglycosylated Recombinant Antibody Against the Epidermal Growth Factor Receptor", *Biotechnology and Bioengineering*, vol. 89, No. 2, Jan. 20, 2005.

Conley et al., "Recombinant Protein Production in a Variety of Nicotiana Hosts: A Comparative Analysis", *Plant Biotechnology Journal*, vol. 9, No. 4, Oct. 7, 2010, pp. 434-444.

Cuesta Arenas Y et al., "Functional Analysis and Mode of Action of Phytotoxic Nepl-Like Proteins of Botrytis Cinerea", *Physiological and Molecular Plant Pathology*, vol. 74, No. 5-6, Sep. 1, 2010 (pp. 376-386).

Gils et al., "High-Yield Production of Authentic Human Growth Hormone Using a Plant Virus-Based Expression System", *Plant Biotechnology Journal*, vol. 3, No. 6, Nov. 1, 2005, pp. 613-620.

Grimsley, "Agroinfection", Methods in Molecular Biology, vol. 44, Agrobacterium Protocols, 1995, pp. 325-342.

Hajdukiewiez et al., "The Small, Versatile pPZP Family of Agrobacterium Binary Vectors for Plant Transformation", Plant Molecular Biology, 25, 989-994 (1994).

Huitema et al., "Differences in Intensity and Specificity of Hypersensitive Response Induction in *Nicotiana* spp. by INFI, INF2A, and INF2B of Phytophthora Infestans", *Molecular Plant-Microbe Interactions*, vol. 18, No. 3, Mar. 1, 2005 (pp. 183-193).

Joensuu et al., "Hydrophobin Fusions for High-Levl Transient Protein Expression and Purification in Nicotiana Benthamiana", *Plant Physiology*, vol. 152, No. 2, Feb. 1, 2010, pp. 622-633.

Kapila, "An Agrobacterium-Mediated Transient Gene Expression System for Intact Leaves", Plant Science, vol. 122, No. 1, Jan. 15, 1997, pp. 101-108.

Margaria et al., "The Small Genomic Segment of Tomato Spotted Wilt Virus Isolate Br 20 is Necessary But Not Sufficient to Induce Lethal Necrosis in Nictiana Benthamiana and Local Necrotic Lesions in Nicotiana tabacum cv. White Burley", *Rivista Di Patologia Vegetale*, vol. 90, No. 2, 2008, pp. 337-343.

PCT/EP2011/062180 Search Report and Written Opinion dated Aug. 23, 2011.

PCT/EP2012/050630 Search Report and Written Opinion dated Mar. 30, 2012.

PCT/EP2012/050645 Search Report and Written Opinion dated Apr. 10, 2012.

Sheludko et al., "Agrobacterium-Mediated Transient Expression as an Approach to Production of Recombinant Proteins in Plants", *Recent Patents on Biotechnology*, vol. 2, No. 3, Nov. 1, 2008, pp. 198-208.

Sheludko et al., "Comparison of Several Nicotiana Species as Hosts for High-ScaleAgrobacterium-Mediated Transient Expression", *Biotechnology and Bioengineering*, vol. 96, No. 3, Feb. 15, 2007, pp. 608-614.

Tadeusz et al., "Optimization of Agrobacterium-Mediated Transient Assays of Gene Expression in Lettuce, Tomato and *Arabidopsis*", *Plant Biotechnology Journal*, vol. 3, No. 2, Mar. 1, 2005, pp. 259-273.

Thole et al., "The pCLEAN Dual Binary Vector System for Agrobacterium-Mediated Plant Transformation", *Plant Physiology*, vol. 145, No. 4, Dec. 1, 2007, pp. 1211-1219.

Van der Hoorn et al., "Agroinfiltration is a Versatile Tool That Facilitates Comparative Analyses of Avr9/Cf-9-induced and Avr4/Cf-4-induced Necrosis", *Molecular Plant-Microbe Interactions*, vol. 13, No. 4, Apr. 1, 2000, pp. 439-446.

Van der Hoorn et al., "Identification of Distinct Specificity Determinants in Resistance Protein Cf-4 Allows Construction of a Cf-9 Mutant that Confers Recognitiion of Avirulence Protein AVR4", *The Plant Cell Online*, vol. 13, No. 2, Feb. 1, 2001, pp. 273-285.

Van Engelen et al., "pBINPLUS: An Improved Plant Transformation Vector Based on pB1N19", Transgenic Research, 4, 288-290 (1995).

Chinese Office Action for Application No. 201280009718.6 dated Sep. 22, 2014 (15 pages). English translation included.

Huitema et al., MPMI 18(3):183-193, 2005.

Official Action issued in Russian for Application No. 2013138452 dated Jul. 20, 2016 (10 pages). English translation included.

Official Action issued in Russian for Application No. 2013138452 dated Feb. 8, 2016 (11 pages). English translation included.

Ramamoorthi et al., "So You Need a Protein—A Guide to the Production of Recombinant Proteins," *The Open Veterinary Science Journal*, 2009, 3, pp. 28-34.

(56) References Cited

OTHER PUBLICATIONS

Masroori et al., "High Level Expression of Functional Recombinant Human Coagulation Factor VII in Insect Cells", *Biotechnol. Lett.*, Mar. 2010, n. 32, pp. 803-809.

* cited by examiner

B

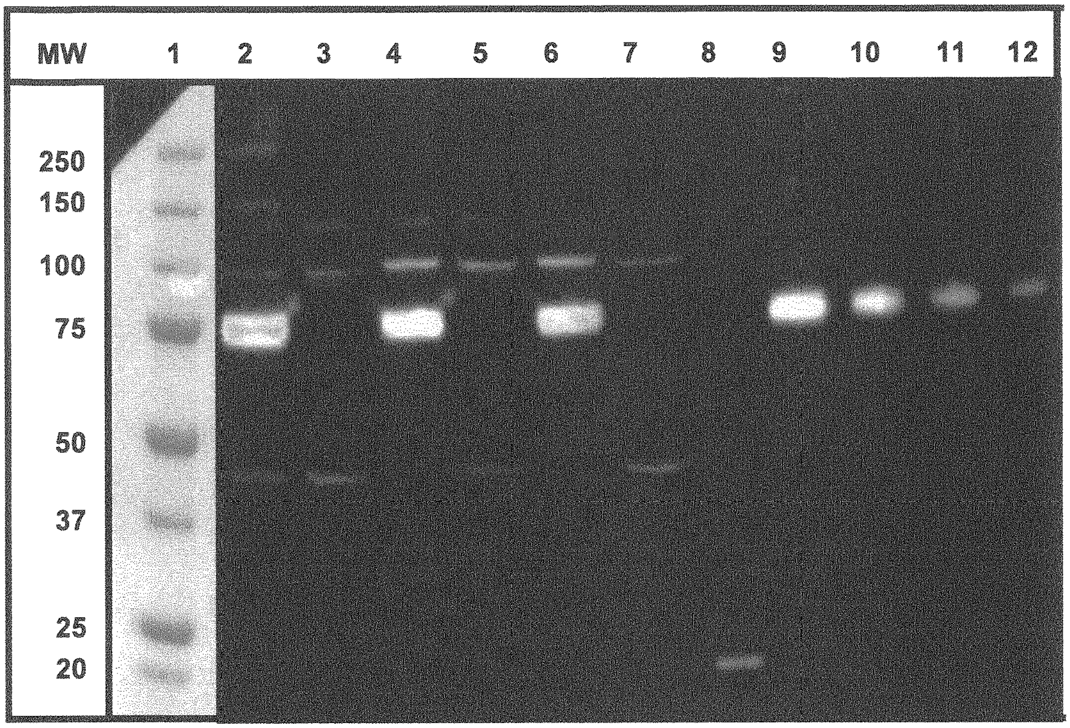

MW Molecular weight of protein ladder in kDa

1 Protein ladder under white light
2 *N. benthamiana* transiently expressing H5
3 *N. benthamiana* wild-type control
4 N. tabacum PM132 infiltrated batch 1 transiently expressing H5
5 N. tabacum PM132 wild-type control for batch 1
6 N. tabacum PM132 infiltrated batch 2 transiently expressing H5
7 N. tabacum PM132 wild-type control for batch 2
8 Protein ladder (not chemiluminescent)
9 H5 protein (plant-derived), 100 ng
10 H5 protein (plant-derived), 50 ng
11 H5 protein (plant-derived), 25 ng
12 H5 protein (plant-derived), 12.5 ng

*Figure 4*

SEQUENCE LISTING

<160> NUMBER OF SEQ ID NOS: 24

<210> SEQ ID NO 1
<211> LENGTH: 5139
<212> TYPE: DNA
<213> ORGANISM: artificial sequence
<220> FEATURE:
<223> OTHER INFORMATION: vector pPMP1

<400> SEQUENCE: 1
ctactagtcc cctagtacat taaaaacgtc cgcaatgtgt tattaagttg tctaagcgtc 60
aatttgttta caccacaata tatcctgcca ccagccagcc aacagctccc cgaccggcag 120
ctcggcacaa aatcaccact cgatacaggc agcccatcag gccttgacgg ccttccttca 180
attcgcccta tagtgagtcg tattacgtcg cgctcactgg ccgtcgtttt acaacgtcgt 240

-continued

```
gactgggaaa accctggcgt tacccaactt aatcgccttg cagcacatcc ccctttcgcc    300
agctggcgta atagcgaaga ggcccgcacc gaaacgccct tcccaacagt tgcgcagcct    360
gaatggcgaa tgggagcgcc ctgtagcggc cactcaaccc tatctcggtc tattcttttg    420
atttataagg gattttgccg atttcggcct attggttaaa aaatgagctg atttaacaaa    480
aatttaacgc gaattttaac aaaatattaa cgcttacaat ttaggtggca cttttcgggg    540
aaatgtgcgc ggaaccccta tttgtttatt tttctaaata cattcaaata tgtatccgct    600
catgagacaa taaccctgat aaatgcttca ataatattga aaaaggaaga gtatgattga    660
acaggatggc ctgcatgcgg gtagcccggc agcgtgggtg gaacgtctgt ttggctatga    720
ttgggcgcag cagaccattg gctgctctga tgcggcggtg tttcgtctga gcgcgcaggg    780
tcgtccggtg ctgtttgtga aaaccgatct gagcggtgcg ctgaacgagc tgcaggatga    840
agcggcgcgt ctgagctggc tggccaccac cggtgttccg tgtgcggcgg tgctggatgt    900
ggtgaccgaa gcgggccgtg attggctgct gctgggcgaa gtgccgggtc aggatctgct    960
gtctagccat ctggcgccgg cagaaaaagt gagcattatg gcggatgcca tgcgtcgtct   1020
gcataccctg gacccggcga cctgtccgtt tgatcatcag gcgaaacatc gtattgaacg   1080
tgcgcgtacc cgtatggaag cgggcctggt ggatcaggat gatctggatg aagaacatca   1140
gggcctggca ccggcagagc tgtttgcgcg tctgaaagcg agcatgccgg atggcgaaga   1200
tctggtggtg acccatggtg atgcgtgcct gccgaacatt atggtggaaa atggccgttt   1260
tagcggcttt attgattgcg gccgtctggg cgtggcggat cgttatcagg atattgcgct   1320
ggccacccgt gatattgcgg aagaactggg cggcgaatgg gcggatcgtt ttctggtgct   1380
gtatggcatt gcggcaccgg atagccagcg tattgcgttt tatcgtctgc tggatgaatt   1440
tttctaataa ctgtcagacc aagtttactc atatatactt tagattgatt taaaacttca   1500
tttttaattt aaaaggatct aggtgaagat cctttttgat aatctcatga ccaaaatccc   1560
ttaacgtgag ttttcgttcc actgagcgtc agaccccgta gaaaagatca aaggatcttc   1620
ttgagatcct ttttttctgc gcgtaatctg ctgcttgcaa acaaaaaaac caccgctacc   1680
agcggtggtt tgtttgccgg atcaagagct accaactctt tttccgaagg taactggctt   1740
cagcagagcg cagataccaa atactgttct tctagtgtag ccgtagttag gccaccactt   1800
caagaactct gtagcaccgc ctacatacct cgctctgcta atcctgttac cagtggctgc   1860
tgccagtggc gataagtcgt gtcttaccgg gttggactca agacgatagt taccggataa   1920
ggcgcagcgg tcgggctgaa cggggggttc gtgcacacag cccagcttgg agcgaacgac   1980
ctacaccgaa ctgagatacc tacagcgtga gctatgagaa agcgccacgc ttcccgaagg   2040
gagaaaggcg gacaggtatc cggtaagcgg cagggtcgga acaggagagc gcacgaggga   2100
gcttccaggg ggaaacgcct ggtatcttta tagtcctgtc gggtttcgcc acctctgact   2160
tgagcgtcga tttttgtgat gctcgtcagg ggggcggagc ctatggaaaa acgccagcaa   2220
cgcggccttt ttacggttcc tggccttttg ctggcctttt gctcattagg caccccaggc   2280
tttacccgaa cgaccgagcg cagcgagtca gtgagcgagg aagcggagag cgcccaatac   2340
gcaaggaaac agctatgacc atgttaatgc agctggcacg acaggtttcc cgactggaaa   2400
gcgggcagtg aaaggaaggc ccatgaggcc agttaattaa cgatcgagta ctaaatgcca   2460
gtaaagcgct ggctgctgaa cccccagccg gaactgaccc cacaaggccc tagcgtttgc   2520
aatgcaccag gtcatcattg acccaggcgt gttccaccag gccgctgcct cgcaactctt   2580
cgcaggcttc gccgacctgc tcgcgccact tcttcacgcg ggtggaatcc gatccgcaca   2640
```

-continued

```
tgaggcggaa ggtttccagc ttgagcgggt acggctcccg gtgcgagctg aaatagtcga   2700
acatccgtcg ggccgtcggc gacagcttgc ggtacttctc ccatatgaat ttcgtgtagt   2760
ggtcgccagc aaacagcacg acgatttcct cgtcgatcag gacctggcaa cgggacgttt   2820
tcttgccacg gtccaggacg cggaagcggt gcagcagcga caccgattcc aggtgcccaa   2880
cgcggtcgga cgtgaagccc atcgccgtcg cctgtaggcg cgacaggcat tcctcggcct   2940
tcgtgtaata ccggccattg atcgaccagc ccaggtcctg gcaaagctcg tagaacgtga   3000
aggtgatcgg ctcgccgata ggggtgcgct tcgcgtactc caacacctgc tgccacacca   3060
gttcgtcatc gtcggcccgc agctcgacgc cggtgtaggt gatcttcacg tccttgttga   3120
cgtggaaaat gaccttgttt tgcagcgcct cgcgcgggat tttcttgttg cgcgtggtga   3180
acagggcaga gcgggccgtg tcgtttggca tcgctcgcat cgtgtccggc cacggcgcaa   3240
tatcgaacaa ggaaagctgc atttccttga tctgctgctt cgtgtgtttc agcaacgcgg   3300
cctgcttggc ctcgctgacc tgttttgcca ggtcctcgcc ggcggttttt cgcttcttgg   3360
tcgtcatagt tcctcgcgtg tcgatggtca tcgacttcgc caaacctgcc gcctcctgtt   3420
cgagacgacg cgaacgctcc acggcggccg atggcgcggg cagggcaggg ggagccagtt   3480
gcacgctgtc gcgctcgatc ttggccgtag cttgctggac catcgagccg acggactgga   3540
aggtttcgcg gggcgcacgc atgacggtgc ggcttgcgat ggtttcggca tcctcggcgg   3600
aaaaccccgc gtcgatcagt tcttgcctgt atgccttccg gtcaaacgtc cgattcattc   3660
accctccttg cgggattgcc ccgactcacg ccggggcaat gtgcccttat tcctgatttg   3720
acccgcctgg tgccttggtg tccagataat ccaccttatc ggcaatgaag tcggtcccgt   3780
agaccgtctg gccgtccttc tcgtacttgg tattccgaat cttgccctgc acgaatacca   3840
gcgacccctt gcccaaatac ttgccgtggg cctcggcctg agagccaaaa cacttgatgc   3900
ggaagaagtc ggtgcgctcc tgcttgtcgc cggcatcgtt gcgccacata tcgattatga   3960
tagaatttac aagctataag gttattgtcc tgggtttcaa gcattagtcc atgcaagttt   4020
ttatgctttg cccattctat agatatattg ataagcgcgc tgcctatgcc ttgccccctg   4080
aaatccttac atacggcgat atcttctata taaaagatat attatcttat cagtattgtc   4140
aatatattca aggcaatctg cctcctcatc ctcttcatcc tcttcgtctt ggtagctttt   4200
taaatatggc gcttcataga gtaattctgt aaaggtccaa ttctcgtttt catacctcgg   4260
tataatctta cctatcacct caaatggttc gctgggttta tcgcccggga gggttcgaga   4320
aggggggca cccccccttcg gcgtgcgcgg tcacgcgcac agggcgcagc cctggttaaa   4380
aacaaggttt ataaatattg gtttaaaagc aggttaaaag acaggttagc ggtggccgaa   4440
aaacgggcgg aaacccttgc aaatgctgga ttttctgcct gtggacagcc cctcaaatgt   4500
caataggtgc gcccctcatc tgtcagcact ctgcccctca agtgtcaagg atcgcgcccc   4560
tcatctgtca gtagtcgcgc ccctcaagtg tcaataccgc agggcactta tccccaggct   4620
tgtccacatc atctgtggga aactcgcgta aaatcaggcg ttttcgccga tttgcgaggc   4680
tggccagctc cacgtcgccg gccgaaatcg agcctgcccc tcatctgtca acgccgcgcc   4740
gggtgagtcg gcccctcaag tgtcaacgtc cgcccctcat ctgtcagtga gggccaagtt   4800
ttccgcgagg tatccacaac gccggcggcc gcggtgtctc gcacacggct tcgacggcgt   4860
ttctggcgcg tttgcagggc catagacggc cgccagccca gcggcgaggg caaccagccc   4920
ggtgagcgtc gcaaaggcgc tcggtcttgg cgcgccaacc ctgtggttgg catgcacata   4980
```

caaatggacg aacggataaa ccttttcacg cccttttaaa tatccgatta ttctaataaa 5040
cgctcttttc tcttaggttt acccgccaat atatcctgtc aaacactgat agtttaaact 5100
gaaggcggga aacgacaatc tgcctgcagg aattgaatt 5139

<210> SEQ ID NO 2
<211> LENGTH: 314
<212> TYPE: DNA
<213> ORGANISM: artificial sequence
<220> FEATURE:
<223> OTHER INFORMATION: minimal 35S-CaMV promoter

<400> SEQUENCE: 2
gaaacctcct cggattccat tgcccagcta tctgtcactt tattgagaag atagtggaaa 60
aggaaggtgg ctcctacaaa tgccatcatt gcgataaagg aaaggccatc gttgaagatg 120
cctctgccga cagtggtccc aaagatggac ccccacccac gaggagcatc gtggaaaaag 180
aagacgttcc aaccacgtct tcaaagcaag tggattgatg tgatatctcc actgacgtaa 240
gggatgacgc acaatcccac tatccttcgc aagacccttc ctctatataa ggaagttcat 300
ttcatttgga gagg 314

<210> SEQ ID NO 3
<211> LENGTH: 517
<212> TYPE: DNA
<213> ORGANISM: artificial sequence
<220> FEATURE:
<223> OTHER INFORMATION: 5'-UTR HT-CPMV

<400> SEQUENCE: 3
tattaaaatc ttaataggtt ttgataaaag cgaacgtggg gaaacccgaa ccaaaccttc 60
ttctaaactc tctctcatct ctcttaaagc aaacttctct cttgtctttc ttgcgtgagc 120
gatcttcaac gttgtcagat cgtgcttcgg caccagtaca acgttttctt tcactgaagc 180
gaaatcaaag atctctttgt ggacacgtag tgcggcgcca ttaaataacg tgtacttgtc 240
ctattcttgt cggtgtggtc ttgggaaaag aaagcttgct ggaggctgct gttcagcccc 300
atacattact tgttacgatt ctgctgactt tcggcgggtg caatatctct acttctgctt 360
gacgaggtat tgttgcctgt acttctttct tcttcttctt gctgattggt tctataagaa 420
atctagtatt ttctttgaaa cagagttttc ccgtggtttt cgaacttgga gaaagattgt 480
taagcttctg tatattctgc ccaaatttgt cgggccc 517

<210> SEQ ID NO 4
<211> LENGTH: 188
<212> TYPE: DNA
<213> ORGANISM: artificial sequence
<220> FEATURE:
<223> OTHER INFORMATION: 3'-UTR HT-CPMV

<400> SEQUENCE: 4 atttcttta gtttgaattt actgttattc ggtgtgcatt tctatgtttg gtgagcggtt 60
ttctgtgctc agagtgtgtt tattttatgt aatttaattt ctttgtgagc tcctgtttag 120
caggtcgtcc cttcagcaag gacacaaaaa gattttaatt ttattaaaaa aaaaaaaaaa 180
agaccggg 188

<210> SEQ ID NO 5
<211> LENGTH: 2781
<212> TYPE: DNA
<213> ORGANISM: artificial sequence
<220> FEATURE:
<223> OTHER INFORMATION: P1-HcPro-P3

<400> SEQUENCE: 5

```
atggcactca tctttggcac agtcaacgct aacatcctga aggaagtgtt cggtggagct      60
cgtatggctt gcgttaccag cgcacatatg gctggagcga atggaagcat tttgaagaag     120
gcagaagaga cctctcgtgc aatcatgcac aaaccagtga tcttcggaga agactacatt     180
accgaggcag acttgcctta cacaccactc catttagagg tcgatgctga aatggagcgg     240
atgtattatc ttggtcgtcg cgcgctcacc catggcaaga gacgcaaagt ttctgtgaat     300
aacaagagga acaggagaag gaaagtggcc aaaacgtacg tggggcgtga ttccattgtt     360
gagaagattg tagtgcccca caccgagaga aaggttgata ccacagcagc agtggaagac     420
atttgcaatg aagctaccac tcaacttgtg cataatagta tgccaaagcg taagaagcag     480
aaaaacttct tgcccgccac ttcactaagt aacgtgtatg cccaaacttg gagcatagtg     540
cgcaaacgcc atatgcaggt ggagatcatt agcaagaaga gcgtccgagc gagggtcaag     600
agatttgagg gctcggtgca attgttcgca agtgtgcgtc acatgtatgg cgagaggaaa     660
agggtggact tacgtattga caactggcag caagagacac ttctagacct tgctaaaaga     720
tttaagaatg agagagtgga tcaatcgaag ctcacttttg gttcaagtgg cctagttttg     780
aggcaaggct cgtacggacc tgcgcattgg tatcgacatg gtatgttcat tgtacgcggt     840
cggtcggatg ggatgttggt ggatgctcgt gcgaaggtaa cgttcgctgt ttgtcactca     900
atgacacatt atagcgacca tcaccatcac catcacgcgt ccgacaaatc aatctctgag     960
gcattcttca taccatactc taagaaattc ttggagttga gaccagatgg aatctcccat    1020
gagtgtacaa gaggagtatc agttgagcgg tgcggtgagg tggctgcaat cctgacacaa    1080
gcactttcac cgtgtggtaa gatcacatgc aaacgttgca tggttgaaac acctgacatt    1140
gttgagggtg agtcgggagg aagtgtcacc aaccaaggta agctcctagc aatgctgaaa    1200
gaacagtatc cagatttccc aatggccgag aaactactca caaggttttt gcaacagaaa    1260
tcactagtaa atacaaattt gacagcctgc gtgagcgtca aacaactcat tggtgaccgc    1320
aaacaagctc cattcacaca cgtactggct gtcagcgaaa ttctgtttaa aggcaataaa    1380
ctaacagggg ccgatctcga agaggcaagc acacatatgc ttgaaatagc aaggttcttg    1440
aacaatcgca ctgaaaatat gcgcattggc caccttggtt ctttcagaaa taaaatctca    1500
tcgaaggccc atgtgaataa cgcactcatg tgtgataatc aacttgatca gaatgggaat    1560
tttatttggg gactaagggg tgcacacgca aagaggtttc ttaaaggatt tttcactgag    1620
attgacccaa atgaaggata cgataagtat gttatcagga aacatatcag ggtagcaga     1680
aagctagcaa ttggcaattt gataatgtca actgacttcc agacgctcag gcaacaaatt    1740
caaggcgaaa ctattgagcg taaagaaatt gggaatcact gcatttcaat gcggaatggt    1800
aattacgtgt acccatgttg ttgtgttact cttgaagatg gtaaggctca atattcggat    1860
ctaaagcatc caacgaagag acatctggtc attggcaact ctggcgattc aaagtaccta    1920
gaccttccag ttctcaatga agagaaaatg tatatagcta atgaaggtta ttgctacatg    1980
aacattttct ttgctctact agtgaatgtc aaggaagagg atgcaaagga cttcaccaag    2040
tttataaggg acacaattgt tccaaagctt ggagcgtggc caacaatgca agatgttgca    2100
actgcatgct acttactttc cattctttac ccagatgtcc tgagtgctga attacccaga    2160
attttggttg atcatgacaa caaaacaatg catgttttgg attcgtatgg gtctagaacg    2220
```

```
acaggatacc acatgttgaa aatgaacaca acatcccagc taattgaatt cgttcattca   2280

ggtttggaat ccgaaatgaa aacttacaat gttggaggga tgaaccgaga tatggtcaca   2340

caaggtgcaa ttgagatgtt gatcaagtcc atatacaaac cacatctcat gaagcagtta   2400

cttgaggagg agccatacat aattgtcctg gcaatagtct ccccttcaat tttaattgcc   2460

atgtacaact ctggaacttt tgagcaggcg ttacaaatgt ggttgccaaa tacaatgagg   2520

ttagctaacc tcgctgccat cttgtcagcc ttggcgcaaa agttaacttt ggcagacttg   2580

ttcgtccagc agcgtaattt gattaatgag tatgcgcagg taattttgga caatctgatt   2640

gacggtgtca gggttaacca ttcgctatcc ctagcaatgg aaattgttac tattaagctg   2700

gccacccaag agatggacat ggcgttgagg gaaggtggct atgctgtgac ctctgcagat   2760

cgttcaaaca tttggcaata a                                             2781
```

<210> SEQ ID NO 6
<211> LENGTH: 25
<212> TYPE: DNA
<213> ORGANISM: artificial sequence
<220> FEATURE:
<223> OTHER INFORMATION: forward primer PC201F

<400> SEQUENCE: 6

```
agaaggcctt ccgggacggc gtcag                                           25
```

<210> SEQ ID NO 7
<211> LENGTH: 23
<212> TYPE: DNA
<213> ORGANISM: artificial sequence
<220> FEATURE:
<223> OTHER INFORMATION: reverse primer PC201F

<400> SEQUENCE: 7

```
atggcgcgcc cccctcggga tca                                             23
```

<210> SEQ ID NO 8
<211> LENGTH: 1707
<212> TYPE: DNA
<213> ORGANISM: artificial sequence
<220> FEATURE:
<223> OTHER INFORMATION: Mature optimized HEI (H5)

<400> SEQUENCE: 8

```
atggagaaaa tagtgcttct tcttgcaata gtcagtcttg ttaaaagtga tcagatttgc     60

attggttacc atgcaaacaa ttcaacagag caggttgaca caatcatgga aaagaacgtt    120

actgttacac atgcccaaga catactggaa aagacacaca acgggaagct ctgcgatcta    180

gatggagtga agcctctaat tttaagagat tgtagtgtag ctggatggct cctcgggaac    240

ccaatgtgtg acgaattcat caatgtaccg gaatggtctt acatagtgga gaaggccaat    300

ccaaccaatg acctctgtta cccagggagt ttcaacgact atgaagaact gaaacaccta    360

ttgagcagaa taaaccattt tgagaaaatt caaatcatcc ccaaaagttc ttggtccgat    420

catgaagcct catcaggagt tagctcagca tgtccatacc tgggaagtcc ctcctttttt    480

agaaatgtgg tatggcttat caaaaagaac agtacatacc caacaataaa gaaaagctac    540

aataatacca accaagagga tcttttggta ctgtggggaa ttcaccatcc taatgatgcg    600

gcagagcaga caaggctata tcaaaaccca accacctata tttccattgg gacatcaaca    660

ctaaaccaga gattggtacc aaaaatagct actagatcca aagtaaacgg gcaaagtgga    720

aggatggagt tcttctggac aattttaaaa cctaatgatg caatcaactt cgagagtaat    780
```

```
ggaaatttca ttgctccaga atatgcatac aaaattgtca agaaagggga ctcagcaatt    840

atgaaaagtg aattggaata tggtaactgc aacaccaagt gtcaaactcc aatgggggcg    900

ataaactcta gtatgccatt ccacaacata caccctctca ccatcgggga atgccccaaa    960

tatgtgaaat caaacagatt agtccttgca acagggctca gaaatagccc tcaaagagag   1020

agcagaagaa aaaagagagg actatttgga gctatagcag gttttataga gggaggatgg   1080

cagggaatgg tagatggttg gtatgggtac caccatagca atgagcaggg gagtgggtac   1140

gctgcagaca aagaatccac tcaaaaggca atagatggag tcaccaataa ggtcaactca   1200

atcattgaca aaatgaacac tcagtttgag gccgttggaa gggaatttaa taacttagaa   1260

aggagaatag agaatttaaa caagaagatg gaagacgggt ttctagatgt ctggacttat   1320

aatgccgaac ttctggttct catggaaaat gagagaactc tagactttca tgactcaaat   1380

gttaagaacc tctacgacaa ggtccgacta cagcttaggg ataatgcaaa ggagctgggt   1440

aacggttgtt tcgagttcta tcacaaatgt gataatgaat gtatggaaag tataagaaac   1500

ggaacgtaca actatccgca gtattcagaa gaagcaagat taaaaagaga ggaaataagt   1560

ggggtaaaat tggaatcaat aggaacttac caaatactgt caatttattc aacagtggcg   1620

agttccctag cactggcaat catgatggct ggtctatctt tatggatgtg ctccaatgga   1680

tcgttacaat gcagaatttg catttaa                                       1707
```

<210> SEQ ID NO 9
<211> LENGTH: 378
<212> TYPE: DNA
<213> ORGANISM: artificial sequence
<220> FEATURE:
<223> OTHER INFORMATION: pMMV single enhanced between EcoR1 and Hind3 sites

<400> SEQUENCE: 9

```
gaattcgtca acttcgtcca cagacatcaa catcttatcg tcctttgaag ataagataat     60

aatgttgaag ataagagtgg gagccaccac taaaacattg ctttgtcaaa agctaaaaaa    120

gatgatgccc gacagccact tgtgtgaagc atgagaagcc ggtccctcca ctaagaaaat    180

tagtgaagca tcttccagtg gtccctccac tcacagctca atcagtgagc aacaggacga    240

aggaaatgac gtaagccatg acgtctaatc ccacaagaat ttccttatat aaggaacaca    300

aatcagaagg aagagatcaa tcgaaatcaa aatcggaatc gaaatcaaaa tcggaatcga    360

aatctctcat ctaagctt                                                  378
```

<210> SEQ ID NO 10
<211> LENGTH: 641
<212> TYPE: DNA
<213> ORGANISM: artificial sequence
<220> FEATURE:
<223> OTHER INFORMATION: pMMV double enhanced between EcoR1 and Hind3 sites

<400> SEQUENCE: 10

```
gaattcgtca acttcgtcca cagacatcaa catcttatcg tcctttgaag ataagataat     60

aatgttgaag ataagagtgg gagcccccac taaaacattg ctttgtcaaa agctaaaaaa    120

gatgatgccc gacagccact tgtgtgaagc atgagaagcc ggtccctcca ctaagaaaat    180

tagtgaagca tcttccagtg gtccctccac tcacagctca atcagtgagc aacaggacga    240

aggaaatgac gtaagccatg acgtctaatc ccaacttcgt ccacagacat caacatctta    300
```

tcgtcctttg aagataagat aataatgttg aagataagag tgggagccac cactaaaaca 360
ttgctttgtc aaaagctaaa aaagatgatg cccgacagcc acttgtgtga agcatgagaa 420
gccggtccct ccactaagaa aattagtgaa gcatcttcca gtggtccctc cactcacagc 480
tcaatcagtg agcaacagga cgaaggaaat gacgtaagcc atgacgtcta atcccacaag 540
aatttcctta tataaggaac acaaatcaga aggaagagat caatcgaaat caaaatcgga 600
atcgaaatca aaatcggaat cgaaatctct catctaagct t 641

<210> SEQ ID NO 11
<211> LENGTH: 348
<212> TYPE: DNA
<213> ORGANISM: artificial sequence
<220> FEATURE:
<223> OTHER INFORMATION: pFMV single enhanced between EcoR1 and Hind3 sites

<400> SEQUENCE: 11
gaattcgtca acatcgagca gctggcttgt ggggaccaga caaaaaagga atggtgcaga 60
attgttaggc gcacctacca aaagcatctt tgcctttatt gcaaagataa agcagattcc 120
tctagtacaa gtggggaaca aaataacgtg gaaaagagct gtcctgacag cccactcact 180
aatgcgtatg acgaacgcag tgacgaccac aaaagattgc ccgggtaatc cctctatata 240
agaaggcatt cattcccatt tgaaggatca tcagatactc aaccaatatt tctcactcta 300
agaaattaag agctttgtat tcttcaatga gggctaagac ccaagctt 348

<210> SEQ ID NO 12
<211> LENGTH: 562
<212> TYPE: DNA
<213> ORGANISM: artificial sequence
<220> FEATURE:
<223> OTHER INFORMATION: pFMV double enhanced between EcoR1 and Hind3 sites

<400> SEQUENCE: 12
gaattcgtca acatcgagca gctggcttgt ggggaccaga caaaaaagga atggtgcaga 60
attgttaggc gcacctacca aaagcatctt tgcctttatt gcaaagataa agcagattcc 120
tctagtacaa gtggggaaca aaataacgtg gaaaagagct gtcctgacag cccactcact 180
aatgcgtatg acgaacgcag tgacgaccac aaaagattgc ccaacatcga gcagctggct 240
tgtggggacc agacaaaaaa ggaatggtgc agaattgtta ggcgcaccta ccaaaagcat 300
ctttgccttt attgcaaaga taaagcagat tcctctagta caagtgggga acaaaataac 360
gtggaaaaga gctgtcctga cagcccactc actaatgcgt atgacgaacg cagtgacgac 420
cacaaaagat tgcccgggta atccctctat ataagaaggc attcattccc atttgaagga 480
tcatcagata ctcaaccaat atttctcact ctaagaaatt aagagctttg tattcttcaa 540
tgagaggcta agacccaagc tt 562

<210> SEQ ID NO 13
<211> LENGTH: 274
<212> TYPE: DNA
<213> ORGANISM: artificial sequence
<220> FEATURE:
<223> OTHER INFORMATION: pPClSV single enhanced between EcoR1 and Hind3 sites

<400> SEQUENCE: 13
gaattcaatt cgtcaacgag atcttgagcc aatcaaagag gagtgatgtt gacctaaagc 60

-continued

```
aataatggag ccatgacgta agggcttacg cccatacgaa ataattaaag gctgatgtga    120

cctgtcggtc tctcagaacc tttacttttt atatttggcg tgtattttta aatttccacg    180

gcaatgacga tgtgacctgt gcatccgctt tgcctataaa taagttttag tttgtattga    240

tcgacacgat cgagaagaca cggccataaa gctt                                274
```

<210> SEQ ID NO 14
<211> LENGTH: 452
<212> TYPE: DNA
<213> ORGANISM: artificial sequence
<220> FEATURE:
<223> OTHER INFORMATION: pPClSV double enhanced between EcoR1 and Hind3 sites

<400> SEQUENCE: 14

```
gaattcgtca acgagatctt gagccaatca aagaggagtg atgtagacct aaagcaataa     60

tggagccatg acgtaagggc ttacgcccat acgaaataat taaaggctga tgtgacctgt    120

cggtctctca gaacctttac tttttatgtt tggcgtgtat ttttaaattt ccacggcaat    180

gacgatgtga cccaacgaga tcttgagcca atcaaagagg agtgatgtag acctaaagca    240

ataatggagc catgacgtaa gggcttacgc ccatacgaaa taattaaagg ctgatgtgac    300

ctgtcggtct ctcagaacct ttacttttta tatttggcgt gtatttttaa atttccacgg    360

caatgacgat gtgacctgtg catccgcttt gcctataaat aagttttagt ttgtattgat    420

cgacacggtc gagaagacac ggccataagc tt                                  452
```

<210> SEQ ID NO 15
<211> LENGTH: 23
<212> TYPE: PRT
<213> ORGANISM: artificial sequence
<220> FEATURE:
<223> OTHER INFORMATION: amino acid sequence of the patatin signal peptide

<400> SEQUENCE: 15

```
Met Ala Thr Thr Lys Ser Phe Leu Ile Leu Phe Phe Met Ile Leu Ala
1               5                   10                  15

Thr Thr Ser Ser Thr Cys Ala
            20
```

<210> SEQ ID NO 16
<211> LENGTH: 69
<212> TYPE: DNA
<213> ORGANISM: artificial sequence
<220> FEATURE:
<223> OTHER INFORMATION: patatin tobacco non optimized sequence (slightly modified) as in C148 (in front of heavy chain)

<400> SEQUENCE: 16

```
atggccacta ctaaatcttt tttaatttta tttttatga tattagcaac tactagttca     60

acatgtgct                                                            69
```

<210> SEQ ID NO 17
<211> LENGTH: 69
<212> TYPE: DNA
<213> ORGANISM: artificial sequence
<220> FEATURE:
<223> OTHER INFORMATION: patatin tobacco optimized sequence as in C148 (in front of light chain)

<400> SEQUENCE: 17

```
atggccacta ctaagtcctt ccttatcctc ttcttcatga tccttgctac tacttcttct     60
```

acatgtgct 69

<210> SEQ ID NO 18
<211> LENGTH: 1356
<212> TYPE: DNA
<213> ORGANISM: artificial sequence
<220> FEATURE:
<223> OTHER INFORMATION: rituximab mature heavy chain (tobacco optimized) sequence as in C148

<400> SEQUENCE: 18
caagttcaac ttcaacaacc aggtgctgaa cttgttaagc ctggtgcttc tgttaagatg 60
tcttgcaagg cttctggata cactttcaca tcctacaaca tgcattgggt taagcaaact 120
ccaggacgtg gacttgaatg gattggagct atctaccctg gaaacggtga tacttcctac 180
aaccagaagt tcaagggaaa ggctactctt actgctgata agtcctcttc cactgcttac 240
atgcaacttt cttcactcac ttccgaggat tctgctgttt attactgcgc taggtccact 300
tattatggtg gagattggta cttcaatgtt tggggagctg gaactactgt tactgtgtct 360
gctgcttcta ctaagggacc atctgttttt ccacttgctc catcttctaa gtctacttcc 420
ggtggaactg ctgctcttgg atgccttgtg aaggattatt tcccagagcc agtgactgtt 480
tcttggaact ctggtgctct tacttctggt gttcacactt tcccagctgt tcttcagtca 540
tctggacttt actccctttc ttctgttgtt actgtgccat cttcttcact tggaactcag 600
acttacatct gcaacgttaa ccacaagcca tctaacacaa aagtggataa gaaggcagag 660
ccaaagtctt gtgataagac tcatacttgt ccaccatgtc cagctccaga acttcttggt 720
ggtccatctg ttttcttgtt cccaccaaag ccaaaggata ctctcatgat ctctaggact 780
ccagaagtta cttgcgttgt tgtggatgtt tctcatgagg acccagaggt taagttcaac 840
tggtacgtgg atggtgttga agttcacaac gctaagacta agccaagata ggaacagtac 900
aactctactt accgtgttgt gtctgtgctt actgttcttc accaggattg gcttaacgga 960
aaagagtaca aatgcaaggt ttccaataag gctttgccag ctccaattga aaagactatc 1020
tccaaggcaa aaggacagcc tagagagcca caggtttaca ctcttccacc atctagagat 1080
gagcttacta agaaccaggt ttcccttact tgtcttgtga agggattcta cccatctgat 1140
attgctgttg agtgggagtc aaacggacag cctgagaaca actacaagac tactccacca 1200
gtgcttgatt ctgatggttc cttcttcctc tactccaaac tcactgtgga taagtctaga 1260
tggcagcagg gaaatgtttt ctcttgctcc gttatgcatg aggctctcca taatcactac 1320
actcagaagt ccctttcttt gtctcctgga aagtga 1356

<210> SEQ ID NO 19
<211> LENGTH: 450
<212> TYPE: PRT
<213> ORGANISM: artificial sequence
<220> FEATURE:
<223> OTHER INFORMATION: amino acid sequence of rituximab mature heavy chain

<400> SEQUENCE: 19

Gln Val Gln Leu Gln Gln Pro Gly Ala Glu Leu Val Lys Pro Gly Ala
1 5 10 15

Ser Val Lys Met Ser Cys Lys Ala Ser Gly Tyr Thr Phe Thr Ser Tyr
20 25 30

Asn Met His Trp Val Lys Gln Thr Pro Gly Arg Gly Leu Glu Trp Ile
35 40 45

-continued

```
Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

-continued

<210> SEQ ID NO 20
<211> LENGTH: 642
<212> TYPE: DNA
<213> ORGANISM: artificial sequence
<220> FEATURE:
<223> OTHER INFORMATION: rituximab mature light chain (tobacco
optimized) sequence as in C148

<400> SEQUENCE: 20

```
cagattgtgc tttctcagtc tccagctatt ctttctgctt ccccaggtga aaaggttaca     60

atgacttgcc gtgcttcttc ttctgtgtcc tacattcatt ggttccaaca gaagccagga    120

tcttctccaa agccatggat ctacgctact tctaaccttg cttctggtgt tccagttagg    180

ttttctggat ctggatctgg tacttcttac tcccttacta tttctagagt ggaggctgaa    240

gatgctgcta cttactactg ccaacagtgg acttctaatc caccaacttt cggaggtgga    300

actaagcttg agatcaagag gactgttgct gctccatctg tgtttatttt cccaccatct    360

gatgagcaac ttaagtctgg aactgcttct gttgtgtgcc ttctcaacaa tttctaccca    420

agggaagcta aggttcagtg gaaagtggat aatgctctcc agtctggaaa ttctcaagag    480

tctgtgactg agcaggattc taaggattcc acttactccc tttcttctac tcttactctc    540

tccaaggctg attatgagaa gcacaaggtt tacgcttgcg aagttactca tcagggactt    600

tcttcaccag tgacaaagtc cttcaaccgt ggagagtgtt ga                       642
```

<210> SEQ ID NO 21
<211> LENGTH: 213
<212> TYPE: PRT
<213> ORGANISM: artificial sequence
<220> FEATURE:
<223> OTHER INFORMATION: amino acid sequence of rituximab mature light
chain

<400> SEQUENCE: 21

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

-continued

```
Cys Glu Val Thr His Gln Gly Leu Ser Ser Pro Val Thr Lys Ser Phe
        195                 200                 205

Asn Arg Gly Glu Cys
    210


<210> SEQ ID NO 22
<211> LENGTH: 4
<212> TYPE: PRT
<213> ORGANISM: artificial sequence
<220> FEATURE:
<223> OTHER INFORMATION: endoplasmic reticulum retention targeting
      sequence

<400> SEQUENCE: 22

Lys Asp Glu Leu
1


<210> SEQ ID NO 23
<211> LENGTH: 4
<212> TYPE: PRT
<213> ORGANISM: artificial sequence
<220> FEATURE:
<223> OTHER INFORMATION: endoplasmic reticulum retention targeting
      sequence

<400> SEQUENCE: 23

His Asp Glu Leu
1


<210> SEQ ID NO 24
<211> LENGTH: 4
<212> TYPE: PRT
<213> ORGANISM: artificial sequence
<220> FEATURE:
<223> OTHER INFORMATION: endoplasmic reticulum retention targeting
      sequence

<400> SEQUENCE: 24

Asp Asp Glu Leu
1
```

PROTEIN EXPRESSION IN PLANTS

This application is a U.S. National Stage Application of International Application No. PCT/EP2012/050645, filed Jan. 17, 2012, which was published in English on Jul. 26, 2012 as International Patent Publication WO 2012/098119 A2. International Application No. PCT/EP2012/050645 also claims priority to European Application No. 11151190.3, filed Jan. 17, 2011.

SEQUENCE LISTING

This application contains a Sequence Listing electronically submitted via EFS-Web to the United States Patent and Trademark Office as an ASCII text filed entitled "US13980099_SubstituteSequenceListing_ST25.txt" having a size of 31 kilobytes and created on Jun. 9, 2014. The information contained in the Sequence Listing is incorporated by reference herein.

The present invention relates to protein expression in plants. In particular, the present invention is directed to methods for the large-scale production of recombinant polypeptides in whole tobacco plants.

Tobacco has been used as a host plant for studying expression of heterologous protein in plants. Transient expression of various heterologous proteins using *Nicotiana benthamiana* has been described but this species, while useful as a test model in the laboratory, yields less biomass and is not amenable for the industrialization of a platform for manufacturing large quantities of a recombinant protein within a short time period. Transient gene expression in plants and plant cells has been developed primarily as a rapid means to demonstrate production of a given protein in small amounts and for testing genetic constructs. Methods to introduce a coding sequence of a protein into a plant or plant cell include, for example, particle gun delivery, vacuum infiltration, *Agrobacterium*-mediated transmission, and polyethylene glycol-mediated delivery of naked DNA into plant protoplasts.

Stable transformation has been demonstrated for many different plant species such as for example *Medicago truncatula, Brassica napus, Lactuca sativa, Zea mays, Oryza sativa* and tobacco species, including *Nicotiana tabacum. N. tabacum* is believed to be a hybrid of *Nicotiana sylvestris, Nicotiana tomentosiformis*, and possibly *Nicotiana otophora*. It is only found in cultivation, and numerous variants and cultivars are grown commercially in many different climatic and geographic regions. There are well recognized morphological variations, agronormic properties and chemical differences among the *N. tabacum* variants and cultivars. However, only limited information is available on the relationship between physical characteristics and genetic diversity of the *N. tabacum* variants and cultivars. Even less is known about the suitability of each such variants and cultivars for producing recombinant proteins. The current commercial large-scale animal cell cultures for production of recombinant proteins are built on just a few host cell lines that had each been extensively characterized. In contrast, none such information has been developed for plant cells derived from the tobacco variants, breeding lines and cultivars, and for the whole plant.

Although stable transformation of *N. tabacum* generally for production of recombinant protein has been established, transient expression of a foreign gene in *N. tabacum* plant cells has been demonstrated only in several instances. These transient expression studies in *Nicotiana tabacum* have been limited to either infiltration of plant cells comprised within young cut-off leaves or leaf discs of *N. tabacum* cv. Petit Havana (Rodriguez et al., Biotechnol. Bioeng., 2004, 89: 188-194; Potula, et al., Transgenic Res., 2008, 17: 19-32) or injection of leaves still attached to a plant by manually injecting into the abaxial air spaces of whole leaves just under the epidermal surface using a 1 ml syringe. None of these experiments disclose a technically robust and commercially meaningful system for the large-scale production of recombinant proteins that is based on whole *N. tabacum* plants.

A recent comparative analysis by Conely et al. (Plant Biotehnol J, 2010 1-11) indicates that the level of transient expression varied significantly between a small sample of different *Nicotiana* varieties tested, and that there is no correlation between the yield of transient expression and stable expression for a given variety. This study underlines the notion that for transient expression of recombinant protein, there is tremendous unpredictability in yield amongst the *N. tabacum* varieties and cultivars. The transient expression analysis reported by Conely et al. were conducted on leaves directly injected with *Agrobacterium* suspensions at a laboratory scale. Many other aspects of the transient expression method that can affect yield, especially when the method is scaled up, such as infiltration methodology, design of the expression construct, and bulk growth/agronomic conditions, are not understood.

Given that plant expression system has been considered a promising alternative to animal cell culture for the large-scale production of recombinant proteins, there is an urgent need to develop commercially viable plant-based manufacturing platforms where the variables which are important at an industrial scale, are investigated and optimized.

This unmet need is addressed and solved by the present invention by providing a method as defined by the features of independent claims. Preferred embodiments are subject of the dependent claims. The present invention provides methods that use preselected and compatible combinations of *N. tabacum* varieties and *Agrobacterium* strains for the large-scale production of heterologous polypeptides by transient expression. The results described herein below unexpectedly show that among the many *Nicotiana tabacum* varieties tested, there was no correlation between high level of heterologous polypeptide accumulation and low proteinase activity—a feature that has been noted by others as an important factor. Accordingly, many of the *N. tabacum* varieties provided in the invention have not been considered as a host for the production of heterologous proteins. The invention also provides various improvements to the methods that further enhance the overall yield of heterologous polypeptides, such as the use of a minimally-sized binary vector, the presence of viral suppressor of gene silencing in the host plant, infiltration of the whole plant, and specific bulk growth conditions and practices. The use of preselected combination of *N. tabacum* varieties and *Agrobacterium* strains, optionally including one or more of the improvements to the transient expression-based methods of the invention, enables the production of large quantities of a heterologous polypeptide economically and in a short period of time (relative to that required for transgenic plant).

The invention relates to a method for producing a protein or polypeptide, particularly a heterologous protein or polypeptide in *Nicotiana tabacum* comprising the steps of:

(i) providing a combination of a selected variety, breeding line, or cultivar of a *Nicotiana tabacum* plant and a selected strain of an *Agrobacterium* species, which variety, breeding line, or cultivar, exhibits less than 10% necrosis, less than 5% necrosis, less than 2% necrosis, less than 1% necrosis, 5 days after leaves of said variety, breeding line, or cultivar have been injected by syringe with the selected *Agrobacterium* strain at a cell density of OD600 of 0.32;

(ii) infiltrating a whole plant of the selected variety, breeding line, or cultivar of *Nicotiana tabacum* with a suspension of the selected strain of the *Agrobacterium* species at an $OD_{600}$ of between 0.1 and 4.0, said strain comprising an expressible nucleotide sequence encoding the polypeptide under control of regulatory sequences operable in plants;

(iii) incubating the infiltrated plant for a period of between 5 days and 20 days, particularly between 7 days and 15 days, but especially between 8 days and 10 days, under conditions that allow expression of the expressible nucleotide sequence in the infiltrated plant and accumulation of the heterologous polypeptide.

In one embodiment, the invention relates to a method for producing a protein or polypeptide, particularly a heterologous protein or polypeptide in *Nicotiana tabacum* comprising the steps of:

(i) providing a combination of a selected variety, breeding line, or cultivar of a *Nicotiana tabacum* plant and a selected strain of an *Agrobacterium* species, which variety, breeding line, or cultivar, exhibits less than 10% necrosis, less than 5% necrosis, less than 2% necrosis, less than 1% necrosis, 5 days after leaves of said variety, breeding line, or cultivar have been injected by a syringe with the selected *Agrobacterium* strain at a cell density of $OD_{600}$ of 0.32;

(ii) infiltrating a whole plant of the selected variety, breeding line, or cultivar of *Nicotiana tabacum* with the selected strain of the *Agrobacterium* species comprising an expressible nucleotide sequence encoding the polypeptide under control of regulatory sequences operable in plants at an $OD_{600}$ of between 0.1 and 4.0;

(iii) incubating the infiltrated plant for a period of between 5 days and 20 days, particularly between 7 days and 15 days, but especially between 8 days and 10 days, under conditions that allow expression of the nucleotide sequence in the infiltrated plant and accumulation of the heterologous polypeptide;

with the proviso that when the expressible nucleotide sequence encodes a green fluorescent protein, the accumulation of green fluorescent protein is at least 1% of the total soluble protein of the infiltrated plant or plant cells; or that the accumulation of the polypeptide is at a level which is at least 25% of that obtainable in *N. benthamiana* when the selected *Agrobacterium* strain comprising the same expressible nucleotide sequence is used as described in step ii) and step iii).

Therefore, it is preferable that the selected combination of a variety, breeding line, or cultivar of *Nicotiana tabacum* and a strain of an *Agrobacterium* species, when used in the method according to the invention and as defined herein in the any one of the preceding embodiments, is a combination, which when used according to the invention, results in the accumulation of green fluorescent protein to at least 1%, at least 2%, at least 3%, at least 4%, at least 5%, at least 10%, at least 15%, or at least 20% of the total soluble protein of the infiltrated plant, when the expressible nucleotide sequence encodes a green fluorescent protein.

It is also preferable that the selected combination of a variety, breeding line, or cultivar of *Nicotiana tabacum* and a strain of an *Agrobacterium* species, in the method according to the invention as defined herein in the any one of the preceding embodiments, results in the accumulation of a heterologous protein to a level that is at least 25%, at least 50%, at least 75%, or equal to, or that is at least 110%, at least 125%, at least 150%, at least 200%, at least 250%, at least 300%, at least 400%, or at least 500% that obtainable in *N. benthamiana* when the same expressible nucleotide sequence and the same conditions are applied. The accumulation of the heterologous protein can be expressed in terms of unit mass (such as gram) of the heterologous protein per unit mass (such as kg) of the fresh weight (FW) of leaves, that is g/kg FW.

In an alternative embodiment, the invention relates to method for producing a protein or polypeptide, particularly a heterologous protein or polypeptide, in *Nicotiana tabacum* comprising the steps of:

(i) providing a combination of a selected variety, breeding line, or cultivar of a *Nicotiana tabacum* plant and a selected strain of an *Agrobacterium* species, which variety, breeding line, or cultivar, exhibits less than 10% necrosis, less than 5% necrosis, less than 2% necrosis, less than 1% necrosis, in 5 days after leaves of said variety, breeding line, or cultivar have been injected with the selected *Agrobacterium* strain at a cell density of OD600 of 0.32;

(ii) infiltrating a whole plant of the selected variety, breeding line, or cultivar of *Nicotiana tabacum* with the selected strain of the *Agrobacterium* species comprising an expressible nucleotide sequence encoding the polypeptide under control of regulatory sequences operable in plants at an $OD_{600}$ of between 0.1 and 4.0;

(iii) incubating the infiltrated plant for a period of between 5 days and 20 days, particularly between 7 days and 15 days, but especially between 8 days and 10 days, under conditions that allow expression of the nucleotide sequence in the infiltrated plant and accumulation of the recombinant protein, with the proviso that the infiltration according to step ii) is not carried out with a method as described and claimed in EP patent application 10 16 9888.4, filed Jul. 16, 2010, particularly with a method comprising:

(i) contacting a whole plant, or a plant part with *Agrobacterium* cells in a fluid, wherein the *Agrobacterium* cells comprise an expressible construct encoding the heterologous peptide or protein;

(ii) treating the whole plant or the plant part and the *Agrobacterium* cells with one or more pressure cycle(s) whereby the *Agrobacterium* cells infiltrate the whole plant, or the plant part, and wherein at least one of the pressure cycle(s) comprises an increase in pressure relative to atmospheric pressure.

In another embodiment, the invention relates to the method according to any of the preceding embodiments, wherein the *Agrobacterium* cells comprise a binary vector, particularly a minimally-sized binary vector comprising sequence elements, which are essential for maintenance and replication of the plasmid in *Escherichia coli* and *Agrobacterium* cells, and for the transfer of the T-DNA to a tobacco plant cell, and further a T-DNA region, comprising the coding sequence of a peptide or protein that is under control of regulatory elements functional in a *Nicotiana tabacum* plant and, optionally, a plant selectable marker gene, wherein the essential sequence elements account for at least 60%, 65%, 70%, 75%, 80% of the entire minimally-sized binary vector In a specific embodiment, the invention relates to a method according to the present invention as defined in any one of the preceding embodiments, wherein a minimal binary vector is used comprising, consisting of, or consisting essentially of the following nucleic acid elements:

a) a first nucleic acid element comprising a nucleotide sequence encoding a selectable marker which is functional in *Escherichia coli* and *Agrobacterium* species;
b) a second nucleic acid element comprising a nucleotide sequence of a first origin of replication which is functional in *Escherichia*
c) a third nucleic acid element comprising a nucleotide sequence encoding a replication initiator protein;
d) a fourth nucleic acid element comprising a nucleotide sequence of a second origin of replication, which is different from the first origin of replication and which is functional in *Agrobacterium*; and
e) a fifth nucleic acid element comprising a nucleotide sequence of a T-DNA region comprising a T-DNA right border sequence and a T-DNA left border sequence of a tumour-inducing *Agrobacterium tumefaciens* plasmid or a root-inducing plasmid of *Agrobacterium rhizogenes;* wherein the above nucleic acid elements are provided on a circular polynucleotide molecule and are separated by gap nucleotide sequences which have no function in replication, maintenance or nucleic acid transfer, and wherein said gap nucleotide sequences account for less than 20%, 25%, 30%, 35%, 40%, 45%, of the total vector size. Preferably, the gap nucleotide sequences account for less than 20% of the total vector size.

In one embodiment of the invention, the vector molecule for use in a method of the invention has a total size of less than 5,900 bp, particularly of less than 5,500 bp, particularly of less than 5,200 bp, particularly of less than 5,100 bp, but especially 5139 bp.

In one embodiment, the invention relates to the method according to the present invention as defined in any one of the preceding embodiments, wherein said minimal binary vector is based on the broad host range plasmid pRK2.

In one embodiment, the invention relates to the method according to the present invention as defined in any one of the preceding embodiments, wherein said minimal binary vector has a polynucleotide sequence being at least 80%, 81%, 82%, 83%, 84%, 85%, 86%, 87%, 88%, 89%, 90%, 91%, 92%, 93%, 94%, 95%, 96%, 97%, 98% or 99%, but particularly 100% identical to the polynucleotide sequence as depicted in SEQ ID NO: 1 and wherein the nucleic acid elements (a) to (e) exhibit the same functionality as the counterpart elements provided in SEQ ID NO:1.

In a specific embodiment, the minimally sized binary vector has a sequence as shown in SEQ ID NO: 1.

In one embodiment, the invention relates to the method according to the present invention as defined in any one of the preceding embodiments, wherein the expressible nucleotide sequence encoding the polypeptide is cloned in a minimally-sized binary vector comprising sequence elements which are essential for maintenance and replication of the plasmid in *Escherichia coil* and *Agrobacterium* cells, and for the transfer of a T-DNA to a tobacco plant cell, and, optionally, a plant selectable marker gene, wherein the proportion of the essential sequence elements accounts for at least 70% of the nucleotides of the entire minimally-sized binary vector without the expressible nucleotide sequence encoding the polypeptide.

In one embodiment, the invention relates to the method according to the present invention as defined in any one of the preceding embodiments, wherein a suppressor of gene silencing is transiently expressed in said selected variety, breeding line or cultivar of a *N. tabacum* plant when the nucleotide sequence encoding the heterologous polypeptide is expressed.

In one embodiment, the invention relates to the method according to the present invention and as defined in any one of the preceding embodiments, wherein the suppressor of gene silencing is a helper-component proteinase (HcPro) of a potyvirus.

In one embodiment, the invention relates to the method according to the present invention as defined in any one of the preceding embodiments, wherein the suppressor of gene silencing is a encoded by a nucleic acid molecule comprising the nucleotide sequence set forth in SEQ ID NO: 5.

In one embodiment, the invention relates to the method according to the present invention as defined in any one of the preceding embodiments, wherein the suppressor of gene silencing, particularly a helper-component proteinase (HcPro) of a potyvirus, particularly a helper-component proteinase (HcPro) of a potyvirus of SEQ ID NO: 5, is located on a first binary vector and the heterologous polypeptide is located on a second binary vector.

In one embodiment, the invention relates to the method according to the present invention as defined in any one of the preceding embodiments, wherein the first binary vector is provided in a first *Agrobacterium* strain and the second vector is provided in a second *Agrobacterium* strain and wherein in step (ii), the ratio of cells of the first *Agrobacterium* strain comprising the first binary vector comprising the nucleotide sequence encoding a heterologous protein, to cells of the second *Agrobacterium* strain comprising the second binary vector comprising the suppressor of gene silencing, particularly a helper-component proteinase (HcPro) of a potyvirus, particularly a helper-component proteinase (HcPro) of a potyvirus of SEQ ID NO: 5, is in a range from 3:1 to 1.6:1.

In another embodiment, the invention relates to the method of any one of the preceding embodiments, wherein the regulatory sequences operable in plants controlling the expression of the heterologous polypeptide comprise a promoter, particularly one of the promoters as disclosed herein below, but particularly a HT-CPMV promoter as such, particularly a HT-CPMV promoter or combined with the minimal 35S CaMV promoter as shown in SEQ ID NO: 2.

In another embodiment, the invention relates to the method of any one of the preceding embodiments, wherein the regulatory sequences operable in plants controlling the expression of the heterologous polypeptide comprise a promoter, particularly one of the promoters as disclosed herein below, but particularly a FLt promoter or a functional fragment thereof, wherein the FLt promoter is that of MMV, FMV or PCISV, particularly FLt promoter as provided in SEQ ID NO: 9, SEQ ID NO: 10, SEQ ID NO: 11, SEQ ID NO: 12, SEQ ID NO: 13, or SEQ ID NO: 14.

In a specific embodiment, the present invention relates to a method for producing a heterologous polypeptide in *Nicotiana tabacum* comprising the steps of:

(i) providing a combination of a selected variety, breeding line, or cultivar of a *Nicotiana tabacum* plant and a selected strain of an *Agrobacterium* species, which variety, breeding line, or cultivar, exhibits less than 10% necrosis 5 days after leaves of said variety, breeding line, or cultivar have been injected by syringe with the selected *Agrobacterium* strain at a cell density of OD600 of 0.32;
(ii) infiltrating a whole plant of the selected variety, breeding line, or cultivar of *Nicotiana tabacum* with a suspension of the selected strain of the *Agrobacterium* species at an $OD_{600}$ of between 0.1 and 4.0, said strain comprising a helper-component proteinase (HcPro) of a potyvirus, particularly a helper-component proteinase (HcPro) of a potyvirus of SEQ ID NO: 5 and an expressible nucleotide sequence encoding the polypeptide, and, optionally, applying one or more pressure cycle(s) wherein at least one of the pressure cycle(s) comprises an increase in pressure relative to atmospheric pressure, (iii) incubating the infiltrated plant for a period of between 5 days and 10 days under conditions that allow expression of the expressible nucleotide sequence in the infiltrated plant and accumulation of the heterologous polypeptide.

In another specific embodiment, the invention relates to a method for producing a heterologous polypeptide in *Nicotiana tabacum* comprising the steps of:

(i) providing a combination of a selected variety, breeding line, or cultivar of a *Nicotiana tabacum* plant and a selected strain of an *Agrobacterium* species, which variety, breeding line, or cultivar, exhibits less than 10% necrosis 5 days after leaves of said variety, breeding line, or cultivar have been injected by syringe with the selected *Agrobacterium* strain at a cell density of OD600 of 0.32;

(ii) infiltrating a whole plant of the selected variety, breeding line, or cultivar of *Nicotiana tabacum* with a suspension of the selected strain of the *Agrobacterium* species at an $OD_{600}$ of between 0.1 and 4.0, said strain comprising a helper-component proteinase (HcPro) of a potyvirus, particularly a helper-component proteinase (HcPro) of a potyvirus of SEQ ID NO: 5 and an expressible nucleotide sequence encoding the polypeptide under control of a FLt promoter or a functional fragment thereof, wherein the FLt promoter is that of MMV, FMV or PCISV, particularly a FLt promoter a provided in SEQ ID NO: 9, SEQ ID NO: 10, SEQ ID NO: 11, SEQ ID NO: 12, SEQ ID NO: 13, or SEQ ID NO: 14; and, optionally, applying one or more pressure cycle(s) wherein at least one of the pressure cycle(s) comprises an increase in pressure relative to atmospheric pressure, (iii) incubating the infiltrated plant for a period of between 5 days and 10 days under conditions that allow expression of the expressible nucleotide sequence in the infiltrated plant and accumulation of the heterologous polypeptide.

Optionally, the regulatory sequences include a 5' non-translated leader sequence, a polyadenylation signal, or one or more enhancers, or a combination of the foregoing. The present invention further contemplates other regulatory sequences as known by those skilled in the art. and as disclosed herein below including a suppressor of gene silencing.

Hence, in a further embodiment, the invention relates to the method of any of the preceding embodiments, wherein the binary vector comprising the expressible nucleotide sequence encoding the protein or polypeptide, particularly the heterologous protein or polypeptide, further comprises the coding sequence of the suppressor of gene silencing operably associated with regulatory elements that operable in the tobacco plant.

In one embodiment, the invention relates to the method of the preceding embodiments, wherein said selected variety, breeding line or cultivar of a *N. tabacum* plant comprises a suppressor of gene silencing, particularly a suppressor of gene silencing of viral origin, and particularly a suppressor of gene silencing selected from the group consisting of the p19 protein of cucumber necrotic virus (CNV), the p1 protein of rice yellow mottle virus (RYMV), the p25 protein of potato virus X (PVX), the AC2 protein of African cassava mosaic virus (ACMV), the 2b protein of cucumber mosaic virus (CMV) and the helper-component proteinase (HcPro) of a potyvirus.

In a further embodiment, the invention relates to the method of any of the preceding embodiments, wherein said method comprises infiltrating said selected variety, breeding line, or cultivar with a second suspension of *Agrobacterium* cells comprising a binary vector comprising the coding sequence of the suppressor of gene silencing. The second suspension of *Agrobacterium* cells can optionally be of the same strain as the selected *Agrobacterium* strain. The first suspension and second suspension of *Agrobacterium* cells can be infiltrated in any sequence or simultaneously. The first suspension and second suspension of *Agrobacterium* cells can be mixed prior to being used to infiltrate the tobacco plant. Optionally, the first suspension and second suspension of *Agrobacterium* cells are mixed in a defined ratio of the number of cells from each suspension.

In one embodiment, the invention relates to the method according to any of the preceding embodiments, wherein a suspension of *Agrobacterium* cells is used in step (ii) for infiltration of the *Nicotiana tabacum* variety, breeding line, or cultivar with a cell density ($OD_{600}$) in the range of 0.1 to 1.0, particularly 0.3 to 0.9, particularly 0.5 to 0.8, and particularly 0.15 to 0.35.

In another embodiment, the invention relates to the method according to any of the preceding embodiments, wherein the selected *Nicotiana tabacum* variety, breeding line, or cultivar provided in step i) is a *Nicotiana tabacum* variety, breeding line, or cultivar selected from the group consisting of *N. tabacum* accession PM016, PM021, PM92, PM102, PM132, PM204, PM205, PM215, PM216 or PM217 as deposited with NCIMB, Aberdeen, Scotland, or DAC Mata Fina, PO2, BY-64, AS44, RG17, RG8, HB04P, Basma Xanthi BX 2A, Coker 319, Hicks, McNair 944 (MN 944), Burley 21, K149, Yaka JB 125/3, Kasturi Mawar, NC 297, Coker 371 Gold, PO2, Wisliça, Simmaba, Turkish Samsun, AA37-1, B13P, F4 from the cross BU21 x Hoja Parado line 97, Samsun NN, Izmir, Xanthi NN, Karabalgar, Denizli and PO1.

In one embodiment, the invention relates to the method according to any of the preceding embodiments, wherein the selected *Nicotiana tabacum* plant variety, breeding line, or cultivar provided in step i) is one of any *Nicotiana tabacum* line PM016, the seeds of which were deposited on 6 Jan. 2011 at NCIMB Ltd, (an International Depositary Authority under the Budapest Treaty, located at Ferguson Building, Craibstone Estate, Bucksburn, Aberdeen, AB21 9YA, United Kingdom) under accession number NCIMB 41798; PM021, the seeds of which were deposited on 6 Jan. 2011 at NCIMB Ltd. under accession number NCIMB 41799; PM092, the seeds of which were deposited on 6 Jan. 2011 at NCIMB Ltd. under accession number NCIMB 41800; PM102, the seeds of which were deposited on 6 Jan. 2011 at NCIMB Ltd. under accession number NCIMB 41801; PM132, the seeds of which were deposited on 6 Jan. 2011 at NCIMB Ltd. under accession number NCIMB 41802; PM204, the seeds of which were deposited on 6 Jan. 2011 at NCIMB Ltd. under accession number NCIMB 41803; PM205, the seeds of which were deposited on 6 Jan. 2011 at NCIMB Ltd. under accession number NCIMB 41804; PM215, the seeds of which were deposited on 6 Jan. 2011 at NCIMB Ltd. under accession number NCIMB 41805;

PM216, deposited under accession number NCIMB 41806; and PM217, the seeds of which were deposited on 6 Jan. 2011 at NCIMB Ltd. under accession number NCIMB 41807.

In one embodiment, the invention relates to the method according to any of the preceding embodiments, wherein the selected *Agrobacterium* strain provided in step i) is a strain of *Agrobacterium tumefaciens* selected from the group consisting of AGL1, EHA105, GV2260, GV3101 and Chry5.

In one embodiment, the invention relates to the method according to any of the preceding embodiments, wherein the selected *Agrobacterium* strain provided in step i) is *Agrobacterium* strain AGL1 or EHA105.

In one embodiment, the invention relates to the method according to any of the preceding embodiments, wherein the combination of selected *Nicotiana tabacum* variety, breeding line, or cultivar and selected *Agrobacterium* strain provided in step i) is a combination selected from the group consisting of *Nicotiana tabacum* line PM132 with *Agrobacterium tumefaciens* strain AGL1 and *Nicotiana tabacum* line PM132 with *Agrobacterium tumefaciens* strain EHA105.

In one embodiment, the invention relates to the method according to any of the preceding embodiments, wherein the combination of selected *Nicotiana tabacum* variety, breeding line, or cultivar and selected *Agrobacterium tumefaciens* strain provided in step i) is a combination selected from the group consisting of *Nicotiana tabacum* line PM132 with *Agrobacterium tumefaciens* strain AGL1 and *Nicotiana tabacum* line PM204 with *Agrobacterium tumefaciens* strain AGL1.

In one embodiment, the invention relates to the method according to any of the preceding embodiments, wherein said *Agrobacterium tumefaciens* strain further comprises the expressible nucleotide sequence of helper-component proteinase (HcPro) of a potyvirus.

In one embodiment, the invention relates to a method for producing a protein or polypeptide, particularly a heterologous protein or polypeptide in a plant, particularly a plant of the genus *Nictotiana*, particularly a *Nicotiana tabacum* plant comprising the steps of:

infiltrating a whole plant of a selected variety, breeding line, or cultivar, particularly a plant of the genus *Nictotiana*, particularly a *Nicotiana tabacum* plant with an expressible nucleotide sequence encoding the polypeptide under control of regulatory sequences operable in plants, particularly with a suspension of a selected strain of an *Agrobacterium* species at an $OD_{600}$ of between 0.1 and 4.0, said strain comprising an expressible nucleotide sequence encoding the polypeptide under control of regulatory sequences operable in plants;

(iii) incubating the infiltrated plant, particularly for a period of between 5 days and 20 days, particularly between 7 days and 15 days, but especially between 8 days and 10 days, under conditions that allow expression of the expressible nucleotide sequence in the infiltrated plant and accumulation of the heterologous polypeptide.

In one embodiment, the invention relates to the method according to any of the preceding embodiments, wherein, prior to infiltration, the plants are exposed to light such that the stomatal conductance is in a range of between 70 μmol $m^{-2}$ $s^{-1}$ and 600 μmol $m^{-2}$ $s^{-}$, particularly of between 100 μmol $m^{-2}$ $s^{-1}$ and 500 μmol $m^{-2}$ $s^{-1}$, particularly of between 200 μmol $m^{-2}$ $s^{-1}$ and 300 μmol $m^{-2}$ $s^{-1}$, particularly of between 250 μmol $m^{-2}$ $s^{-1}$ and 450 μmol $m^{-2}$ $s^{-1}$.

In one embodiment, the invention relates to the method according to any of the preceding embodiments, wherein said infiltrating step comprises exposing major parts of the plant in situ including plant leaves and/or plant flowers and/or plant stem and/or plant roots, but particularly the entire plant, to a pressure that is lower than atmospheric pressure or a vacuum.

In one embodiment, the invention relates to the method according to any of the preceding embodiments, wherein said infiltrating step comprises exposing major parts of the plant in situ including plant leaves and/or plant flowers and/or plant stem and/or plant roots, but particularly the entire plant, to a pressure that is higher than atmospheric pressure.

In one embodiment, the invention relates to the method according to any of the preceding embodiments, wherein step iii) comprises incubating the plant under daylight conditions for seven to nine hours per day, preferably eight hours per day. The method is particularly useful for improving the level of transient expression of the heterologous protein.

In one embodiment, the invention relates to the method according to any of the preceding embodiments, wherein step iii) comprises incubating said infiltrated plant in an up-right position or, in the alternative, in an inverted position.

In one embodiment, the invention relates to the method according to any of the preceding embodiments, wherein said heterologous polypeptide is an influenza haemagglutinin or an immunogenic fragment thereof.

In one embodiment, the invention relates to the method according to any of the preceding embodiments, wherein said method further comprises incubating the whole infiltrated plant in an inverted position, or under daylight conditions for seven to nine hours per day, or both.

In one embodiment, the invention relates to the method according to any of the preceding embodiments, said method further comprising (a) prior to infiltration, growing whole plant, particularly whole plant of the genus *Nicotiana*, particularly a tobacco plant of the selected *N. tabacum* variety, breeding line, or cultivar at a density of at least 100 plants per square meter, particularly at a density of between 200 and 600 plants per square meter, particularly at a density of between 400 and 550 plants per square meter, or (b) after infiltration, incubating the infiltrated whole plants at a density of at least 100 plants per square meter, particularly at a density of between 200 and 600 plants per square meter, particularly at a density of between 400 and 550 plants per square meter, or (c) prior to infiltration, growing whole plant, particularly whole plant of the genus *Nicotiana*, particularly whole tobacco plant of the selected *N. tabacum* variety, breeding line, or cultivar at a density of at least 100 plants per square meter, particularly at a density of between 200 and 600 plants per square meter, particularly at a density of between 400 and 550 plants per square meter, and after infiltration, incubating the infiltrated whole plants at a density of at least 100 plants per square meter, particularly at a density of between 200 and 600 plants per square meter, particularly at a density of between 400 and 550 plants per square meter.

In a specific embodiment, the method according to any of the preceding embodiments comprises (a) prior to infiltration, growing whole plant, particularly whole plant of the genus *Nicotiana*, particularly whole tobacco plant of the selected *N. tabacum* variety, breeding line, or cultivar at a density of at least 100 plants per square meter, particularly at a density of between 200 and 600 plants per square meter, particularly at a density of between 400 and 550 plants per square meter, and (b) infiltrating said plants when they have reached a height of between 30 cm and 50 cm, particularly of between 35 cm and 45 cm.

In one embodiment, the invention relates to the method according to any of the preceding embodiments, wherein the infiltrated plants, particularly infiltrated plants of the genus *Nicotiana*, particularly the *Agrobacterium* infiltrated tobacco plants are infiltrated with an aqueous enzyme solution comprising one or more enzymes that degrade or digest plant cell wall to aid the extraction and purification of the heterologous protein. In particular, the enzyme solution comprises one or more enzymes selected from the group consisting of cellulases, hemicellulases, xylanases, pectinases and polygalacturonases. Cellulases that can be used include endoglucanases (E.C. 3.2.1.4), cellobiohydrolases (also called exoglucanase, E.C. 3.2.1.91), or β-glucosidases. (also called cellobiase, E.C. 3.2.1.21). After infiltration with the enzymes, the plants may be incubated for a period of time ranging from at least 1, 2, 5, 10, 12, 18, to 24 hours.

In yet another embodiment, the invention provides a composition comprising an influenza haemagglutinin 5 polypeptide (H5), particularly an influenza haemagglutinin 5 polypeptide (H5) as shown in SEQ ID NO: 8, produced in a plant, particularly a plant of the genus *Nicotiana*, particularly a tobacco plant of a selected *N. tabacum* variety, breeding line, or cultivar by a method according to any of the preceding embodiments.

In yet another embodiment, the invention provides a system for producing a heterologous polypeptide in a whole a plant, particularly a whole plant of the genus *Nicotiana*, particularly a whole tobacco plant of a selected *N. tabacum* variety, breeding line, or cultivar according to any of the preceding embodiments, an expressible nucleotide sequence encoding the polypeptide under control of regulatory sequences operable in plants, particularly a suspension comprising cells of the strain of *Agrobacterium* species comprising an expressible nucleotide sequence encoding the polypeptide under control of regulatory sequences operable in plants according to any of the preceding embodiments, a means for infiltrating whole plants, particularly with *Agrobacterium* cells, and optionally a greenhouse for incubation of the infiltrated plant that is adapted to support (a) incubating the infiltrated plant in an inverted position with illumination from above for seven to nine hours per day, (b) growing or incubating the whole plant at a density of at least 75 plants per square meter or (c) both.

In one embodiment, the invention relates to the method according to any of the preceding embodiments, wherein said heterologous polypeptide is a growth factor, receptor, ligand, signaling molecule; kinase, enzyme, hormone, tumor suppressor, blood clotting protein, cell cycle protein, metabolic protein, neuronal protein, cardiac protein, protein deficient in specific disease states, antibodies, antigens, proteins that provide resistance to diseases, proteins for replacement therapy of human genetic diseases, antimicrobial proteins, interferons, and cytokines. Examples include but is not limited to viral antigens, such as influenza haemagglutinin.

In another aspect of the invention, a general method is provided for incubating an infiltrated plant comprising an expressible nucleotide sequence encoding a polypeptide, particularly a heterologous polypeptide, said method comprising incubating the plant in an inverted position. The method is particularly useful for improving the level of transient expression of the heterologous protein. Preferably, the plant that is incubated in an inverted position is a whole plant that is infiltrated with a suspension of *Agrobacterium* cells comprising an expressible nucleotide sequence encoding a polypeptide, particularly a heterologous polypeptide. In another embodiment, the plant that is incubated in an inverted position is a transgenic plant. In certain embodiments, the invention relates to the method according to any of the preceding embodiments, wherein said incubating step comprises incubating the infiltrated plant in an inverted position. Also provided is a greenhouse that is adapted to support the incubation of infiltrated plants in an inverted position for any length of time, wherein the inverted infiltrated plants is illuminated from above.

In yet another aspect of the invention, a general method is provided for incubating an infiltrated plant comprising an expressible nucleotide sequence encoding a polypeptide, particularly a heterologous polypeptide, said method comprising incubating the plant under daylight conditions for seven to nine hours per day, preferably eight hours per day. The method is particularly useful for improving the level of transient expression of the heterologous protein. Preferably, the infiltrated plant is a whole plant that is infiltrated with a suspension of *Agrobacterium* cells comprising an expressible nucleotide sequence encoding a polypeptide, particularly a heterologous polypeptide. Preferably, the plant that is incubated in the plant in light for seven to nine hours per day, preferably eight hours per day. In certain embodiments, the invention relates to the method according to any of the preceding embodiments, wherein said incubating step comprises incubating the infiltrated plant in an inverted position.

In yet another aspect of the invention, a general method is provided for incubating a plurality of infiltrated plants within a defined area, wherein the number of infiltrated plants per unit area is higher than the average that is used for growing transgenic plants. The method comprises incubating at least 25 to 500 infiltrated plants per square meter, or at least 50, at least 100, at least 150, at least 200, at least 300, at least 400 infiltrated plants per square meter. Preferably, the plant is a whole plant that is infiltrated with a suspension of *Agrobacterium* cells comprising an expressible nucleotide sequence encoding a polypeptide, particularly a heterologous polypeptide. The method is particularly useful for reducing the cost of producing the heterologous polypeptide. Also provided is a greenhouse that is adapted to incubate at least 25 to 500 infiltrated plants per square meter, or at least 100 infiltrated plants per square meter. In certain embodiments, the invention relates to the method according to any of the preceding embodiments, wherein said incubating step comprises incubating the infiltrated plant with other infiltrated plants in a defined area, wherein the density of infiltrated plant in the area is at least 25 to 500 infiltrated plants per square meter, or at least 100 infiltrated plants per square meter.

In one embodiment, the invention relates to a composition comprising combination of a selected variety, breeding line, or cultivar of a *Nicotiana tabacum* plant and a selected strain of an *Agrobacterium* species, which variety, breeding line, or cultivar, exhibits less than 10% necrosis 5 days after leaves of said variety, breeding line, or cultivar have been injected by syringe with the selected *Agrobacterium* strain at a cell density of OD600 of 0.32.

In one embodiment, the invention relates to a composition according to any of the preceding embodiments comprising a combination of a selected variety, breeding line, or cultivar of *Nicotiana tabacum* with a selected strain of the *Agrobacterium* species comprising an expressible nucleotide sequence encoding a polypeptide under control of regulatory sequences operable in plants at an $OD_{600}$ of between 0.1 and 4.0.

In one embodiment the *Agrobacterium* cells in said composition have a cell density ($OD_{600}$) of at least 2.1, at least 2.4, at least 2.7, at least 3.0, at least 3.3, at least 3.6, at least 3.8, at least 3.9, of at least 4.0.

In one embodiment the *Nicotiana tabacum* variety, breeding line, or cultivar in said composition is selected from the group consisting of *N. tabacum* accession PO2, AS44, Wislica, Simmaba, PM132, PM092, PM016, RG17, RG8, HB04P, Basma Xanthi BX 2A, Coker 319, Hicks, McNair 944 (MN 944), Burley 21, K149, Yaka JB 125/3, PM102, NC 297, PM021, AA37-1, B13P, F4 from the cross BU21 x Hoja Parado, line 97, Samsun, PO1, PM204, PM205, PM215, PM216 and PM217.

In one embodiment the *Nicotiana tabacum* variety, breeding line, or cultivar in said composition is selected from the group consisting of *Nicotiana tabacum* line PM016, the seeds of which were deposited on 6 Jan. 2011 at NCIMB Ltd, (an International Depositary Authority under the Budapest Treaty, located at Ferguson Building, Craibstone Estate, Bucksburn, Aberdeen, AB21 9YA, United Kingdom) under accession number NCIMB 41798; PM021, the seeds of which were deposited on 6 Jan. 2011 at NCIMB Ltd. under accession number NCIMB 41799; PM092, the seeds of which were deposited on 6 Jan. 2011 at NCIMB Ltd. under accession number NCIMB 41800; PM102, the seeds of which were deposited on 6 Jan. 2011 at NCIMB Ltd. under accession number NCIMB 41801; PM132, the seeds of which were deposited on 6 Jan. 2011 at NCIMB Ltd. under accession number NCIMB 41802; PM204, the seeds of which were deposited on 6 Jan. 2011 at NCIMB Ltd. under accession number NCIMB 41803; PM205, the seeds of which were deposited on 6 Jan. 2011 at NCIMB Ltd. under accession number NCIMB 41804; PM215, the seeds of which were deposited on 6 Jan. 2011 at NCIMB Ltd. under accession number NCIMB 41805; PM216, the seeds of which were deposited under accession number NCIMB 41806; and PM217, the seeds of which were deposited on 6 Jan. 2011 at NCIMB Ltd. under accession number NCIMB 41807

In one embodiment, the selected *Agrobacterium* strain in any of the previously described compositions is a strain of *Agrobacterium tumefaciens* selected from the group consisting of AGL1, EHA105, GV2260, GV3101 and Chry5.

In one embodiment, the selected *Agrobacterium* strain in any of the previously described compositions is *Agrobacterium* strain AGL1 or EHA105.

In one embodiment, the invention relates to a composition comprising a combination of *Nicotiana tabacum* line PM132 with *Agrobacterium tumefaciens* strain AGL1 or of *Nicotiana tabacum* line PM132 with *Agrobacterium tumefaciens* strain EHA105.

In one embodiment, the invention relates to a composition comprising a combination of *Nicotiana tabacum* line PM132 with *Agrobacterium tumefaciens* strain AGL1 or of *Nicotiana tabacum* line PM204 with *Agrobacterium tumefaciens* strain AGL1.

In one embodiment, the invention relates to a composition according to any of the preceding embodiments, wherein said *Agrobacterium* strain further comprises the expressible nucleotide sequence of helper-component proteinase (HcPro) of a potyvirus.

Definitions

Technical and scientific terms and expressions used within the scope of this application are generally to be given the meaning commonly applied to them in the pertinent art of plant biology. Reference is made herein to various methodologies known to those of skill in the art. Publications and other materials setting forth such known methodologies to which reference is made are incorporated herein by reference in their entireties as though set forth in full. The practice of the invention will employ, unless otherwise indicated, conventional techniques of chemistry, molecular biology, microbiology, genetic engineering and plant biology, which are within the skill of the art.

Any suitable materials and/or methods known to those of skill can be utilized in carrying out the present invention: however, preferred materials and/or methods are described. Materials, reagents and the like to which reference is made in the following description and examples are obtainable from commercial sources, unless otherwise noted.

All of the following term definitions apply to the complete content of this application. The word "comprising" does not exclude other elements or steps, and the indefinite article "a" or "an" does not exclude a plurality. A single step may fulfil the functions of several features recited in the claims. The terms "essentially", "about", "approximately" and the like in connection with an attribute or a value particularly also define exactly the attribute or exactly the value, respectively. The term "about" in the context of a given numerate value or range refers to a value or range that is within 20%, within 10%, or within 5% of the given value or range.

A "plant" as used within the present invention refers to any plant at any stage of its life cycle or development, and its progenies.

A "plant part" or "part of a plant" as used herein is meant to refer to any part of a plant, i.e. a plant organ, a plant tissue, a plant cell, an embryo, a leaf, etc. in planta or in culture. In certain embodiments of the invention relating to plant inoculation under high or low pressure or a combination thereof, this term refers to plant parts in planta.

A "tobacco plant" as used within the present invention refers to a plant of a species belonging to the genus *Nicotiana*, including but not limited to *Nicotiana tabacum* (or *N. tabacum*). Certain embodiments of the invention are described herein using the term "tobacco plant" without specifying *Nicotiana tabacum*, such descriptions are to be construed to have included *Nicotiana tabacum* specifically.

A "plant cell" or "tobacco plant cell" as used within the present invention refers to a structural and physiological unit of a plant, particularly a tobacco plant. The plant cell may be in form of a protoplast without a cell wall, an isolated single cell or a cultured cell, or as a part of higher organized unit such as but not limited to, plant tissue, a plant organ, or a whole plant.

"Plant material" as used within the present invention refers to any solid, liquid or gaseous composition, or a combination thereof, obtainable from a plant, including leaves, stems, roots, flowers or flower parts, fruits, pollen, egg cells, zygotes, seeds, cuttings, secretions, extracts, cell or tissue cultures, or any other parts or products of a plant.

"Plant tissue" as used herein means a group of plant cells organized into a structural or functional unit. Any tissue of a plant in planta or in culture is included. This term includes, but is not limited to, whole plants, plant organs, and seeds.

A "plant organ" as used herein relates to a distinct or a differentiated part of a plant such as a root, stem, leaf, flower bud or embryo.

The term "optical density" or "OD" relates to the optical determination of absorbance of an optical element at a given wavelength (e.g. 600 nm=$OD_{600}$) measured in a spectrophotometer.

The term "polynucleotide" is used herein to refer to a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions. In addition, the polynucleotide can be composed of triple-stranded regions comprising DNA, RNA, or both. A polynucleotide can contain one or more modified bases, such as phosphothioates, and can be a peptide nucleic acid (PNA). Generally, polynucleotides provided by this invention can be assembled from isolated or cloned fragments of cDNA, genome DNA, oligonucleotides, or individual nucleotides, or a combination of the foregoing.

The term "gene sequence" as used herein refers to the nucleotide sequence of a nucleic acid molecule or polynucleotide that encodes a protein or polypeptide, particularly a heterologous protein or polypeptide or a biologically active RNA, and encompasses the nucleotide sequence of a partial coding sequence that only encodes a fragment of a heterologous protein. A gene sequence can also include sequences having a regulatory function on expression of a gene that are located upstream or downstream relative to the coding sequence as well as intron sequences of a gene.

The term "transcription regulating nucleotide sequence" or "regulatory sequences", each refer to nucleotide sequences influencing the transcription, RNA processing or stability, or translation of the associated (or functionally linked) nucleotide sequence to be transcribed. The transcription regulating nucleotide sequence may have various localizations with the respect to the nucleotide sequences to be transcribed. The transcription regulating nucleotide sequence may be located upstream (5' non-coding sequences), within, or downstream (3' non-coding sequences) of the sequence to be transcribed (e.g., a coding sequence). The transcription regulating nucleotide sequences may be selected from the group comprising enhancers, promoters, translation leader sequences, introns, 5'-untranslated sequences, 3'-untranslated sequences, and polyadenylation signal sequences. They include natural and synthetic sequences as well as sequences, which may be a combination of synthetic and natural sequences.

The term "promoter" refers to the nucleotide sequence at the 5' end of a gene that directs the initiation of transcription of the gene. Generally, promoter sequences are necessary, but not always sufficient, to drive the expression of a gene to which it is operably linked. In the design of an expressible gene construct, the gene is placed in sufficient proximity to and in a suitable orientation relative to a promoter such that the expression of the gene is controlled by the promoter sequence. The promoter is positioned preferentially upstream to the gene and at a distance from the transcription start site that approximates the distance between the promoter and the gene it controls in its natural setting. As is known in the art, some variation in this distance can be tolerated without loss of promoter function. As used herein, the term "operatively linked" means that a promoter is connected to a coding region in such a way that the transcription of that coding region is controlled and regulated by that promoter. Means for operatively linking a promoter to a coding region are well known in the art.

The term "suppressor of gene silencing" used in the context of this invention refers to virus-encoded proteins that allow certain viruses to circumvent post-transcriptional gene silencing by binding to silencing RNA's. Also transgenes when introduced in a plant cell, can trigger post-transcriptional gene silencing as the result of which low or no expression of such genes is established.

The terms "protein", "polypeptide", "peptide" or "peptide fragments" as used herein are interchangeable and are defined to mean a biomolecule composed of two or more amino acids linked by a peptide bond, which may be folded into secondary, tertiary or quaternary structure to achieve a particular morphology.

The term "heterologous" as used herein refers to a biological sequence that does not occur naturally in the context of a specific polynucleotide or polypeptide in a cell or an organism. The term "recombinant protein" or "heterologous protein" or "heterologous polypeptide", as used herein interchangeably, refers to a protein or polypeptide that is produced by a cell but does not occur naturally in the cell. For example, the recombinant or heterologous protein produced in a plant cell or whole plant can be a mammalian or human protein.

The heterologous protein that can be expressed in a modified plant cell can be an antigen (that can be, without limitation, used in a vaccine) including but not limited to a protein of a pathogen, a viral protein, a bacterial protein, a protozoal protein, a nematode protein; an enzyme, including but not limited to an enzyme (that can be, without limitation, used in treatment of a human disease or for industrial uses); a cytokine; a fragment of a cytokine receptor; a blood protein; a hormone; a fragment of a hormone receptor, a lipoprotein; an antibody or a fragment of an antibody.

The terms "antibody" and "antibodies" refer to monoclonal antibodies, multispecific antibodies, human antibodies, humanized antibodies, camelised antibodies, chimeric antibodies, single-chain Fvs (scFv), single chain antibodies, single domain antibodies, domain antibodies (VH, VHH, VLA), Fab fragments, F(ab') fragments, disulfide-linked Fvs (sdFv), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (for example, IgG, IgE, IgM, IgD, IgA and IgY), class (for example, IgG1, IgG2, IgG3, IgG4, IgA1 and IgA2) or subclass.

The term "expressible" in the context of this invention refers to an operative linkage of a gene to regulatory elements that direct the expression of the protein or polypeptide encoded by the gene in plant cells comprised within a leaf.

The term "necrosis" and necrotic response" as used herein interchangeably relates to a hypersensitive response in the tissue of a plant, particularly a tobacco plant, triggered by, for example, inoculation of the plant tissue with, for example, an *Agrobacterium* strain. Necrosis is observed when injected leaf tissue has collapsed and cells died (see Klement & Goodman, Annual Review of Phytopathology 5 (1967) 17-44). Necrosis is distinguishable by one of ordinary skill in the art from yellowing which is a condition where there is no collapse of the leaf tissue and no extensive cell death.

As used herein, a "T-DNA border" refers to a DNA fragment comprising an about 25 nucleotide long sequence capable of being recognized by the virulence gene products of an *Agrobacterium* strain, such as an *A. tumefaciens* or *A. rhizogenes* strain, or a modified or mutated form thereof, and which is sufficient for transfer of a DNA sequence to which it is linked, to eukaryotic cells, preferably plant cells. This definition includes, but is not limited to, all naturally occurring T-DNA borders from wild-type Ti plasmids, as well as any functional derivative thereof, and includes chemically synthesized T-DNA borders. In one aspect, the encoding sequence and expression control sequence of an expression construct according to the invention is located between two T-DNA borders.

The term "vacuum infiltration", as used herein, relates to a method that allows the penetration of pathogenic bacteria, e.g. *Agrobacterium*, into the intercellular or interstitial spaces. Physically, the vacuum generates a negative atmospheric pressure that causes the air spaces between the cells in the plant tissue to decrease. The longer the duration and the lower the pressure, the less air space there is within the plant tissue. A subsequent increase in the pressure allows the bacterial suspension used in the infiltration to relocate into the plant tissue, and causes the *Agrobacterium* cells to contact the plant cells inside the plant tissue.

As used herein, "level of transient expression" refers to the capacity to express at least about 250 microgram, at least about 500 microgram, at least about 750 microgram, at least about 1 mg, at least about 2 mg, at least about 3 mg, at least about 4 mg, at least about 5 mg, at least about 10 mg, at least about 15 mg, at least about 25 mg, at least about 50 mg, at least about 75 mg, at least about 100 mg, at least about 150 mg, at least about 200 mg, at least about 500 mg, at least about 1000 mg, at least about 1.5 g, at least about 2 g, at least about 2.5 g, at least about 5 g, at least about 7.5 g, at least about 10 g, at least about 15 g, or at least about 20 g per kg of plant tissue mass.

As used herein, "transient" refers to a period of time that is long enough to permit isolation of protein from a suitable plant tissue. Preferably, protein expression is at suitably high levels within at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days after introduction of the expression construct into plant tissue. In one aspect, suitably high levels are obtained within 3-7 or 5-10 days and more preferably within 3-5 or 5-7 days, after introduction of an expression construct into the plant tissue.

The present invention provides several improvements to known transient expression-based methods based on preselected combination of *N. tabacum* varieties and *Agrobacterium* strains, which enable the production of large quantities of a heterologous protein economically and in a short period of time (relative to that required for transgenic plant).

In particular, the present invention provides a method for producing a protein or polypeptide, particularly a heterologous protein or polypeptide in *Nicotiana tabacum* comprising the steps of:

(i) providing a combination of a selected variety, breeding line, or cultivar of a *Nicotiana tabacum* plant and a selected strain of an *Agrobacterium* species, which variety, breeding line, or cultivar, exhibits less than 10% necrosis in 5 days after leaves of said variety, breeding line, or cultivar have been injected by syringe with the selected *Agrobacterium* strain at a cell density of OD600 of 0.32;

(ii) infiltrating a whole plant of the selected variety, breeding line, or cultivar of *Nicotiana tabacum* with a suspension of the selected strain of the *Agrobacterium* species at an $OD_{600}$ of between 0.1 and 4.0, said strain comprising an expressible nucleotide sequence encoding the polypeptide under control of regulatory sequences operable in plants;

(iii) incubating the infiltrated plant for a period of between 5 days and 10 days under conditions that allow expression of the expressible nucleotide sequence in the infiltrated plant and accumulation of the heterologous polypeptide.

*N. tabacum* Varieties

The present invention provides preselected *Nicotiana tabacum* varieties, breeding lines, or cultivars for use as host plants in methods for producing heterologous polypeptide by transient expression. It is particularly desirable to use one of the *Nicotiana tabacum* varieties, breeding lines, or cultivars as a host plant that is to be infiltrated with a preselected *Agrobacterium* strain in order to optimize the yield of the heterologous polypeptide. *Nicotiana tabacum* varieties, breeding lines, or cultivars may be those selected from the group consisting of *N. tabacum* accession PM016, PM021, PM92, PM102, PM132, PM204, PM205, PM215, PM216 or PM217 as deposited with NCIMB, Aberdeen, Scotland, or DAC Mata Fina, PO2, BY-64, AS44, RG17, RG8, HB04P, Basma Xanthi BX 2A, Coker 319, Hicks, McNair 944 (MN 944), Burley 21, K149, Yaka JB 125/3, Kasturi Mawar, NC 297, Coker 371 Gold, PO2, Wisliça, Simmaba, Turkish Samsun, AA37-1, B13P, F4 from the cross BU21 x, Hoja Parado line 97, Samsun NN, Izmir, Xanthi NN, Karabalgar, Denizli and PO1, or any other *Nicotiana tabacum* variety breeding line, or cultivar, which exhibits less than 10% necrosis 5 days after leaves of said variety, breeding line, or cultivar have been injected by syringe with a selected *Agrobacterium* strain, particularly an *Agrobacterium* strain identified in the following paragraph, but especially *Agrobacterium* strain AGO or EHA105, at a cell density of OD600 of 0.32. In various embodiments, plants of the preselected *N. tabacum* variety that are 5 to 7 weeks old, preferably 6 weeks grown from seed, are used in the infiltrating step of the invention. Typically, such *N. tabacum* plants are of a height ranging from 40 to 60 mm, and preferably 43 to 55 mm.

*Agrobacterium* Species and Strains

The present invention provides preselected *Agrobacterium* strains for use in methods for producing heterologous polypeptide by transient expression of an expressible sequence. It is particularly advantageous to use one of the preselected *Agrobacterium* strains to infiltrate a preselected *N. tabacum* variety in order to optimize the yield of the heterologous polypeptide. In certain embodiments of the invention, the *Agrobacterium* species that may be used in method according to the invention include but are not limited to *Agrobacterium tumefaciens, Agrobacterium rhizogenes Agrobacterium radiobacter, Agrobacterium rubi, Argobacterium vitis*, but particularly *Agrobacterium tumefaciens* and *Agrobacterium rhizogenes*. In one embodiment, at least one *Agrobacterium* strain comprises *Agrobacterium tumefaciens*. The *Agrobacterium* species used can be a wild type (e.g., virulent) or a disarmed strain. Suitable strains of *Agrobacterium* include wild type strains (e.g., such as *Agrobacterium tumefaciens*) or strains in which one or more genes is mutated to increase transformation efficiency, e.g., such as *Agrobacterium* strains wherein the vir gene expression and/or induction thereof is altered due to the presence of mutant or chimeric virA or virG genes (e.g. Chen and Winans, 1991, J. Bacteriol. 173: 1139-1144; and Scheeren-Groot et al., 1994, J. Bacteriol. 176:6418-6246), *Agrobacterium* strains comprising an extra virG gene copies, such as the super virG gene derived from pTiBo542, preferably linked to a multiple-copy plasmid, as described in U.S. Pat.

No. 6,483,013, for example. Other suitable strains include, but are not limited to: *A. tumefaciens* C58C1 (Van Larebeke et al., Nature 252: 169-170 (1974)), A136 (Watson et al., J. Bacterial 123: 255-264 (1975)); LBA401 1 (Klapwijk et al., J. Bacteriol 141: 128-136 (1980)), LBA4404 (Hoekema et al., Nature 303: 179-180 (1983)); EHA101 (Hood et al., J. Bac. 168: 1291-1301 (1986)); EHA105 (Hood et al., Trans Res. 2: 208-218 (1993)); AGL1 (Lazo et al., Bio/Technology 2: 963-967 (1991)); A281 (Hood et al., supra (1986)).

In various specific embodiments of the invention, *Agrobacterium tumefaciens* strain AGL1 or EHA105 can be used in the method according to the present invention.

In certain embodiments of the invention, multiple suspensions of *Agrobacterium* cells, each expressing different genes can be used to produce the individual proteins or a heteromultimeric protein, or to enhance the level of expression of a heterologous polypeptide. In such instances, it is contemplated that the *Agrobacterium* cells in the different suspensions of *Agrobacterium* cells can be the same preselected strain or different preselected strains. Alternatively, or additionally, a single *Agrobacterium* strain may comprise a plurality of sequences comprising different genes, particularly heterologous genes. The different genes may be comprised within a single nucleic acid molecule (e.g., a single vector) or may be provided in different vectors. A non-limiting example of a second gene that can be expressed in the host plant is a gene that encodes a suppressor of silencing, of viral origin.

Necrosis Test

The invention provides a necrosis test for preselecting a *Nicotiana tabacum* variety as host plant and an *Agrobacterium* strain as a vehicle for introducing an expressible nucleotide sequence encoding a heterologous polypeptide into the cells of the host plant, wherein such a preselected combination produces efficiently a significant quantity of the heterologous polypeptide. Without being bound by the following, the necrosis test of the invention allows the identification of a host plant that is susceptible to infection by cells of an *Agrobacterium* strain, and yet resistant to the destruction of its tissue by the *Agrobacterium* cells, thereby surviving for a sufficient period of time, in the range of five to ten days, to allow expression of the gene encoding the heterologous polypeptide and accumulation of the heterologous polypeptide in the infected plant cells. Combinations of *N. tabacum* varieties and *Agrobacterium* strains that results in significant necrosis are expected to produce less and accumulate less heterologous polypeptide as the infected plant cells die early and rapidly, and any of the heterologous protein produced will be degraded in the dead cells or lost before harvest.

The necrosis test comprises infiltrating leaves of a six-weeks old *N. tabacum* variety by injection of a suspension of *Agrobacterium* cells at a cell density of OD600 of 0.32 with a syringe. Typically, immediately after infiltration, it is possible to see a sector of a leaf subtended by veins near the site of injection which becomes inundated with the bacterial suspension. The perimeter of the sector is marked for scoring later. The whole plant with the infiltrated leaves are incubated under normal growth conditions, and the leaves are inspected 5 days post infiltration. Necrosis is characterized by collapse of plant tissue and extensive cell death within the infiltrated sector, and can be scored by methods well known in the art (Klement & Goodman, Annual Review of Phytopathology 5 (1967) 17-44). If the infiltrated leaves exhibits less than 20%, less than 10% necrosis, less than 5% necrosis, less than 2% necrosis, or less than 1% necrosis, the *N. tabacum* variety and the *Agrobacterium* strain is a preselected combination of *N. tabacum* variety and the *Agrobacterium* strain of the invention. Methods of quantifying percentage of necrosis (% necrosis) are well known in the art, and can be determined, for example, by measuring the areas of one or more leaves that are necrotic and the total areas of the one or more leaves that had been infiltrated by *Agrobacterium* cells.

Binary Vector

Any binary vector may be used within the method of the present invention. In a preferred embodiment, a minimally-sized binary vector (also referred to as minimal binary vector) may be used in the methods of the invention. These minimally sized binary vectors are disclosed in co-pending application no EP11151187.9, filed Jan. 17, 2011, the disclosure of which in incorporated herein in its entirety. They are specifically designed to drive transient expression of the coding sequence encoding a protein or polypeptide, particularly a heterologous protein or polypeptide (which is placed within the T-DNA region) in infiltrated tobacco plants. In most embodiments, the binary vectors that can be used in the methods of the invention, do not encode viral proteins or viral functions, that facilitate the systemic spread or cell-to-cell movement of the sequence in an infiltrated plant. Details of the vector is described in the sections below.

The present application therefore provides vectors for *Agrobacterium*-mediated transformation in a method according to the invention, particularly advantageous for the expression of a nucleic acid in a plant cell, in particular for expressing a protein or polypeptide in a plant cell, plant tissue or specific compartment of a plant cell, for the production of one or more metabolites or other compounds in a plant cell, or part of a plant cell, for regulating the expression of a nucleic acid, for the identification of sequences with regulatory function in a plant cell, for the identification of gene and nucleic acid function, of either one or more exogenous or endogenous nucleic acids.

The minimally-sized binary vectors, which are provided herein are particularly advantageous since they are of minimal size, stably maintained as a high copy number in a bacterial cell, highly flexible and useful for multiple purposes and can be used for the transient expression as well as the expression of a heterologous sequence in a stable transgenic plant or plant cell.

The minimally-sized binary vector that may be used within the method of the present invention may comprise, consist of, or consist essentially of the following nucleic acid elements:

a) a first nucleic acid element comprising a nucleotide sequence encoding a selectable marker which is functional in *Escherichia coli* and *Agrobacterium* species;
b) a second nucleic acid element comprising a nucleotide sequence of a first origin of replication which is functional in *Escherichia coli;*
c) a third nucleic acid element comprising a nucleotide sequence encoding a replication initiator protein;
d) a fourth nucleic acid element comprising a nucleotide sequence of a second origin of replication, which is different from the first origin of replication and which is functional in *Agrobacterium*; and
e) a fifth nucleic acid element comprising a nucleotide sequence of a T-DNA region comprising a T-DNA right border sequence and a T-DNA left border sequence of a tumour-inducing *Agrobacterium tumefaciens* plasmid or a root-inducing plasmid of *Agrobacterium rhizogenes;* wherein the above nucleic acid elements are provided on a circular polynucleotide molecule and are separated by gap nucleotide sequences which have no function in replication, maintenance or nucleic acid transfer, and wherein said gap nucleotide sequences account for less than 20%, 25%, 30%, 35%, 40%, 45%, of the total vector size. Preferably, the gap nucleotide sequences account for less than 20% of the total vector size.

In a specific embodiment of the invention, a minimally-sized binary vector may be used in the method according to the present invention, wherein (i) the T-DNA left border sequence and the nucleotide sequence encoding a selectable marker (a) is separated by a first gap nucleotide sequence of not more than 300 bp;

(ii) the nucleotide sequence encoding a selectable marker (a) and the nucleotide sequence of a first origin of replication (b) is separated by a second gap nucleotide sequence of not more than 200 bp;

(iii) the nucleotide sequence of a first origin of replication (b) and the nucleotide sequence encoding a replication initiator protein (c) is separated by a third gap nucleotide sequence of not more than 200 bp;

(iv) the nucleotide sequence encoding a replication initiator protein (c) and the nucleotide sequence of a second origin of replication (d) is separated by a fourth gap nucleotide sequence of not more than 500 bp; and (v) the nucleotide sequence of a second origin of replication (d) and the T-DNA right border sequence is separated by a fifth gap nucleotide sequence of not more than 150 bp.

In certain embodiments of the invention, the minimally-sized binary vector for use in the method according to the present invention and as defined in any one of the preceding embodiments has a total size of less than 5,900 bp, less than 5,500 bp, less than 5,200 bp, or less than 5100 bp, but especially a total size of 5150 bp.

In another specific embodiment of the invention, a minimally-sized binary vector for use in a method according to the present invention and as defined in the preceding paragraph is provided, wherein the nucleic acid elements (a) through to (e) are arranged linearly relative to each other on the vector molecule in the order set out in the first embodiment of the invention, i.e., (a)(b)(c)(d)(e).

One skilled in the art will be readily capable of generating a minimally-sized binary vector for use in a method according to the invention and as defined in any one of the preceding embodiments comprising a backbone with a different order of the nucleic acids elements a) to e) as defined in any one of the preceding embodiments.

Accordingly, in one embodiment of the invention, the minimally-sized binary vector for use in a method according to the present invention and as defined in any one of the preceding embodiments is provided, wherein the nucleic acid element comprising a nucleotide sequence encoding a selectable marker functional in an *Escherichia coli* and *Agrobacterium* cell (a) is located proximally to the T-DNA left border sequence. In a specific embodiment, the nucleic acid element comprising a nucleotide sequence encoding a selectable marker functional in an *Escherichia coli* and *Agrobacterium* cell (a) and the T-DNA left border sequence is separated by a gap nucleotide sequence of not more than 300 bp.

In one embodiment of the invention, the minimally-sized binary vector for use in a method according to the present invention and as defined in any one of the preceding embodiments is provided, wherein the nucleic acid element comprising a nucleotide sequence encoding a selectable marker functional in an *Escherichia coli* and *Agrobacterium* cell (a) is located proximally to the T-DNA right border sequence. In a specific embodiment, the nucleic acid element comprising a nucleotide sequence encoding a selectable marker functional in an *Escherichia coli* and *Agrobacterium* cell (a) and the T-DNA right border sequence is separated by a gap nucleotide sequence of not more than 150 bp.

In one embodiment of the invention, the minimally-sized binary vector for use in a method according to the present invention and as defined in any one of the preceding embodiments is provided, wherein the nucleic acid elements comprising the nucleotide sequence of the first origin of replication (b) and the second origin of replication (d) are located proximally to the T-DNA left border sequence and the T-DNA right border sequence, respectively.

In a specific embodiment of the invention, the vector molecule according to the present invention and as defined in any one of the preceding embodiments is provided, wherein, the first origin of replication (b) and the second origin of replication (d) are not immediately adjacent to each other and at least one other functional element of the vector separates the first origin of replication (b) and the second origin of replication (d).

In a specific embodiment of the invention, the first origin of replication (b) and the second origin of replication (d) are selected from the group consisting of Col E1 ori and RK2 oriV, respectively.

In one embodiment of the invention, the minimally-sized binary vector for use in a method according to the present invention and as defined in any one of the preceding embodiments is provided, wherein the nucleic acid element comprising the nucleotide sequence of the first origin of replication (b) is located proximally to the T-DNA left border sequence and the nucleic acid element comprising the nucleotide sequence of the second origin of replication (d) is located proximally to the T-DNA right border sequence.

In one embodiment of the invention, the minimally-sized binary vector for use in a method according to the present invention and as defined in any one of the preceding embodiments is provided, wherein the nucleic acid element comprising the nucleotide sequence of the first origin of replication (b) is located proximally to the T-DNA right border sequence and the nucleic acid element comprising the nucleotide sequence of the second origin of replication (d) is located proximally to the T-DNA left border sequence.

In one embodiment of the invention, the vector molecule according to the present invention and as defined in any one of the preceding embodiments is provided, wherein the first origin of replication (b) and the second origin of replication (d) are not immediately adjacent to each other and at least one other functional element of the vector separates the first origin of replication (b) and the second origin of replication (d).

In another embodiment, the nucleic acid element comprising the nucleotide sequence of a first origin of replication (b) or second origin of replication (d) and the T-DNA left border sequence is separated by a gap nucleotide sequence of not more than 300 bp. In still another embodiment, the nucleic acid element comprising the nucleotide sequence of a first origin of replication (b) or second origin of replication (d) and the T-DNA right border sequence is separated by a gap nucleotide sequence of not more than 150 bp.

In one embodiment of the invention, the minimally-sized binary vector for use in a method according to the present invention and as defined in any one of the preceding embodiments is provided, wherein the nucleic acid elements comprising the nucleotide sequences of the first origin of replication (b) and second origin of replication (d) are adjacent to each other and located proximally to the T-DNA left border sequence. In a specific embodiment, a minimally-sized binary vector as defined in any one of the preceding embodiments is provided wherein the nucleic acid element comprising the nucleotide sequence of the first origin of replication (b) or the nucleotide sequence of the second origin of replication (d) and the T-DNA left border sequence is separated by a gap nucleotide sequence of not more than 300 bp and the nucleic acid elements comprising the nucleotide sequence of the first origin of replication (b) and the second origin of replication (d) are separated by a gap nucleotide sequence of not more than 200 bp.

In one embodiment of the invention, the minimally-sized binary vector for use in a method according to the present invention and as defined in any one of the preceding embodiments is provided, wherein the nucleic acid elements comprising the nucleotide sequences of the first origin of replication (b) and second origin of replication (d) are adjacent to each other and located proximally to the T-DNA right border sequence. In a specific embodiment of the invention, a minimally-sized binary vector as defined in any one of the preceding embodiments is provided wherein the nucleic acid element comprising the nucleotide sequence of the first origin of replication (b) or the nucleotide sequence of the second origin of replication (d) and the T-DNA right border sequence is separated by a gap nucleotide sequence of not more than 150 bp and the nucleic acid elements comprising the nucleotide sequence of the first origin of replication (b) and the second origin of replication (d) are separated by a gap nucleotide sequence of not more than 500 bp.

In one embodiment of the invention, the minimally-sized binary vector for use in a method according to the present invention and as defined in any one of the preceding embodiments is provided, wherein the nucleic acid element comprising a nucleotide sequence encoding a replication initiator protein (c) is flanked by the nucleic acid elements comprising the nucleotide sequence of the first origin of replication (b) and the nucleotide sequence of the second origin of replication (d).

In one embodiment of the invention, the minimally-sized binary vector for use in a method according to the present invention and as defined in any one of the preceding embodiments is provided, wherein the nucleic acid element comprising a nucleotide sequence encoding a selectable marker functional in an *Escherichia coli* and *Agrobacterium* cell (a) is flanked by the nucleic acid elements comprising the nucleotide sequence of the first origin of replication (b) and the nucleotide sequence of the second origin of replication (d). In a specific embodiment, the flanking nucleic acid elements comprising the nucleotide sequence of the first origin of replication (b) and the nucleotide sequence of the second origin of replication (d) are separated from the nucleic acid elements comprising the nucleotide sequence encoding a replication initiator protein (c) or the nucleic acid elements comprising the nucleotide sequence encoding a selectable marker functional in an *Escherichia coli* and *Agrobacterium* cell (a) by a gap nucleotide sequence of not more than 200 bp and 500 bp, respectively.

In one embodiment of the invention, the minimally-sized binary vector for use in a method for use in a method according to the present invention and as defined in any one of the preceding embodiments is provided, wherein the nucleic acid element (a) comprises a nucleotide sequence encoding a selectable marker functional in an *Escherichia coli* and *Agrobacterium* cell. The selectable marker may be an antibiotic resistance, particularly a resistance to an antibiotic selected from the group consisting of ampicillin, chloramphenicol, kanamycin, tetracycline, gentamycin, spectinomycin, bleomycin, phleomycin, rifampicin, streptomycin and blasticidin S.

In certain embodiments of the invention, the minimally-sized binary vector for use in a method according to the present invention and as defined in any one of the preceding embodiments is provided, wherein the nucleic acid element (b) comprises a nucleotide sequence of a first origin of replication functional in *Escherichia coli* selected from the group consisting of a ColE1 origin of replication, an origin of replication belonging to the ColE1 incompatibility group; a pMB1 origin of replication, and an origin of replication belonging to any one of the incompatibility group FI, FII, FIII, FIV, I J, N, O, P, Q, T, or W.

In a specific embodiment of the invention, the minimally-sized binary vector for use in a method according to the present invention and as defined in any one of the preceding embodiments is provided, wherein the nucleic acid element (b) comprises the nucleic acid of a ColE1 origin of replication. The ColE1 origin of replication can be obtained, for example, from a pBluescript vector (Agilent Technologies, Santa Clara, Calif., USA).

In another specific embodiment of the invention, the invention provides a minimally-sized binary vector for use in a method according to the present invention and as defined in any one of the preceding embodiments wherein the nucleic acid element (b) comprises the nucleic acid of a pMB1 origin of replication. The pMB1 origin of replication and encodes two RNA's, RNAI and RNAII and one protein known as Rom or Rop. For example, the pMB1 origin of replication can be that of a pGEM vector (Promega Corporation, Madison, Wis., USA) or a pUC vector such as, but not limited to, pUC8 (GenBank: L08959.1) and resulting in high copy number.

In one embodiment of the invention, the minimally-sized binary vector for use in a method according to the present invention and as defined in any one of the preceding embodiments is provided, wherein the nucleic acid element (c) comprises a nucleotide sequence encoding a replication initiator protein which is a RK2 TrfA replication initiator protein.

In certain embodiments of the invention, the minimally-sized binary vector for use in a method according to the present invention and as defined in any one of the preceding embodiments is provided, wherein the nucleic acid element (d) comprises a nucleotide sequence of a second origin of replication, which is different from the first origin of replication and is functional in *Agrobacterium*, and comprises a nucleotide sequence selected from the group consisting of a minimal oriV origin of replication, RK2 oriV, and an origin of replication belonging to any one of the incompatibility group FI, FII, FIII, FIV, I J, N, O, P, Q, T, or W.

In one embodiment of the invention, the vector molecule according to the present invention and as defined in any one of the preceding embodiments is provided, wherein the second nucleic acid element b) or the fourth nucleic acid element d) is the replication origin (oriV) and the third nucleic acid element c) is the TrfA replication initiator protein of the broad host range plasmid RK2, functional in both *Escherichia coli* and *Agrobacterium* spp. (Schmidhauser and Helinski (1985). J. Bacteriol. 164: 446-455).

In one embodiment of the invention, the vector molecule according to the present invention and as defined in any one of the preceding embodiments is provided, wherein the fifth nucleic acid element e) comprises two T-DNA border sequences, namely a T-DNA left border sequence and a T-DNA right border sequence.

In certain embodiments of the invention, the nucleic acid element e) comprises a T-DNA border sequence of an *Agrobacterium* spp. strain of the nopaline family, which is capable of catalyzing nopaline, nopalinic acid, leucinopine, glutaminopine or succinamopine.

In alternative embodiments of the invention, the nucleic acid element e) comprises a T-DNA border sequence of an *Agrobacterium* strain of the octopine family, which is capable of catalyzing octopine, octopinic acid, lysopine or histopine. In certain other embodiments of the invention, the nucleic acid element e) comprises a T-DNA border sequence of an *Agrobacterium* strain of the mannityl family catalyzing mannopine, mannopinic acid, agropine or agropinic acid.

In one embodiment of the invention, the minimally-sized binary vector for use in a method according to the present invention and as defined in any one of the preceding embodiments is provided, wherein the nucleic acid element (e) comprising a nucleotide sequence of a T-DNA region comprising a T-DNA right border sequence and a T-DNA left border sequence of an *Agrobacterium tumefaciens* tumour-inducing plasmid or an *Agrobacterium rhizogenes* root-inducing plasmid contains at least one unique restriction endonuclease cleavage site, particularly at least two, three, four, or five unique restriction endonuclease cleavage sites.

The restriction endonuclease cleavage site may be a cleavage site selected form the group consisting of AatII, Acc65I, AclI, AflII, AflIII, AhdI, AloI, ApaBI, ApaI, AseI, AsiSI, AvriI, BaeI, BamHI, BanII, Bbr7I, BbsI, BbvCI, BfrBI, BlpI, BmtI, BpII, BpmI, Bpu10I, BsaAI, BsaI, BsaXI, BsiWI, BspEI, BsrGI, BstAPI, BstBI, BstZ17I, Bsu36I, DraIII, EcoICRI, EcoNI, EcoRI, FalI, FseI, FspAI, HindIII, HpaI, KpnI, M.AclI, M.AflIII, M.AloI, M.ApaI, M.BaeI, M.BanII, M.BbvCIA, M.BbvCIB, M.BnaI, M.BsaAI, M.BstI, M.BstVI, M.DraIII, M.EcoAI, M.EcoKI, M.EcoR124I, M.HindIII, M.HpaI, M.KpnBI, M.KpnI, M.MunI, M.PaeR7I, M.PhiBssHII, M.PshAI, M.Rrh4273I, M.SacI, M.SalI, M.Sau3239I, M.SnaBI, M.Tth111I, M.VspI, M.XbaI, M.XhoI, MfeI, MluI, NheI, NruI, NsiI, PciI, PmlI, Ppu10I, PshAI, PspOMI, PsrI, RsrII, SacI, SalI, SanDI, SapI, SciI, SnaBI, SrfI, SwaI, Tth111I, XbaI, XhoI, XmnI and ZraI. Such cleavage sites can accommodate the insertion of any DNA (such as an expression cassette) that comprises a compatible 5' end, a compatible 3' end, or one or two blunt ends.

In one embodiment, said expression cassette comprises a regulatory element that is functional in a plant, particularly a plant of the genus *Nicotiana*, and a nucleotide sequence of interest.

The skilled person in the art can readily remove an endonuclease recognition site that cuts once, or more, by mutating or altering one or more basepairs of the nucleic acid comprising said recognition site without altering the properties of the vector. It will be appreciated that any such restriction endonuclease recognition site that is outside of a coding sequence, regulatory sequence or other sequence with a function essential to the vector, can be altered without affecting the properties and function of the vector. Similarly, it will be appreciated that one can mutate a sequence comprised within a fragment coding for a protein without altering the function of said protein by introducing a silent mutation. It will be appreciated that one skilled in the art might not need an unique restriction site or any restriction site or combination of sites for cloning purposes since a nucleic acid sequence for expression in a plant cell, or any other nucleic acid sequence, can also be directly incorporated into the T-DNA region of the vector or elsewhere by design and chemically synthesized together with the nucleic acid elements a) to e) of the vector molecule according to the invention and as defined in any one of the preceding embodiments without the need to use restriction endonucleases.

The invention also provides a minimally-sized binary vector for use in a method according to the invention, wherein the fifth nucleic acid element (e) further comprises, between the T-DNA right border sequence and T-DNA left border sequence, a regulatory element which is functional in a transformed plant or plant cell and that will be operably linked to a nucleotide sequence encoding a product of interest when such a nucleotide sequence is inserted in the vector molecule. Such vector molecules can be readily used for insertion of a nucleotide sequence of interest. The one or more unique restriction cleavage sites may be present between the regulatory element and one of the T-DNA border sequences to facilitate the insertion of a nucleotide sequence of interest. Accordingly, in certain embodiments the invention further provides a minimally-sized binary vector for use in a method according to the invention, wherein the fifth nucleic acid element (e) further comprises, between the T-DNA right and T-DNA left border sequences, a regulatory element which is functional in a plant cell and which is operably linked to a nucleotide sequence encoding a protein of interest.

In various embodiments of the invention, the regulatory element that is present in the T-DNA region is a promoter selected from the group consisting of cauliflower mosaic virus 35S promoter, a modified cauliflower mosaic virus 35S promoter, a double cauliflower mosaic virus 35S promoter, a minimal 35 S promoter, nopaline synthase promoter, a cowpea mosaic virus promoter, a HT-CPMV promoter, a tobacco copalyl synthase CPS2p promoter, a dihydrinin promoter, a plastocyanin promoter, a 35S/HT-CPMV promoter, and many other promoters that are derived from caulimoviruses, such as but not limited to mirabilis mosaic virus (MMV), figwort mosaic virus (FMV), peanut chlorotic streak virus (PCLSV), double CaMV 35S promoter (35Sx2), double MMV promoter (MMVx2), and double FMV promoter (FMVx2).

In certain embodiments of the invention, the nucleotide sequence under control of a plant regulatory element encodes a selectable marker which is functional in a plant cell, particularly a selectable marker selected from a group consisting of antibiotic resistance, herbicide resistance and a reporter protein or polypeptide that produces visually identifiable characteristics.

The plant selectable marker present in a binary vector to be used within the method of the present invention, particularly of a minimally-sized binary vector as described herein before, may be a marker providing resistance to an aminoglycoside antibiotic such as kanamycin or neomycin, a herbicide such as phosphinotricin or gluphosinate. In the alternative, the selectable marker may be a screenable marker such as a fluorescent protein including but not limited to green fluorescent protein (GFP).

However, for purpose of transient expression, the utility of a selectable marker for use in plant may be minimal and can be omitted from the vector. This allows a further significant reduction of the size of the vector. For example, as shown in example section 1.3, pPMP1 was constructed by deleting the pBIN61-derived neomycin phosphotransferase gene (nptII) which encodes kanamycin resistance from pC100. Thus, pPMP1 is an example of a vector of the invention that lacks a plant selectable marker.

Accordingly, in one embodiment of the present invention, the vector molecule according to the present invention and as defined in any one of the preceding embodiments is provided, wherein the plant selectable marker gene is absent or has been omitted.

As exemplified in Example 2, the present invention further provides a minimal binary vector of less than 5,150 basepairs comprising a minimal backbone and T-DNA region that without affecting replication and stable maintenance in a bacterial cell could be maintained as a high-copy plasmid in *Escherichia coli* and *Agrobacterium* spp., which can be used within a method according to the invention. The sequence of the minimal pPMP1 binary vector is provided in SEQ ID NO: 1.

Accordingly, in one embodiment, the present invention contemplates the use of a vector molecule having a polynucleotide sequence being at least 80%, 81%, 82%, 83%, 84%, 85%, 86%, 87%, 88%, 89%, 90%, 91%, 92%, 93%, 94%, 95%, 96%, 97%, 98% or 99% identical to the polynucleotide sequence as depicted in SEQ ID NO: 1 and wherein the nucleic acid elements (a) to (e) exhibit the same functionality as the counterpart elements provided in SEQ ID NO:1, in a method according to the present invention.

The vectors of the present invention and the nucleic acid elements a) to e) as defined in any one of the preceding embodiments and comprised within such vectors may either be naturally occurring nucleic acid sequences covalently linked on a circular DNA plasmid, or chemically synthesized nucleic acid sequences, or a mixture thereof. When chemically synthesized, the nucleic acid elements a) to e) can be based on naturally occurring nucleic acid and protein or polypeptide sequences of bacteria or other organisms of interest, and exhibit the same functionality as the naturally occurring sequences.

In a specific embodiment, the vector molecule has a polynucleotide sequence as depicted in SEQ ID NO: 1.

The use of pPMP1 and derivatives thereof resulted in good stable as well as transient expression of nucleic acids, proteins or peptides in transformed plant cells of *Nicotiana tabacum* and *Nicotiana benthamiana* as exemplified in the Example 10. Moreover, transformation with pPMP1 and derivatives thereof such as the minimal plant selectable binary pC100 vector, resulted preferably in single- or otherwise low-copy number integrations in the plant nuclear genome and little or no integration of vector backbone sequences.

Promoter/Enhancers/Terminators

Plant expression vectors which are functional in a plant cell and may be used within the method of the present invention in order to drive and/or control expression of a gene of interest in a tobacco plant may also contain, if desired, a promoter regulatory region (for example, one conferring inducible or constitutive, environmentally- or developmentally-regulated, or cell- or tissue-specific expression), a transcription initiation start site, a ribosome binding site, an RNA processing signal, a transcription termination site, and/or a polyadenylation signal. The regulatory elements to be used within the method of the invention may be part of an expression cassette and present in a vector molecule, particularly a binary vector, but especially a minimally sized binary vector according to any one of the preceding embodiments as described herein, operably linked to a nucleotide sequence encoding a protein of interest In various embodiments of the invention, the regulatory element is present in the T-DNA region of a binary vector, particularly a minimally sized binary vector according to any one of the preceding embodiments as described herein. Preferred promoters for use within the method according to any one of the preceding embodiments are cauliflower mosaic virus 35S promoter, a modified cauliflower mosaic virus 35S promoter, a double cauliflower mosaic virus 35S promoter, a minimal 35 S promoter, nopaline synthase promoter, a cowpea mosaic virus promoter, a HT-CPMV promoter, a tobacco copalyl synthase CPS2p promoter, a dihydrinin promoter, a plastocyanin promoter, a 35S/HT-CPMV promoter, and many other promoters that are derived from DNA viruses belonging to the Caulimoviridae family, either the full length transcript (FLt) promoters or the sub-genomic transcript promoters. Examples of such DNA viruses include, without being limited to, cauliflower mosaic virus (CaMV), mirabilis mosaic virus (MMV), figwort mosaic virus (FMV), peanut chlorotic streak virus (PCLSV).

Particularly preferred for use in a method according to any one of the preceding embodiments are the full length transcript (FLt) promoters of DNA viruses belonging to the Caulimoviridae family including but not limited to FMV promoters, such as those described in WO1998000534 and U.S. Pat. No. 5,994,521, MMV promoters such as those describe in U.S. Pat. Nos. 6,420,547 and 6,930,182 and PCISV promoters such as those described in WO1998005198, U.S. Pat. No. 5,850,019 and EP929211.

Many such promoters can be modified by linking multiple copies, for example two copies, of its enhancer sequence in tandem to enhance the promoter activity, such as but not limited to double CaMV 35S promoter (35Sx2), double MMV promoter (MMVx2), double FMV promoter (FMVx2). Functional fragments of these promoters known or described in the cited references can be used in the vector of the invention. Specific examples of such promoters have been created and EcoRI and HindIII restriction enzyme cleavage sites have been included at the ends to facilitate cloning into the minimal vectors of the invention. Nucleotide sequences that are at least 90%. 95%, 96%, 97%, 98%, 99% or 100% identical to these sequences and that are functional in enabling expression in plants of the operably linked nucleotide sequence can also be used in the vectors of the invention.

In a specific embodiment of the invention, one or more of the following promoter sequences may be used within a vector according to the invention and as described herein in any one of the preceding embodiments:

In a specific embodiment of the invention, one or more of the following promoter sequences may be used within a vector according to the invention and as described herein in any one of the preceding embodiments:

>pMMV single enhanced between EcoR1 and Hind3 sites
(SEQ ID NO: 9)
gaattcgtcaacttcgtccacagacatcaacatcttatcgtcctttga agataagataataatgttgaagataagagtgggagccaccactaaaaca ttgctttgtcaaaagctaaaaaagatgatgcccgacagccacttgtgtg aagcatgagaagccggtccctccactaagaaaattagtgaagcatcttc cagtggtccctccactcacagctcaatcagtgagcaacaggacgaagga aatgacgtaagccatgacgtctaatcccacaagaatttccttatataag gaacacaaatcagaaggaagagatcaatcgaaatcaaaatcggaatcga aatcaaaatcggaatcgaaatctctcatctaagctt

-continued

>pMMV double enhanced between EcoR1 and Hind3 sites (SEQ ID NO: 10)

*gaattc*gtcaacttcgtccacagacatcaacatcttatcgtcctttga
agataagataataatgttgaagataagagtgggagcccccactaaaaca
ttgctttgtcaaaagctaaaaaagatgatgcccgacagccacttgtgtg
aagcatgagaagccggtccctccactaagaaaattagtgaagcatcttc
cagtggtccctccactcacagctcaatcagtgagcaacaggacgaagga
aatgacgtaagccatgacgtctaatcccaacttcgtccacagacatcaa
catcttatcgtcctttgaagataagataataatgttgaagataagagtg
ggagccaccactaaaacattgctttgtcaaaagctaaaaaagatgatgc
ccgacagccacttgtgtgaagcatgagaagccggtccctccactaagaa
aattagtgaagcatcttccagtggtccctccactcacagctcaatcagt
gagcaacaggacgaaggaaatgacgtaagccatgacgtctaatcccaca
agaatttccttatataaggaacacaaatcagaaggaagagatcaatcga
aatcaaaatcggaatcgaaatcaaaatcggaatcgaaatctctcatct
*aagctt*

>pFMV single enhanced between EcoR1 and Hind3 sites (SEQ ID NO: 11)

*gaattc*gtcaacatcgagcagctggcttgtggggaccagacaaaaaag
gaatggtgcagaattgttaggcgcacctaccaaaagcatctttgccttta
ttgcaaagataaagcagattcctctagtacaagtggggaacaaaataac
gtggaaaagagctgtcctgacagcccactcactaatgcgtatgacgaac
gcagtgacgaccacaaaagattgcccgggtaatccctctatataagaag
gcattcattcccatttgaaggatcatcagatactcaaccaatatttctc
actctaagaaattaagagctttgtattcttcaatgagggctaagaccc
*aagctt*

>pFMV double enhanced between EcoR1 and Hind3 sites (SEQ ID NO: 12)

*gaattc*gtcaacatcgagcagctggcttgtggggaccagacaaaaaag
gaatggtgcagaattgttaggcgcacctaccaaaagcatctttgccttt
attgcaaagataaagcagattcctctagtacaagtggggaacaaaataa
cgtggaaaagagctgtcctgacagcccactcactaatgcgtatgacgaa
cgcagtgacgaccacaaaagattgcccaacatcgagcagctggcttgtg
gggaccagacaaaaaaggaatggtgcagaattgttaggcgcacctacca
aaagcatctttgcctttattgcaaagataaavagattcctctagtacaa
gtggggaacaaaataacgtggaaaagagctgtcctgacagcccactcac
taatgcgtatgacgaacgcagtgacgaccacaaaagattgcccgggtaa
tccctctatataagaaggcattcattcccatttgaaggatcatcagata
ctcaaccaatatttctcactctaagaaattaagagctttgtattcttca
atgagaggctaagaccc*aagctt*

>pPCISV single enhanced between EcoR1 and Hind3 sites (SEQ ID NO: 13)

*gaattc*aattcgtcaacgagatcttgagccaatcaaagaggagtgatg
ttgacctaaagcaataatggagccatgacgtaagggcttacgcccatac
gaaataattaaaggctgatgtgacctgtcggtctctcagaacctttact
ttttatatttggcgtgtatttttaaatttccacggcaatgacgatgtga
cctgtgcatccgatttgcctataaataagttttagtttgtattgatcga
cacgatcgagaagacacggccat*aagctt*

>pPCISV double enhanced between EcoR1 and Hind3 sites (SEQ ID NO: 14)

*gaattc*gtcaacgagatcttgagccaatcaaagaggagtgatgtagac
ctaaagcaataatggagccatgacgtaagggcttacgcccatacgaaat
aattaaaggctgatgtgacctgtcggtctctcagaacctttacttttta
tgtttggcgtgtatttttaaatttccacggcaatgacgatgtgacccaa
cgagatcttgagccaatcaaagaggagtgatgtagacctaaagcaataa
tggagccatgacgtaaqggcttacgcccatacgaaataattaaaggctg
atgtgacctgtcggtctctcagaacctttactttttatatttggcgtgt
atttttaaatttccacggcaatgacgatgtgacctgtgcatccgctttg
cctataaataagttttagtttgtattgatcgacacggtcgagaagacac
ggccat*aagctt*

Two series of pC100-derived vectors were created by insertion of a FLt promoter from one of these DNA viruses from the Caulimoviridae family into the T-DNA region. FIG. 7 shows the T-DNA region of a series of nine vectors, namely pC141, pC190, pC191, pC192, pC193, pC241, pC242, pC243, and pC265. The multiple cloning site present downstream of the FLt promoter in these vectors allow the insertion of a nucleotide sequence of interest for expression in plant cells, particularly plant cells of plants of the genus *Nicotiana*, particularly *Nicotiana tabacum*. A second series of smaller vectors was created by removing the expression cassette comprising the nucleotide sequence encoding the plant selectable marker (nptII) by digesting each of the vectors in the first series with SpeI and AvrII, and recircularizating the plasmid. These vectors, namely pC277, pC278, pC279, pC280, pC281 and pC282, are particularly suitable for transient expression of a polypeptide of interest in plant cells or plants, particularly plants of the genus *Nicotiana*, particularly *Nicotiana tabacum*. Accordingly, the binary vector of the invention as described herein in any one of the preceding embodiments may comprise in its T-DNA region, one or two or more copies of a FLt promoter of a DNA virus from MMV, FMV or PCISV, (e.g., SEQ ID NO: 9, SEQ ID NO: 10, SEQ ID NO: 11, SEQ ID NO: 12, SEQ ID NO: 13, SEQ ID NO: 14) and optionally an expression cassette comprising a nucleotide sequence encoding a plant selectable marker.

In one embodiment of the invention, a vector for expressing the gene sequence of the heterologous polypeptide, particularly a binary vector, but especially the minimally-sized binary vector as described herein in any one of the preceding embodiments may comprise one or more regulatory sequences, in this instance untranslated regions derived from cowpea mosaic virus (HT-CPMV; WO 07/135,480 which is incorporated herein by reference in its entirety). Preferably, the binary vector also comprises the minimal 35S CaMV promoter. The HT-CPMV system is based on a minimal promoter, a modified 5'-UTR, containing hyper-translatable (HT) elements, and the 3'-UTR from CPMV RNA-2 which enables enhanced translation and high accumulation of recombinant proteins in plants.

minimal 35S-CaMV promoter
(SEQ ID NO: 2)
gaaacctcctcggattccattgcccagctatctgtcactttattgagaa gatagtggaaaaggaaggtggctcctacaaatgccatcattgcgataaa ggaaaggccatcgttgaagatgcctctgccgacagtggtcccaaagatg gacccccacccacgaggagcatcgtggaaaaagaagacgttccaaccac gtcttcaaagcaagtggattgatgtgatatctccactgacgtaagggat gacgcacaatcccactatccttcgcaagacccttcctctatataaggaa gttcatttcatttggagagg 5'UTR HT-CPMV
(SEQ ID NO: 3)
tattaaaatcttaataggttttgataaaagcgaacgtggggaaacccga accaaaccttcttctaaactctctctcatctctcttaaagcaaacttct ctcttgtctttcttgcgtgagcgatcttcaacgttgtcagatcgtgctt cggcaccagtacaacgttttctttcactgaagcgaaatcaaagatctct ttgtggacacgtagtgcggcgccattaaataacgtgtacttgtcctatt cttgtcggtgtggtcttgggaaaagaaagcttgctggaggctgctgttc agccccatacattacttgttacgattctgctgactttcggcgggtgcaa tatatctacttctgcttgacgaggtattgttgcctgtacttctttcttc ttcttcttgctgattggttctataagaaatctagtattttctttgaaac agagttttcccgtggttttcgaacttggagaaagattgttaagcttctg tatattctgcccaaatttgtcgggccc 3'UTR HT-CPMV
(SEQ ID NO: 4)
atttctttagtttgaatttactgttattcggtgtgcatttctatgttt ggtgagcggttttctgtgctcagagtgtgtttattttatgtaatttaat ttctttgtgagctcctgtttagcaggtcgtcccttcagcaaggacacaa aaagattttaattttattaaaaaaaaaaaaaaaaagaccggg The promoter sequence may consist of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements, derived from different promoters found in nature, or even be comprised of synthetic DNA segments, A promoter may also contain DNA sequences that are involved in the binding of protein factors which control the effectiveness of transcription initiation in response to physiological or developmental conditions.

Examples of enhancers include elements from the CaMV 35S promoter, octopine synthase genes (Ellis et al., 1987), the rice actin I gene, the maize alcohol dehydrogenase gene (Callis 1987), the maize shrunken I gene (Vasil 1989), tobacco etch virus (TEV) and tobacco mosaic virus (TMV) omega translation enhancers (Gallie 1989) and promoters from non-plant eukaryotes (e.g. yeast; Ma 1988). Vectors for use in accordance with the present invention may be constructed to include such an enhancer element. The use of an enhancer element, and particularly multiple copies of the element, may act to increase the level of transcription from adjacent promoters when applied in the context of plant transformation.

The termination region may be selected from the group consisting of a nopaline synthase (nos), a vegetative storage protein (vsp), or a proteinase inhibitor-2 (pint) termination region.

Signal Peptides

Plant expression vectors, particularly binary vectors, and especially the minimally sized binary vectors according to any one of the preceding embodiments as described herein, which are functional in a plant cell and may be used within the method of the present invention, may further comprise a nucleotide sequence encoding a signal peptide that targets the newly expressed protein to a subcellular location. Signal peptides that may be used within such vector molecules are, for example, those selected from a group consisting of a vacuolar targeting sequence, a chloroplast targeting sequence, a mitochondrial targeting sequence, a sequence that induces the formation of protein bodies in a plant cell or a sequence that induces the formation of oil bodies in a plant cell.

In one embodiment of the invention, the targeting sequence is a signal peptide for import of a protein into the endoplasmic reticulum. Signal peptides are transit peptides that are located at the extreme N-terminus of a protein and cleaved co-translationally during translocation across the endoplasmatic reticulum membrane. A signal peptide that can be used in a vector molecule according to the invention, without being limited thereto, is that naturally occurring at the N-terminus of a light or heavy chain sequence of an IgG, or the patatin signal peptide as described in EP2002807566 and WO2007EP1606, particularly the patatin signal peptide of pC148 as described in Example 9. Any nucleotide sequence that can encode the patatin signal peptide sequence can be used.

In one embodiment, a nucleotide sequence encoding the patatin signal peptide consisting of: MATTKSFLILFFMI-LATTSSTCA (SEQ ID NO: 15) may be used within a vector according to the invention and as described herein in any one of the preceding embodiments.

Further signal peptides can, for example, be predicted by the SignalP prediction tool (Emanuelsson et al., 2007, Nature Protocols 2: 953-971).

In another embodiment of the invention, the targeting sequence may be an endoplasmatic reticulum retention peptide. Endoplasmatic reticulum retention targeting sequences occur at the extreme C-terminus of a protein and can be a four amino acid sequence such as KDEL (SEQ ID NO:22), HDEL (SEQ ID NO:23) or DDEL (SEQ ID NO:24), wherein K is lysine, D is aspartic acid, E is glutamic acid, L is leucine and H is histidine.

In still another embodiment of the invention, the targeting sequence may be a sequence that when fused to a protein results in the formation of non-secretory storage organelles in the endoplasmatic reticulum such as but not limited to those described in WO07/096,192, WO06/056483 and WO06/056484, which are incorporated herein by reference in their entirety. In certain embodiments of the invention, the targeting sequence can be a vacuolar targeting sequence, a chloroplast targeting sequence, a mitochondrial targeting sequence or any other sequence the addition of which results in a specific targeting of the protein fused there onto to a specific organelle within the plant or plant cell.

In one embodiment, the vector molecule according to the invention and as defined in any one of the preceding embodiments further comprises in the T-DNA region a site-specific recombination site for site-specific recombination. In one embodiment, the site-specific recombination site is located downstream of the plant regulatory element. In another embodiment, the site-specific recombination site is located upstream of the plant regulatory element. In a specific embodiment of the invention, the recombination site is a LoxP site and part of a Cre-Lox site-specific recombination system. The Cre-Lox site-specific recombination system uses a cyclic recombinase (Cre) which catalyses the recombination between specific sites (LoxP) that contain specific binding sites for Cre.

In another specific embodiment, the recombination site is a Gateway destination site. For example, nucleic acids of interest are first cloned into a commercially available "entry vector" and subsequently recombined into a "destination vector". The destination vector can be used for the analysis of promoter activity of a given nucleic acid sequence or number of sequences, for analysis of function, for protein localization, for protein-protein interaction, for silencing of a given gene or for affinity purification experiments. The Gateway cloning technology can be purchased from Invitrogen Inc., USA.

Suppressor of Gene Silencing

In various embodiments, the selected tobacco variety for use in the methods according to any one of the preceding embodiments may comprise a suppressor of gene silencing, particularly a suppressor of gene silencing of viral origin, and particularly a suppressor of gene silencing of a potyvirus or a virus selected from the group consisting of Cucumber necrosis virus (CNV), Havel river virus (HaRV), Pear latent virus (PeLV), Lisianthus necrosis virus, Grapevine Algerian latent virus, Pelargonium necrotic spot virus (PeNSV), Cymbidium ringspot virus (CymRSV), Artichoke mottled crinkle virus (AMCV), Carnation Italian ringspot virus (CIRV), Lettuce necrotic stunt virus, Rice yellow mottle virus (RYMV), Potato virus X (PVX), Potato virus Y (PVY), African cassava mosaic virus (ACMV), cucumber mosaic virus (CMV), Tobacco etch virus (TEV) or Tomato bushy stunt virus (TBSV).

In another embodiment said suppressor of gene silencing is selected from the group consisting of the p19 protein of cucumber necrotic virus (CNV), the p1 protein of rice yellow mottle virus (RYMV), the p25 protein of potato virus X (PVX), the AC2 protein of African cassava mosaic virus (ACMV), the 2b protein of cucumber mosaic virus (CMV) and the helper-component proteinase (HcPro) of tobacco etch virus (TEV).

Detailed descriptions of suppressor of gene silencing including HcPro are provided in WO98/44097, WO01/38512, and WO01/34822, which are incorporated herein by reference in their entirety. An example of a nucleotide sequence encoding HcPro, is provided herein as set forth in SEQ ID NO: 5. and also referred to as P1-HcPro-P3. This sequence can be inserted in a binary vector known in the art or a minimally-sized binary vector of the invention. Accordingly, in an non-limiting example, the expressible HcPro gene sequence comprise the following sequence or a fragment thereof which is functional in enhancing the yield of heterologous protein in tobacco plant.

```
P1-HcPro-P3
                                           (SEQ ID NO: 5)
atggcactcatctttggcacagtcaacgctaacatcctgaaggaagtgt
tcggtggagctcgtatggcttgcgttaccagcgcacatatggctggagc
gaatggaagcattttgaagaaggcagaagagacctctcgtgcaatcatg
cacaaaccagtgatcttcggagaagactacattaccgaggcagacttgc
cttacacaccactccatttagaggtcgatgctgaaatggagcggatgta
ttatcttggtcgtcgcgcgctcacccatggcaagagacgcaaagtttct
gtgaataacaagaggaacaggagaaggaaagtggccaaaacgtacgtgg
ggcgtgattccattgttgagaagattgtagtgccccacaccgagagaaa
ggttgataccacagcagcagtggaagacatttgcaatgaagctaccact
caacttgtgcataatagtatgccaaagcgtaagaagcagaaaaacttct
tgcccgccacttcactaagtaacgtgtatgcccaaacttggagcatagt
gcgcaaacgccatatgcaggtggagatcattagcaagaagagcgtccga
gcgagggtcaagagatttgagggctcggtgcaattgttcgcaagtgtgc
gtcacatgtatggcgagaggaaaagggtggacttacgtattgacaactg
gcagcaagagacacttctagaccttgctaaaagatttaagaatgagaga
gtggatcaatcgaagctcacttttggttcaagtggcctagttttgaggc
aaggctcgtacggacctgcgcattggtatcgacatggtatgttcattgt
acgcggtcggtcggatgggatgttggtggatgctcgtgcgaaggtaacg
ttcgctgtttgtcactcaatgacacattatagcgaccatcaccatcacc
atcacgcgtccgacaaatcaatctctgaggcattcttcataccatactc
taagaaattcttggagttgagaccagatggaatctcccatgagtgtaca
agaggagtatcagttgagcggtgcggtgaggtggctgcaatcctgacac
aagcactttcaccgtgtggtaagatcacatgcaaacgttgcatggttga
aacacctgacattgttgagggtgagtcgggaggaagtgtcaccaaccaa
ggtaagctcctagcaatgctgaaagaacagtatccagatttcccaatgg
ccgagaaactactcacaaggtttttgcaacagaaatcactagtaaatac
aaatttgacagcctgcgtgagcgtcaaacaactcattggtgaccgcaaa
caagctccattcacacacgtactggctgtcagcgaaattctgtttaaag
gcaataaactaacaggggccgatctcgaagaggcaagcacacatatgct
tgaaatagcaaggttcttgaacaatcgcactgaaaatatgcgcattggc
caccttggttctttcagaaataaaatctcatcgaaggcccatgtgaata
acgcactcatgtgtgataatcaacttgatcagaatgggaattttatttg
gggactaaggggtgcacacgcaaagaggtttcttaaaggattttcact
gagattgacccaaatgaaggatacgataagtatgttatcaggaaacata
tcaggggtagcagaaagctagcaattggcaatttgataatgtcaactga
cttccagacgctcaggcaacaaattcaaggcgaaactattgagcgtaaa
gaaattgggaatcactgcatttcaatgcggaatggtaattacgtgtacc
catgttgttgtgttactcttgaagatggtaaggctcaatattcggatct
aaagcatccaacgaagagacatctggtcattggcaactctggcgattca
aagtacctagaccttccagttctcaatgaagagaaaatgtatatagcta
```

-continued

```
atgaaggttattgctacatgaacattttctttgctctactagtgaatgt

caaggaagaggatgcaaaggacttcaccaagtttataagggacacaatt

gttccaaagcttggagcgtggccaacaatgcaagatgttgcaactgcat

gctacttactttccattctttacccagatgtcctgagtgctgaattacc

cagaattttggttgatcatgacaacaaaacaatgcatgttttggattcg

tatgggtctagaacgacaggataccacatgttgaaaatgaacacaacat

cccagctaattgaattcgttcattcaggtttggaatccgaaatgaaaac

ttacaatgttggagggatgaaccgagatatggtcacacaaggtgcaatt

gagatgttgatcaagtccatatacaaaccacatctcatgaagcagttac

ttgaggaggagccatacataattgtcctggcaatagtctccccttcaat

tttaattgccatgtacaactctggaacttttgagcaggcgttacaaatg

tggttgccaaatacaatgaggttagctaacctcgctgccatcttgtcag

ccttggcgcaaaagttaactttggcagacttgttcgtccagcagcgtaa

tttgattaatgagtatgcgcaggtaattttggacaatctgattgacggt

gtcagggttaaccattcgctatccctagcaatggaaattgttactatta

agctggccacccaagagatggacatggcgttgagggaaggtggctatgc

tgtgacctctgcagatcgttcaaacatttggcaataa
```

Heterologous Protein

In various embodiments, infiltration of the selected variety, breeding line, or cultivar of *Nicotiana tabacum* within a method according to any one of the preceding embodiments may be performed with a selected strain of the *Agrobacterium* species comprising an expressible nucleotide sequence encoding a heterologous protein or polypeptide selected from the group consisting of growth factors, receptors, ligands, signaling molecules; kinases, enzymes, hormones, tumor suppressors, blood clotting proteins, cell cycle proteins, metabolic proteins, neuronal proteins, cardiac proteins, proteins deficient in specific disease states, antibodies or a fragment thereof, immunoglobulins, antigens, proteins that provide resistance to diseases, antimicrobial proteins, interferons, and cytokines. In various embodiments, the heterologous protein or polypeptide is a human protein or polypeptide, a modified human protein or polypeptide, a chimeric protein or polypeptide. In various embodiments, the heterologous protein or polypeptide is not a protein or polypeptide of a plant pathogen, or more specifically, not a protein or polypeptide of a fungal plant pathogen, a viral plant pathogen, a bacterial plant pathogen, a pathogen of species of Solanaceae, a pathogen of *Nicotiana*, or a pathogen of tobacco.

The expressible nucleotide sequence may comprises a sequence that has been optimized for expression in plant cells, particularly in plant cells of plants of the genus *Nicotiana*, particularly *Nicotiana tabacum*. Although the expressible nucleotide sequence may be different from the native human coding sequence, the amino acid of the translated product is identical. One or more codons in the expressible nucleotide sequence have been replaced with preferred codons according to the known codon usage of plant, particularly a plant of the genus *Nicotiana*, particularly *Nicotiana tabacum*, resulting in a pattern of preferred codons encoding the same amino acids in an expressible nucleotide sequence that enables increased expression in plant or tobacco plant (relative to using the native coding sequence). Techniques for modifying a nucleotide sequence for such purposes are well known, see for example, U.S. Pat. Nos. 5,786,464 and 6,114,148.

In one aspect, antigen encoding sequences are used within the method of the invention as described herein in any one of the preceding embodiments including sequences for inducing protective immune responses (for example, as in a vaccine formulation). Such suitable antigens include but are not limited to microbial antigens (including viral antigens, bacterial antigens, fungal antigens, parasite antigens, and the like); antigens from multicellular organisms (such as multicellular parasites); allergens; and antigens associated with human or animal pathologies (e.g., such as cancer, autoimmune diseases, and the like). In one preferred aspect, viral antigens include, but are not limited to: HIV antigens; antigens for conferring protective immune responses to influenza; rotavirus antigens; anthrax antigens; rabies antigens; and the like. Vaccine antigens can be encoded as multivalent peptides or polypeptides, e.g., comprising different or the same antigenic encoding sequences repeated in an expression construct, and optionally separated by one or more linker sequences.

In one embodiment, the expressible nucleotide sequence encodes a light chain of an antibody, a heavy chain of an antibody, or both a light chain and a heavy chain of an antibody. In a specific embodiment, the heavy chain or light chain is that of an antibody that binds human CD20. In another specific embodiment, the heavy chain or light chain is that of an antibody that binds human CD20 with the antibody binding site of rituximab.

In various embodiments, the expressible nucleotide sequence encodes a heterologous protein or polypeptide selected from the group consisting of an influenza virus antigen, particularly a haemagglutinin (HA). Influenza viruses are enveloped virus that bud from the plasma membrane of infected mammalian cells. They are classified into types A, B, or C, based on the nucleoproteins and matrix protein antigens present. Influenza type A viruses may be 15 further divided into subtypes according to the combination of hemagglutinin (HA) and neuraminidase (NA) surface glycoproteins presented. HA governs the ability of the virus to bind to and penetrate the host cell.

Currently, 16 HA (H1-H16) subtypes are recognized. Each type A influenza virus presents one type of HA and one type of NA glycoprotein. HA protein that can be produced by the methods of the invention include H1, H2, H3, H4, H5, H6, H7, H8, H9, H10, H11, H12, H13, H14, H15 or H16 or fragment or portion thereof. Examples of subtypes comprising such HA proteins include A/New Caledonia/20/99 (H1N1), A/Indonesia/512006 (H5N1), A/chicken/New York/1995, A/herring gull/DE/677/88 (H2N8), A/Texas/32/2003, A/mallard/MN/33/00, A/duck/Shanghai/1/2000, A/northern pintail/TXI828189/02, A/Turkey/Ontario/6118/68(H8N4), A/shoveler/Iran/G54/03, A/chicken/Germany/N/1949(H10N7), A/duck/England/56(H11N6), A/duck/Alberta/60176 (H12N5), A/Gull/Maryland/704/77(H13 N6), A/Mallard/Gurjev/263/82, A/duck/Australia/341/83 (H15N8), A/black-headed gull/Sweden/5/99(H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1I2005 (H5N1), A/Vietnam/1194/2004 (H5N1), A/Teal/HongKong/W312/97 (H6N1), A/Equine/Prague/56 (H7N7), A/HongKong/1073/99 (H9N2). It is contemplated that some of the influenza viruses having one of the above mentioned H subtypes can cause an infection in human, and because of its origin, can lead to a pandemic. Many of the antigens of these subtypes (H4, H5, H6, H7, H8, H9, H10, H1, H12, H13, H14, H15, H16) can thus be used in a pandemic influenza vaccine. The subtypes H1, H2, H3 are the major subtypes that are involved in human influenza infection and antigens of such subtypes are contemplated for use in a seasonal influenza vaccine.

It is contemplated any nucleotide sequence that encodes an influenza haemagglutinin or an immunogenic fragment thereof can be used in the methods of the invention, such that the haemagglutinin polypeptide or a fragment thereof is produced in a host *N. tabacum* variety. For example, any of the biological sequences of influenza haemagglutinin reported in public databases, such as Genbank (Nucleic Acids Research 2004 Jan. 1; 32(1):23-6), or the Influenza Research Database (IRD; see www.fludb.org or Squires et al. BioHealthBase: informatics support in the elucidation of influenza virus host pathogen interactions and virulence. Nucleic Acids Research (2008) vol. 36 (Database issue) pp. D497) can be used according to the present invention.

An example of a nucleotide sequence encoding a heterologous protein of interest is provided below and set forth in SEQ ID NO: 8. This nucleotide sequence encodes the mature influenza haemagglutinin 5 (H5) and the codons have been optimized for expression of the sequence in plants. Accordingly, the invention contemplates vectors according to any one of the preceding embodiments as described above comprising, in the T-DNA region and operably linked to a plant regulatory element, a nucleotide sequence encoding a mature influenza haemaglutinin 5 exhibiting at least 90%, 92%, 94%, 96%, 98%, 99% or 99.5% sequence identity to SEQ ID NO: 8.

```
Mature Optimized HEI (H5)
                                        (SEQ ID NO: 8)
atggagaaaatagtgcttcttcttgcaatagtcagtcttgttaaaagtg

atcagatttgcattggttaccatgcaaacaattcaacagagcaggttga

cacaatcatggaaaagaacgttactgttacacatgcccaagacatactg

gaaaagacacacaacgggaagctctgcgatctagatggagtgaagcctc

taattttaagagattgtagtgtagctggatggctcctcgggaacccaat

gtgtgacgaattcatcaatgtaccggaatggtcttacatagtggagaag

gccaatccaaccaatgacctctgttacccagggagtttcaacgactatg

aagaactgaaacacctattgagcagaataaaccattttgagaaaattca

aatcatccccaaaagttcttggtccgatcatgaagcctcatcaggagtt

agctcagcatgtccatacctgggaagtccctcctttttagaaatgtgg

tatggcttatcaaaaagaacagtacatacccaacaataaagaaaagcta

caataataccaaccaagaggatcttttggtactgtggggaattcaccat

cctaatgatgcggcagagcagacaaggctatatcaaaacccaaccacct

atatttccattgggacatcaacactaaaccagagattggtaccaaaaat

agctactagatccaaagtaaacgggcaaagtggaaggatggagttcttc

tggacaattttaaaacctaatgatgcaatcaacttcgagagtaatggaa

atttcattgctccagaatatgcatacaaaattgtcaagaaaggggactc

agcaattatgaaaagtgaattggaatatggtaactgcaacaccaagtgt

caaactccaatgggggcgataaactctagtatgccattccacaacatac
```

-continued

```
accctctcaccatcggggaatgccccaaatatgtgaaatcaaacagatt

agtccttgcaacagggctcagaaatagccctcaaagagagagcagaaga

aaaaagagaggactatttggagctatagcaggttttatagagggaggat

ggcagggaatggtagatggttggtatgggtaccaccatagcaatgagca

ggggagtgggtacgctgcagacaaagaatccactcaaaaggcaatagat

ggagtcaccaataaggtcaactcaatcattgacaaaatgaacactcagt

ttgaggccgttggaagggaatttaataacttagaaaggagaatagagaa

tttaaacaagaagatggaagacgggtttctagatgtctggacttataat

gccgaacttctggttctcatggaaaatgagagaactctagactttcatg

actcaaatgttaagaacctctacgacaaggtccgactacagcttaggga

taatgcaaaggagctgggtaacggttgtttcgagttctatcacaaatgt

gataatgaatgtatggaaagtataagaaacggaacgtacaactatccgc

agtattcagaagaagcaagattaaaaagagaggaaataagtggggtaaa

attggaatcaataggaacttaccaaatactgtcaatttattcaacagtg

gcgagttccctagcactggcaatcatgatggctggtctatctttatgga

tgtgctccaatggatcgttacaatgcagaatttgcatttaa
```

Inoculum Preparation and Cell Density

In one embodiment of the invention, different *Agrobacterium* strains such as *Agrobacterium tumefaciens* or *Agrobacterium rhizogenes* bacteria may be used for the preparation of inoculum as exemplified in Example 1. The *Agrobacterium* strains may comprise a binary vector containing the T-DNA with the gene of interest under control of plant regulatory elements grown up to $OD_{600}$>1.6. The *Agrobacterium* strains may be collected by centrifugation and resuspended in infiltration solution at a cell density ($OD_{600}$) of at least 2.1, at least 2.4, at least 2.7, at least 3.0, at least 3.3, at least 3.6, at least 3.8, at least 3.9, at least 4.0. In a specific embodiment, the $OD_{600}$ of the infiltration solution is >2.

In another embodiment of the invention, *Agrobacterium* strains may be further diluted in infiltration solution and, as an optional measure, acetosyringone may be added to induce virulence.

In further embodiments of the invention, two or more *Agrobacterium* suspensions may be prepared in accordance with the present invention and as described herein. Said two or more suspensions may then either be used separately for infiltration of compatible *Nicotiana tabacum* varieties, breeding lines, or cultivars or, in an alternative approach, may first be mixed before infiltration. Particularly, a first *Agrobacterium* suspension harboring a first binary vector with a first expressible gene, for example a coding sequence that encodes a protein or polypeptide, particularly a heterologous protein or polypeptide such as those mentioned in the previous section, may be prepared as described herein and mixed with a second *Agrobacterium* suspension harbouring a second binary vector with a second expressible gene, for example a coding sequence that encodes a suppressor of gene silencing.

In another embodiment of the invention, the prepared inoculum as described herein can be stored for up to a week at 4-6° C. before use.

As exemplified in Examples 11, 12 and 14, respectively, the invention also provides further improvements to the above described method of inoculum preparation that further enhances the overall yield of heterologous polypeptides.

In one embodiment of the invention, the Agrobacteria are grown and then harvested by centrifugation and resuspended in a solution, preferably in an infiltration solution, preferably to $OD_{600}$>2.0, to generate a concentrated inoculum. Alternatively, the Agrobacteria are kept in culture medium without centrifugation and without resuspension. In a specific embodiment, the *Agrobacterium* cells that are cultured for infiltration are grown to a desired optical density without antibiotic selection, The inoculum may be used immediately or stored for later use. At the day of infiltration, different concentrated inocula comprising different strains of *Agrobacterium* as described herein or identical strains of *Agrobacterium* comprising binary vectors with different protein coding sequences, may be mixed together at different ratios or ratio combinations, for example at a ratio of 3:1, 1.67:1, 1:3, 1:1 and then diluted in infiltration solution to a final $OD_{600}$ to be defined. For example, in one embodiment, the bacterial solution may have a final OD600 of 0.32 or 0.85. The inocula may be equilibrated to room temperature for a period to be defined, for example, 30 minutes. The inocula may be sequentially diluted to OD600 of in infiltration solution to obtain lower bacterial densities.

In a preferred embodiment of the invention, the *Agrobacterium* strain, such as AGL1, may harbor a gene or gene construct, for example a reporter gene, e.g. tGFP, or a suppressor of silencing, e.g. HcPro.

In a preferred embodiment of the invention, the *Agrobacterium* strain is AGL1, the final OD of the inoculum is 0.7, the ratio of AGL1 cells comprising an expressible gene of interest versus AGL1 cells comprising an expressible sequence of HcPro in the inoculum is 2.5 to 1, and the *Nicotiana tabacum* variety is PM132, Plant Infiltration Once a compatible combination of *Nicotiana tabacum* variety, breeding line, or cultivar and an *Agrobacterium* strain has been identified as described above. Any known plant infiltration method can be used within the method according to the invention, such as but not limited to particle gun delivery of a nucleic acid molecule comprising the gene coding for a desired protein in an expressible manner, *Agrobacterium*-mediated delivery of a binary vector comprising the expressible gene, electroporation of protoplasts, and polyethylene glycol-mediated delivery of naked DNA into plant protoplasts. Particle bombardment usually reaches only a few cells and the DNA must reach the cell nucleus for transcription to be accomplished, and is thus not very efficient for transient expression.

The use of *Agrobacterium* delivered by infiltration (agroinfiltration) can deliver foreign genes to significantly higher number of cells. The original system of *Agrobacterium* infiltration for transient expression was described by Kapila et al., Plant Sci. 122: 101-108 (1997) and was developed for rapid testing of the functionality of a protein thought to be useful for disease resistance of the plant tissue.

In various embodiments of the invention, systems are provided to treat intact whole plants, particularly whole and intact plants or a plant parts such as plant organs or plant tissues that have been contacted with *Agrobacterium* cells, by exposure to low atmospheric pressure or a vacuum. The systems used in the method according to the present invention may comprise a chamber for receiving a whole plant, particularly a whole and intact plant or a plant part such as a plant organ or plant tissue, or a plurality of such whole plants or plant parts, and a means for creating a low fluid pressure environment and optionally delivering negative or positive fluid pressure, or a combination of both negative and positive fluid pressure.

In one embodiment of the invention, systems are provided to treat intact whole plants, particularly whole and intact plants or a plant parts such as plant organs or plant tissues that have been contacted with *Agrobacterium* cells upon exposure to low atmospheric pressure or a vacuum. The systems use in the method according to the present invention may comprise a chamber for receiving a whole plant, particularly a whole and intact plant or a plant part such as a plant organ or plant tissue, or a plurality of such whole plants or plant parts, and a means for creating a low fluid pressure environment and optionally delivering positive fluid pressure.

In another embodiment, the invention contemplates using an improved method for introducing *Agrobacterium* cells into a whole plant, particularly a whole and intact plant or a plant part such as a plant organ or plant tissue as disclosed in co-pending application no EP 10 16 9888.4, filed Jul. 16, 2010, the disclosure of which is incorporated herein in its entirety. The method provides positive fluid pressure, or a combination or positive and negative fluid pressure, to facilitate *Agrobacterium* cells to infiltrate a whole plant, particularly a whole and intact plant or a plant part such as a plant organ or plant tissue, unlike methods known in the art which use a vacuum or negative pressure. The invention also provides systems and means for use in the method according to the present invention for delivering positive fluid pressure to whole plants, particularly whole and intact plants or a plant parts such as plant organs or plant tissues that are or have been contacted with *Agrobacterium* cells.

Positive fluid pressure is delivered when the whole plant, particularly the whole and intact plant or the plant part, and bacteria are subjected to treatment with one or more pressure cycle(s) under closed conditions. Fluid pressure is the pressure at some point within a fluid, such as water or air. For example, under a closed condition, the volume in which the fluid is contained is constant. In various embodiments of the invention, the fluid pressure is the air pressure within a chamber of a fixed volume.

Positive pressure values useful in the invention can thus be expressed in terms of a percentage value of the ambient air pressure, for example and without limitation, 110%, 125%, 150%, 175%, 200%, 250%, 300%, 350%, 400%, 350%, 500%, 550%, 600%, 650%, 700%, 750%, 800%, 850%, 900%, 950%, 1000%, 1050%, 1110%, 1150%, 1200%, or any intermediate value, or any value greater than the foregoing. A similar convention can be used for describing negative pressure which is a pressure value lower than the ambient air pressure.

A positive pressure can alternatively be expressed in terms of an absolute value, for example and without limitation, 1.1 atm, 1.5 atm, 2 atm, 2.5 atm, 3 atm, 3.5 atm, 4 atm, 4.5 atm, 5 atm, 5.5 atm, 6 atm, 6.5 atm, 7 atm, 7.5 atm, 8 atm, 8.5 atm, 9 atm, 9.5 atm, 10 atm, 10.5 atm, 11 atm, 11.5 atm, 12 atm, and so on; or 1.1 bar, 1.5 bar, 2 bar, 2.5 bar, 3 bar, 3.5 bar, 4 bar, 4.5 bar, 5 bar, 5.5 bar, 6 bar, 6.5 bar, 7 bar, 7.5 bar, 8 bar, 8.5 bar, 9 bar, 9.5 bar, 10 bar, 10.5 bar, 11 bar, 11.5 bar, 12 bar, or any intermediate value, or any value greater than the foregoing. Where an ambient air pressure is not provided for comparison in a description herein, the ambient air pressure is intended to be standard atmospheric pressure on Earth at sea level.

The term "pressure cycle" used herein refers to a series of changes in pressure over a period of time. In one embodiment, a pressure cycle comprises a target pressure, that is, the pressure that is to be reached within a given time period. For example, during a pressure cycle, a desired pressure in a chamber starts from being in equilibrium with ambient air pressure, changes to the target pressure, and returns to ambient air pressure. Accordingly, a chamber used in the invention can start a pressure cycle by increasing pressure above atmospheric air and end a pressure cycle by equilibrating with atmospheric air.

In the methods of the invention, a plurality of different pressure cycles can be applied and each can be applied one or more times, such as but not limited to two, three, four, five, six, seven, eight, nine, or ten times. Accordingly, in a method of the invention or even in a pressure cycle, the variation of pressure over time can be expressed by a graph or a waveform, such as a sine wave, a square wave, a triangle wave, or a sawtooth wave, or any waveform that approximates one of the foregoing.

Particularly, a pressure cycle may comprise a target pressure that is a positive pressure. In certain embodiments, the method of the invention does not comprise use of a target pressure that is a negative pressure. In other embodiments, the use of a first target pressure that is a positive pressure is contemplated, as well as a second target pressure that is a negative pressure. In other embodiments, a first target pressure is a negative pressure, and the second target pressure is a positive pressure. A rest period may be included between pressure cycles.

In certain embodiments, *Agrobacterium* cells comprising the expression construct are infiltrated into a whole plant, particularly a whole and intact plant or a part of a whole and intact plant, such as a plant organ or plant tissue. In one embodiment, the infiltration is carried ourout in the presence of a surfactant, including anionic, cationic, non-ionic, and zwitterionic surfactants. Non-limiting examples of a surfactant that can be used are Triton X-100 or Silwet L-77, a strong surfactant that shows relatively low toxicity to plants.

In one embodiment, a whole and intact plant is positioned upside down inside a chamber and its leaves are wholly immersed in a liquid comprising *Agrobacterium* cells. The chamber is connected to a source of low air pressure via an inlet valve. For example, to create a low atmospheric pressure (about 50 mbar).

In addition to the above equipment, the systems for use in the method according to the invention may optionally further comprise means for transporting a plurality of whole plants or plant parts such as plant organs or plant tissues from a location to the chamber, means for facilitating the contact of a plurality of whole plants or plant tissues with *Agrobacterium* cells, means for receiving a plurality of whole plants or plant tissues in the chamber, means for positioning and repositioning the plurality of whole plants or plant parts such as plant organs or plant tissues in the chamber, means for retrieving the plurality of whole plants or plant parts from the chamber. Preferably, one or more of the foregoing means are automated electro-mechanical systems and include but are not limited to motorized transport systems, factory automation systems, security systems, process control systems, data communication systems, data storage systems and computing systems.

In various embodiments, cells of *Agrobacterium* harboring expression constructs with a gene or genes, particularly a heterologous gene or genes, are used to deliver the gene(s) to a whole and intact plant or a plant part such as a plant organ or plant tissue, for transient expression in the cells and/or extracellular spaces of the plant or plant parts. Generally, a suitable expression construct comprises: at least one T-DNA border sequence, an expression regulatory sequence (for example, a, promoter which may be inducible or constitutive, a promoter whose activity is tissue-specific or tissue-biased), and a gene operably linked to the expression regulatory sequence. In certain embodiments, an expression construct is part of a vector comprising one or more origins of replication, at least one origin of replication suitable for replicating the vector comprising the expression construct in *Agrobacterium* species.

The positive pressure infiltration method can be used for obtaining transient expression of many species of plants, including but not limited to: tobacco (*Nicotiana* species), lettuce, alfalfa, mung bean, spinach, dandelion, radicchio, arugula, endive, escarole, chicory, artichoke, maize, potato, rice, soybean, cotton, small grain cereals, wheat, barley, *Sorghum*, sugar beet, canola, Crucifera (e.g., *Brassica, Arabidopsis*) duckweed, and tomato.

Suitable plant organ or tissue generally can be any part of the plant. In one preferred aspect, plant tissue is leaf tissue. In one aspect, the plant tissue is leaf tissue from a plant comprising leaves of at least about 7-8 cm in at least one dimension.

Greenhouse Practices

Incubation in an Inverted Position

In another aspect of the invention, a general method is provided for incubating a plant after infiltration with a bacterial suspension comprising an expressible nucleotide sequence of a protein or polypeptide, particularly a heterologous protein or polypeptide, said method comprising incubating the plant in an inverted position. Preferably, the plant that is incubated in an inverted position is a whole plant that is infiltrated with a suspension of *Agrobacterium* cells comprising an expressible nucleotide sequence of a protein or polypeptide, particularly a heterologous protein or polypeptide.

In another embodiment, the plant that is incubated in an inverted position is a transgenic plant.

In certain embodiments, the invention relates to the method according to any of the preceding embodiments, wherein said incubating step comprises incubating the infiltrated plant in an inverted position. Also provided is a greenhouse that is adapted to support the incubation of infiltrated plants in an inverted position for any length of time, particularly for a period of between 5 day and 10 days, wherein the inverted infiltrated plants is illuminated from above. In one aspect of the invention, the plants are illuminated for 7 to 9 hours per 24 hours, particularly for 8 hours per 24 hours.

This method leads to an increased expression of recombinant protein as shown in Example 13.

In one embodiment of the invention, the method comprising incubation of a plant in an inverted position may be used within the method according to any of the preceding aspects or embodiments, particularly within the incubation step (iii) as described herein.

In one embodiment of the invention, the modification of incubating a plant in an inverted position, may be applied to the method according to the invention taking into account any of the preceding aspects or embodiments, particularly in the context of incubation step (iii) as described herein.

Illumination

In yet another aspect of the invention, a general method is provided for incubating a plant after infiltration with a bacterial suspension comprising an expressible nucleotide sequence of a protein or polypeptide, particularly a heterologous protein or polypeptide, said method comprising incubating the plant under daylight conditions for 5 hours to 15 hours per day (24 hours), 5 hours to 10 hours, 7 to 9 hours, preferably for eight hours per day (24 hours). The method is particularly useful for improving the level of transient expression of the heterologous protein as exemplified in Example 15.

In one embodiment, the infiltrated plant is a whole plant that is infiltrated with a suspension of *Agrobacterium* cells comprising an expressible nucleotide sequence of a protein or polypeptide, particularly a heterologous protein or polypeptide and incubated under daylight conditions for seven to nine hours per day, preferably eight hours per day. In certain embodiments, the invention relates to the method according to any of the preceding embodiments, wherein said incubating step comprises incubating the infiltrated plant in an inverted position.

In one embodiment of the invention, the modification of incubating the plant under daylight conditions for seven to nine hours per day, preferably eight hours per day, may be applied to the method according to the invention taking into account any of the preceding aspects or embodiments, particularly in the context of incubation step (iii) as described herein.

Planting Density

In yet another aspect of the invention, a general method is provided comprising growing a plurality of plants at high density within a defined area before infiltrating said plants with a bacterial suspension comprising an expressible nucleotide sequence of a protein or polypeptide, particularly a heterologous protein or polypeptide. It is also contemplated that after infiltration, the infiltrated plant is incubated at a high density within a defined area. Also encompassed is a method wherein a plurality of plants are planted at high density both before and after infiltration.

Particularly, the method comprises growing a plurality of plants at a density of at least 25 to 500 plants per square meter, at least 50 to 400 plants per square meter, at least 100 to 300 plants per square meter, at least 150 to 250 plants per square meter, at least 100 to 900 plants per square meter. In one embodiment, the plants are grown at a density of at least 100 plants per square meter. In another embodiment, the plants are grown at a density of or at least 500 plants per square meter. The plurality of plants, after having been grown at the above conditions for a period of between 30 days and 50 days after sowing, particularly of between 40 day and 50 days after sowing, but particularly for 46 days after sowing, is infiltrated with a suspension of *Agrobacterium* cells comprising an expressible nucleotide sequence of a protein or polypeptide, particularly a heterologous protein or polypeptide at an $OD_{600}$ identified in the preceding paragraphs.

In one embodiment, after infiltration, the plants are incubated in an up-right position.

In another, after infiltration, the plants are incubated in an inverted position. In particular, the infiltrated plants are incubated in an inverted position for any length of time, particularly for a period of between 5 day and 10 days, wherein the inverted infiltrated plants are illuminated from above. In one aspect of the invention, the plants are illuminated for 7 to 9 hours per 24 hours, particularly for 8 hours per 24 hours.

This method leads to an increased expression of recombinant protein as shown in Example 14.

The method is particularly useful for reducing the cost of producing the heterologous protein. Also provided is a greenhouse that is adapted to grow plants at a density of at least 25 to 500 plants per square meter, or at least 100 infiltrated plants per square meter.

In one embodiment, the invention relates to the method according to any of the preceding embodiments, wherein said method is modified to comprise a step of growing a plurality of *Nicotiana tabacum* plants at high density within a defined area before infiltrating said plants with a bacterial suspension comprising an expressible nucleotide sequence of a protein or polypeptide, particularly a heterologous protein or polypeptide. In particular, the plurality of *Nicotiana tabacum* plants is grown at a density of at least 25 to 500 plants per square meter, at least 50 to 400 plants per square meter, at least 100 to 300 plants per square meter, at least 150 to 250 plants per square meter, but particularly at least 100 plants per square meter.

In one embodiment of the invention, method for incubating a plurality of infiltrated plants within a defined area may be used within the method according to any of the preceding aspects or embodiments, particularly within the incubation step (iii) as described herein.

In one embodiment of the invention, the modification of growing a plurality of plants prior to infiltration at a high density with a defined area may be applied to the method according to the invention taking into account any of the preceding aspects or embodiments.

Enzymatic Depredation of Cell Wall of Infiltrated Plants

In yet another aspect of the invention, a general method is provided comprising treating a whole, intact *Agrobacterium*-infiltrated plant with one or more enzymes that degrade or digest plant cell wall to assist the extraction of heterologous protein. In one embodiment, the method comprises infiltrating the *Agrobacterium*-infiltrated plant with one or more enzymes by techniques known in the art, including but not limited to syringe infiltration, vacuum infiltration and infiltration under positive fluid pressure. The infiltration technique allows prior to mechanically disrupting an *Agrobacterium*-infiltrated plant, delivery of digestive enzymes to the apoplast space which results in the degradation of the cell wall without releasing the majority of the cell content. This infiltration step can be performed using similar equipment that enables the infiltration of whole intact plant with *Agrobacterium* cell suspension. This method can be used as an optional step in the various method for producing a heterologous protein of interest as described in any one of the preceding embodiments. Example 17 describes an experiment which demonstrates the utility of this aspect of the invention with *Agrobacterium*-infiltrated tobacco plants that are producing influenza hemaglutinin 5 (H5).

Many enzymes used in industrial process to breakdown the cell wall of plants can be used, including but not limited to cellulases, hemicellulases, xylanases, pectinases and polygalacturonases. Cellulases that can be used include endoglucanases (E.C. 3.2.1.4), cellobiohydrolases (also called exoglucanase, E.C. 3.2.1.91), or β-glucosidases. (also called cellobiase, E.C. 3.2.1.21). Endoglucanases hydrolyze β-glycoside bonds internally and randomly along the cellulose chains whereas cellobiohydrolases remove cellobiose molecules from the reducing and non-reducing ends of the chains. β-Glucosidases hydrolyze the cellobiose to two molecules of glucose, and therefore eliminate the inhibition of cellobiose on cellobiohydrolases and endoglucanases. Enzymes having polygalacturonase activity hydrolyses the glycosidic linkages in a polygalacturonic acid chain which are commonly found in plant cell walls as chains of 1,4-linked α-D-galacturonic acid and methoxylated derivatives. Xylanases (EC3.2.1.8) cleave the β,I-4 linkages between D-xylose which forms the polymer xylan, a major component of plant hemicellulose. Many of these enzymes are obtained from fungi (*Trichoderma* species, *Rhizopus* species and *Aspergillus* species). and microorganisms, and can be purchased commercially as a mixture, e.g., Macerozyme™ (cellulose 0.1 U/mg, hemiculluase, 0.25 U/mg, pectinase 0.5 U/mg, bioWORLD, Dublin, Ohio, USA); and Driselase™ (laminarinase, xylanase and cellulose, Sigma-Aldrich, USA).

After infiltration with the enzymes, the plants may be incubated for a period of time ranging from at least 1, 2, 5, 10, 12, 18, to 24 hours.

Yield

In one embodiment, the invention relates to a method for producing a protein or polypeptide, particularly a heterologous protein or polypeptide in *Nicotiana tabacum* according to the preceding aspects or embodiments with the proviso that when the expressible nucleotide sequence encodes a protein, such as a Turbo green fluorescent protein (tGFP) or hemagglutinin H5, the accumulation of the protein is at least 1%, at least 2%, at least 5%, at least 10%, at least 15% or at least 20% of the total soluble protein of the infiltrated plant; or that the accumulation of the polypeptide or protein is at a level which is at least 25%, at least 50%, at least 75%, at least 110%, at least 125%, at least 200%, at least 250%, at least 300%, at least 400%, or at least 500% of that obtainable in *N. benthamiana* when the selected *Agrobacterium* strain comprising the same expressible nucleotide sequence is used as described in step ii) and step iii), as exemplified in Examples 14 and 15, respectively. Methods known in the art can be used to measure and compare the yield of the method and the controls.

System for Commercial-Scale Production of Protein in Plants

In one embodiment, the invention relates to a system for producing a protein or polypeptide, particularly a heterologous protein or polypeptide in *Nicotiana tabacum* plants, which system comprises the following elements: (a) a whole plants of selected *Nicotiana tabacum* varieties, breeding lines or cultivars according to any of the preceding embodiments, (b) a bacterial suspension according to any of the preceding embodiments comprising cells of an *Agrobacterium* strain that is compatible to the selected plants of *Nicotiana tabacum* varieties, breeding lines or cultivars of element (a) such that said plants exhibit less than 20% necrosis, less than 10% necrosis, less than 5% necrosis, less than 2% necrosis, less than 1% necrosis, 5 days after leaves of said variety, breeding line, or cultivar have been injected by a syringe with the selected *Agrobacterium* strain at a cell density of OD600 of 0.32, (c) a means for infiltrating whole plants with *Agrobacterium* cells according to any of the preceding embodiments, and (d) optionally a greenhouse for growing plants at high densities and incubation of the infiltrated plant that is adapted to support (i) growing a plurality of plants at a density of at least 25 to 500 plants per square meter, or at least 100 plants per square meter according to the any of the preceding aspects and as exemplified in Example 14; (ii) incubating the infiltrated plants in an inverted position according to any of the preceding aspects and as exemplified in Example 13 with illumination from above for seven to nine hours per day according to any of the preceding aspects and as exemplified in Example 15.

Pharmaceutical Compositions

After incubating the plant or plant tissue under suitable conditions that allow the expression construct to express the peptide or protein in a plurality of plant cells, the protein can be detected and quantified in the plant or plant part such as the plant organ or plant tissue or in the cells thereof. After harvesting, peptide or protein isolation may be performed using methods routine in the art. For example, at least a portion of the biomass may be homogenized, and recombinant peptide or protein extracted and further purified. Extraction may comprise soaking or immersing the homogenate in a suitable solvent. Purification methods include, but are not limited to, immunoaffinity purification and purification procedures based on the specific size of a peptide, protein or protein complex, electrophoretic mobility, biological activity, and/or net charge of the peptide or protein to be isolated, or based on the presence of a tag molecule in the protein. Characterization of the isolated peptide or protein can be conducted by immunoassay or by other methods known in the art. For example, peptides or proteins can be analyzed on SDS-PAGE gels by Western blotting, or by Coomassie blue staining when the peptide or protein is substantially purified.

Recombinant proteins produced by methods of the invention may be used as pharmaceuticals, and can be expressed for their utility as nutraceuticals and cosmeceuticals, since these products are used for direct ingestion, injection or application (e.g., topical administration) to humans. Recombinant protein also may be expressed which are useful in the production of similarly regulated veterinarian products.

Methods of the invention can also be used to express one or more genes to reproduce enzymatic pathways for chemical synthesis or for industrial processes.

Pharmaceutical compositions of the invention preferably comprise a pharmaceutically acceptable carrier. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion. The carrier can be a parenteral carrier, more particularly a solution that is isotonic with the blood of the recipient. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are nontoxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

BRIEF DESCRIPTION OF FIGURES, TABLES AND SEQUENCES

The present invention is further described by reference to the following non-limiting figures, tables and examples.

FIG. 1 shows schematic diagrams of (A) the minimal plant selectable binary vector pC100 and (B) the minimal binary vector pPMP1.

FIG. 2 shows results of testing of various *N. tabacum* varieties, PM67, PM81, PM92, PM128, PM132, PM133 and PM204, for expression of green fluorescent protein using various suppressors of gene silencing. Plants are infiltrated with a bacterial suspension of A91 (AGL1 strain containing the pC91 gene construct containing a plant expressible tGFP cassette) and AGL1 containing the suppressors of gene silencing p1 (A18), p25 (A19), AC1 (A20), 2b (A21), p19 from CNV (A32) and HcPro (A120). Expression at 6 days post infiltration is displayed in mg per kg frozen fresh weight of leaves.

FIG. 3 shows tobacco varieties Simmaba, PM132, Burley 21, PM16, PM21, K 149, PO1 and PO2 (A) and PM92, Yaka JB 125/3 and PM204 (B) being infiltrated with various *Agrobacterium* strains harbouring a tGFP expression cassette in a pBINPLUS binary vector. All are tested in combination with AGL1(pC120) containing an HcPro suppressor of gene silencing. Plants are vacuum-infiltrated with *Agrobacterium* strains AGL1 (A91), EHA105 (E91), GV2260 (G91), LBA4404 (L91), GV3101 (V91) and Cry-5 (Y91) and AGL1 (pC120). TurboGFP concentration is determined at 6 days post infiltration and is displayed in mg per kg frozen weight of leaves.

FIG. 4 shows Western blot analysis of H5 in crude extracts of *N. tabacum* PM132 and *N. benthamiana* transiently expressing H5. A band of the expected size (75 kDa) is detected in *N. tabacum* PM132 and *N. benthamiana* transiently expressing H5 and not in the mock or wild-type control). Total soluble proteins are extracted from frozen powdered leaf material in Dubelco's PBS 1× at a ratio of 1 g frozen weight to 2 ml extraction buffer. Equal volumes of extracts (corresponding to 45 to 55 μg total protein per well) and H5 control protein are denatured in SDS-containing loading buffer+reducing agent and loaded on a 4-12% Bis-Tris NuPAGE gel. Proteins are transferred to a PVDF membrane using the iBlot apparatus (Invitrogen). Detection of H5: 1) incubation with primary antibody [Rabbit anti-H5, Immunetech #IT-003-005V, 1 mg/0.5 ml], at a 1/1,000 dilution O/N at 4° C.; 2) incubation with secondary antibody [HRP-conjugated goat anti-rabbit, Jackson Cat. #11-035-046, 0.4 mg/ml] at a 1/10,000 dilution for 1 h at room temperature; incubation with HRP-substrate ECL-Plus (GE #RPN2132) for 5 min at room temperature, 4) detection of chemiluminescence with the Chemismart (Exposure 2 min, Aperture 8).

FIG. 5 shows 2D contour plots of the predicted effects of *Agrobacterium* density (OD inoculum) and ratio of A91 to A120 (COI:SoS) in inoculum on TurboGFP expression levels at 6 DPI (in mg per kg frozen weight; values represented in white boxes) for three tobacco varieties: A Burley 21, B PM132 and C PM204.

FIG. 6 shows effects of the removal of centrifugation step in inoculum preparation on tobacco transient expression. Plants of tobacco varieties Burley 21, PM132 and PM204 are co-infiltrated with A91 and A120 prepared from cultures that are either centrifugated and resuspended in Infiltration Solution or directly diluted in infiltration Solution. Fluorometric measurements of tGFP expression are performed at 6 DPI. Bars indicate standard error of the mean.

Figure 1A:
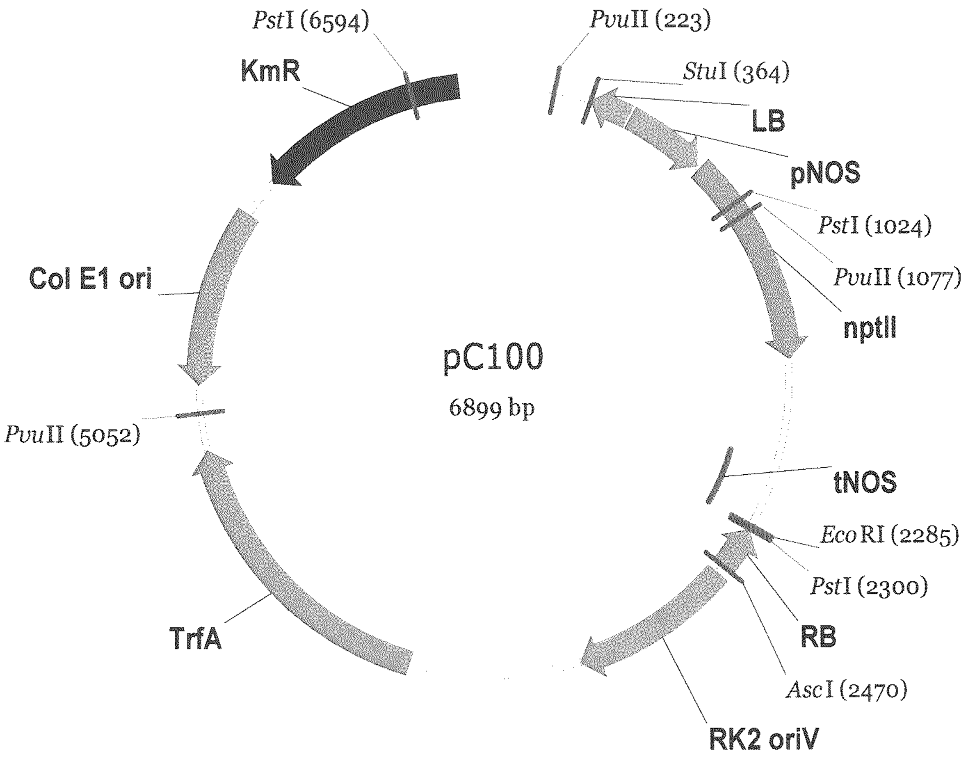

Table 1 lists all *Nicotiana tabacum* varieties tested.

Table 2 lists twenty-six (26) *Nicotiana tabacum* varieties with expression of C5-1 monoclonal antibody above 25% of control *N. benthamiana* as determined by immuno dot-blot ++: signal between 25 and 50% of control *N. benthamiana* and +++: signal equal or above 50% of control *N. benthamiana*. The phenotype of infiltrated plant is given and compared to non-infiltrated plant of same variety.

Table 3 lists the plant characteristics of *N. tabacum* PM132 and PM217 grown at 25 or 100 plants per sq m. Height is in cm, stomatal conductance in μmol/m$^2$ s, chlorophyll content index (CCI) as read from the sensor of a CCM-200 chlorophyll meter (Opti-Science, USA), leaf thickness in mm and water content in %.

Table 4 shows tGFP and H5 expression in leaves of *N. tabacum* PM132 and PM217 plants grown at 25 or 100 plants per sq m before infiltration and after infiltration, incubated for 5 days in upright or upside-down position.

Table 5 shows plant characteristics of *N. tabacum* PM132 grown at 75 plants per sq m used to determine the effect of short and long day incubation post infiltration. Height is in cm, stomatal conductance in μmol/m$^2$ s, chlorophyll content index (CCI) as read from the sensor of a CCM-200 chlorophyll meter (Opti-Science, USA), leaf thickness in mm and water content in %.

In the description and examples, reference is made to the following sequences that are represented in the sequence listing:

SEQ ID NO: 1 depicts the nucleotide sequence of vector pPMP1

SEQ ID NO: 2 depicts the nucleotide sequence of minimal 35S-CaMV promoter

SEQ ID NO: 3 depicts the nucleotide sequence of 5'UTR HT-CPMV

SEQ ID NO: 4 depicts the nucleotide sequence of 3'UTR HT-CPMV

SEQ ID NO: 5 depicts the nucleotide sequence of P1-HcPro-P3

SEQ ID NO: 6 depicts the nucleotide sequence of forward primerPC201F

SEQ ID NO: 7 depicts the nucleotide sequence of reverse primer PC202R

SEQ ID NO: 8 depicts the nucleotide sequence of optimized influenza haemagglutinin 5

SEQ ID NO: 9: depicts the nucleotide sequence of pMMV single enhanced promoter fragment between EcoR1 and Hind3 sites SEQ ID NO: 10: depicts the nucleotide sequence of pMMV double enhanced promoter fragment between EcoR1 and Hind3 sites SEQ ID NO: 11: depicts the nucleotide sequence of pFMV single enhanced promoter fragment between EcoR1 and Hind3 sites SEQ ID NO: 12: depicts the nucleotide sequence of pFMV double enhanced promoter fragment between EcoR1 and Hind3 sites SEQ ID NO: 13: depicts the nucleotide sequence of pPCISV single enhanced promoter fragment between EcoR1 and Hind3 sites SEQ ID NO: 14: depicts the nucleotide sequence of pPCISV double enhanced promoter fragment between EcoR1 and Hind3 sites SEQ ID NO: 15: depicts the amino acid sequence of the patatin signal peptide SEQ ID NO: 16: depicts the patatin tobacco non optimized sequence (slightly modified) as in C146 (in front of heavy chain)

SEQ ID NO: 17: depicts the patatin tobacco optimized sequence as in C148 (in front of light chain)

SEQ ID NO: 18: depicts the nucleotide sequence of rituximab mature heavy chain (tobacco optimized) sequence as in C148

SEQ ID NO: 19: depicts the amino acid sequence of rituximab mature heavy chain

SEQ ID NO: 20: depicts the nucleotide sequence of rituximab mature light chain (tobacco optimized) sequence as in C148

SEQ ID NO: 21: depicts the amino acid sequence of rituximab mature light chain

EXAMPLES

The following examples are provided as an illustration and not as a limitation. Unless otherwise indicated, the present invention employs conventional techniques and methods of molecular biology, cell biology, recombinant. DNA technology, plant biology, plant breeding and protein production.

Example 1: Agroinfiltration of Tobacco Plants

This example describes various methods of infiltrating selected varieties, breeding lines, or cultivars of *Nicotiana tabacum* with *Agrobacterium* cells. Whole plant or plant tissue can be infiltrated with *Agrobacterium* assisted by vacuum, by high pressure or by a syringe without needle. Before infiltration, tobacco plants are grown in the greenhouse in rockwool blocks with 20 hours light period and 4 hours dark period, 26° C./20° C. day/night and 70%/50% relative humidity (day/night). Plants are given fertilizer by sub-irrigation.

Preparation of Inoculum.

*Agrobacterium tumefaciens* or *Agrobacterium rhizogenes* bacteria comprising a binary vector containing the T-DNA with the gene of interest under control of plant regulatory elements is grown up to an $OD_{600}$>1.6 in YEB-medium comprising 2 g/L Beef extract, 0.4 g/L Yeast extract, 2 g/L Bacto-Peptone, 2 g/L Sucrose, 0.1 g/L MgSO4 and suitable antibiotics for selection of the respective *Agrobacterium* strain and binary vector, in an Erlenmeyer flask at 28° C. and 250 rpm on a rotary shaker. The culture is then diluted 1:100 in fresh LB Broth Miller medium containing 10 mM 2-(N-morpholino)ethanesulfonic acid (MES) and suitable antibiotics and further grown at 28° C. and 250 rpm on a rotary shaker up to an $OD_{600}$>2. Bacteria are collected by centrifugation for 15 minutes at 8,000 g and 4° C. Pelleted bacteria are resuspended in infiltration solution containing 10 mM $MgCl_2$ and 5 mM MES (referred to herein as infiltration solution) at a final pH of 5.6, and $OD_{600}$>2. Optionally, bacteria can be further diluted in infiltration solution and acetosyringone can be added to induce virulence. Optionally, a first *Agrobacterium* bacterial suspension prepared as described above, is mixed with a second *Agrobacterium* suspension harbouring a second binary vector with a second expressible gene. A non-limiting example of such a second gene is a coding sequence that encode a suppressor of gene silencing. Optionally, inoculum can be stored for up to a week at 4-6° C. before use.

Syringe Infiltration.

A syringe having the dimensions of a standard 2-ml syringe is filled with the bacterial infiltration solution and, without a needle, pressed against the abaxial side of a leaf. The piston is pushed down to force the entry of the bacterial suspension into the leaf tissue. This is repeated until the majority of the leaf surface is infiltrated. After infiltration, plants are kept in low light for a minimum of 8 hours and during the first day protected from full sunlight. The next day, plants are placed under normal light conditions until harvesting.

Vacuum Infiltration.

Plants are infiltrated by immersion of the aerial parts in a 10 L beaker filled with a bacterial inoculum and exposing the whole of the infected plant or infected plant parts to greatly reduced atmospheric pressure (generally referred to herein as a vacuum). Vacuum infiltration is performed in a glass bell jar (Schott-Duran Mobilex 300 mm) using a V-710 Büchi pump connected to a V-855 regulator and the pressure is decreased from atmospheric pressure (1 bar) to 50 mbar in 3 to 4 minutes. Once reached, the vacuum in the bell jar is kept for 1 minute followed by a return to atmospheric pressure in approximately 2 seconds. Artificial lighting (80-100 μmol photon/$cm^2$) is kept on during the whole infiltration process to ensure consistent light conditions. Following infiltration, plants are placed along with non-infiltrated control plants in the greenhouse until harvesting. Growth conditions such as fertilization, photoperiod and temperature are the same as used before infiltration. Water and fertilizer are administered to plants using a drip irrigation system.

Harvesting and Material Sampling.

Sampling can commence after 16 hours but typically infiltrated leaves or infiltrated areas of a leaf are harvested after 6 days of incubation in the greenhouse. Leaf material is placed in a heat-sealable pouch, sealed and placed between layers of dry-ice for at least 10 minutes. After harvesting, all leaf samples are stored at −80° C. until further processing. Harvested leaves are homogenized to a fine powder using a coffee-grinder on dry-ice, extracted by (i) two steps of vortexing for 20 seconds each in 3 vol/wt extraction buffer containing 50 mM Tris base, 100 mM NaCl, 1 mM EDTA, 0.2% Triton X-100, final pH 7.5, and (ii) by centrifugation at 20,000 g for 15 minutes. Soluble extracts are kept on ice until analysis.

Example 2: Binary Vectors for Transient Expression

This example describes the design and development of the pPMP1 vector and the minimal pC100 binary vector containing a kanamycin resistance gene for selecting transformed plant cells and used in this application.

Construction of T-DNA Region and Backbone Fragment.

The nucleotide sequence of the multi-copy binary vector pBIN61 (Bendahmane et al., 2000. Plant Journal 21: 73-81) of about 13,500 basepairs in length is analysed for nucleic acids having a function in replication, maintenance, selection of transgenic cells and transfer of T-DNA. A new nucleotide sequence is developed only comprising nucleic acids having a function as described above. The resulting nucleotide sequence is chemically synthesized in two parts. A first fragment containing the T-DNA region bordered by a T-DNA right (RB) and T-DNA left (LB) border sequence, the plant selectable kanamycin resistance (nptII) gene of pBIN61 under control of a nopaline synthase (pNOS) promoter and tNOS terminator and unique StuI, AscI and EcoRI restriction site is chemically synthesized with flanking PvuII restriction sites and cloned in the PvuII site of the pUC-derived pMK vector (Geneart, Regensburg, Germany) which further contained a ColE1 replication of origin (Col E1 ori) and bacterial kanamycin resistance gene (KmR), resulting in pGA13. A second fragment containing the backbone region with a ColE1 ori and minimal RK2 oriV origin of replication and gene coding for the RK2 derived TrfA replication initiator protein of pBIN61, is chemically synthesized with unique AscI, StuI and PvuII restriction sites and cloned in the pUC-derived pMA vector (Geneart, Regensburg, Germany) which further contained an ampicillin (ApR) resistance gene, resulting in pGA14.

Design and Development of pC100.

Minimal binary plant selectable vector pC100 (FIG. 1A) is made by combining two fragments, a first fragment and a second fragment that are de novo synthesized. The first fragment contains 1, a kanamycin drug resistance gene functional in *E. coli* and *Agrobacterium* and comprising the neomycin phosphotransferase III gene; 2, a ColE1 origin of replication; 3, a minimal oriV origin of replication (Kowalczyk L. et al., Molecular Microbiology, 2005, 57(5): 1439-1449); 4, the trfA1 gene of an IncP plasmid that activates the oriV (Kongsuwan K. et al., J. Bacteriology, 2006, 188(15): 5501-5509), and 5, unique AscI and StuI restriction endonuclease recognition sites at the extreme ends of the fragment for combining said fragment 1 and fragment 2 to generate the minimal binary vector pC100. The second fragment contains the T-DNA region that contained 6, a T-DNA left border sequence of an *Agrobacterium;* 7, a T-DNA right border sequence of an *Agrobacterium;* 8, optionally, a selectable marker gene for selection of a transgenic plant cell and comprising a neomycin phosphotransferase II gene under control of a nopaline synthase promoter and a nopaline synthase terminator sequence of an *Agrobacterium tumefaciens* nopaline plasmid; 9, an unique EcoRI restriction endonuclease recognition site for cloning of a foreign gene and located between 7, the T-DNA right border and 8, the selectable marker gene, and 10, unique AscI and StuI restriction endonuclease recognition sites at the extreme ends of the fragment for combining said fragment 2 and fragment 1 to generate the minimal binary vector pC100.

Figure 1B:
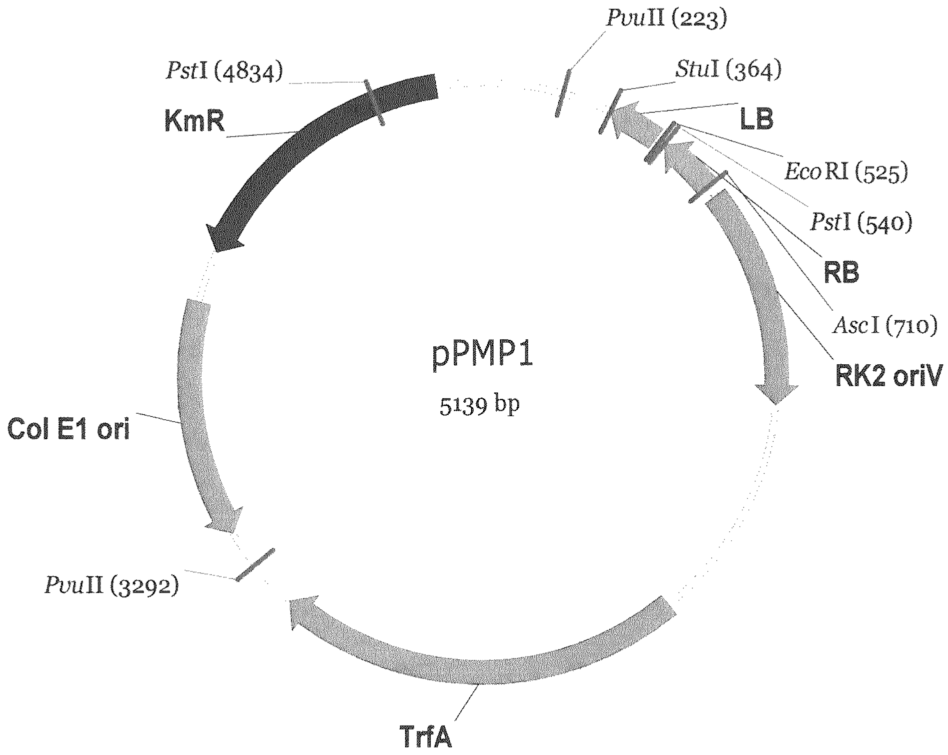

Construction of pPMP1 Minimal Binary Vector.

pPMP1 (5139 bp; FIG. 1B) is constructed by deleting the plant selectable nptII gene from pC100 generating the minimal binary vector pPMP1 with SEQ ID NO: 1. pPMP1 contains a unique EcoRI restriction site at position +1; a LB at position +69 to +94; a first gap sequence of 250 bp wherein the gap sequence has no function in replication of pPMP1, maintenance in a bacterial cell, or transfer of the T-DNA region to a plant cell; a first sequence of approximately 1100 bp containing a KmR gene coding sequence from +653 to +1454 and approximately 300 bp of regulatory sequences upstream and downstream of the coding sequence; a second gap sequence of approximately 150 bp; a second sequence containing a ColE1 ori from +1602 to +2269; a third gap sequence of approximately 150 bp; a third sequence of approximately 1500 bp containing aTrfA coding sequence from +3662 to +2517 and approximately 350 bp of regulatory sequences upstream and downstream of the coding sequence; a fourth gap sequence of approximately 450 bp; a fourth sequence containing an RK2 oriV from +4932 to 4303; a fifth gap sequence of 109 bp; a RB at position 5041 to 5066 and a unique EcoRI restriction site at position +5139.

Example 3: Reporter Assays for Visualizing Transient Expression in Tobacco

This example describes various reporter assays for use in plant cells to determine transformation efficiency and expression of a heterologous gene in said plant cells.

Beta-Glucuronidase Assay.

Beta-glucuronidase is used as a reporter and is assayed according to the method described in Jefferson et al., EMBO J, 1987, 6:3901-3907.

Green Fluorescent Protein Assay.

Tobacco plants are co-infiltrated with cells of *Agrobacterium tumefaciens* strain AGL1 containing (i) the suppressor of gene silencing p19, and separately (ii) an improved variant of the green fluorescent protein from the copepod *Pontellina plumate*, commercially available as TurboGFP (Evrogen, USA, catalog no. FP552). Expression of p19 is driven by a double cauliflower mosaic virus 35S promoter. Expression of TurboGFP is driven by a minimal cauliflower mosaic virus 35S promoter and a 5' UTR of cowpea mosaic virus (HT-CPMV). Bacterial concentrations in the infiltration mixture are adjusted to $OD_{600}$=0.16 for each of the two bacterial suspensions, one comprising the coding sequence of TurboGFP and the other the p19 suppressor of gene silencing. Plants for infiltration are grown in the greenhouse in rockwool blocks with 20 hours light period and 4 hours dark period, 26° C./20° C. day/night temperature and 70%/50% relative humidity (day/night). Plants are given fertilizer by sub-irrigation. Plants are infiltrated at 50 mbar for 1 minute following standard infiltration protocols or by syringe infiltration as described in Example 1.

Immediately after vacuum infiltration plants are hang upside down for a couple of minutes on a rack in order to reduce excess infiltration solution remaining of the leaves and then placed on greenhouse benches for the remaining part of the experiment. Fertilizer formulations post-infiltration are kept the same as pre-infiltration and ferti-irrigation is supplied through a drip irrigation system two times a day for 45 seconds. GFP expression in plants is analyzed qualitatively and quantitatively. Qualitative estimations of GFP are performed under blue light (HL32T Hand Lamp, Clare Chemical Research, USA) which emits light within the range of excitation of the TurboGFP (Excitation wavelength=482 nm and emission wavelength=502 nm). Quantitative analysis of GFP in leaves is determined by fluorescence measurement on a Modulus microplate reader (Turner Biosystems) in Fluorescence mode with Blue optical kit ((Excitation wavelength=490 nm and emission wavelength=510-570 nm). At any given harvesting point, leaf disks of approximately 80 mg are collected with a leaf disc puncher from five leaves per plant (fully expanded leaves from positions 1-5, are 0 represents the shoot apical meristem and 1, the first leaf) from three plants per treatment. Samples are flash-frozen in liquid Nitrogen and stored at −80° C. and then ground in a TissueLyser (Qiagen) for approximately 2.5 minutes in the presence of 1 ml of extraction buffer comprising 50 mM Tris, 2 mM DTT, 150 mM NaCl, 1% Triton X-100 and 4 M Urea, pH 7.4. After grinding, samples are centrifuged at full speed for 10 min in a microcentrifuge and 500 μl of supernatant is collected and stored at −20° C. until analysis. Samples from the five leaves of a single plant are pooled by collecting 200 ul of the supernatant from each extract in a single microcentrifuge tube. Pooled extracts are again centrifuged for 10 min at 4° C. and 700 μl of the supernatant is transferred to a fresh tube. For quantification of fluorescence, 5 μl of the supernatant is diluted in 195 μl of extraction buffer and measured in a microplate reader. The concentration of GFP is calculated using a standard curve made with commercial recombinant TurboGFP protein. The standard curve is prepared by adding different amounts of recombinant TurboGFP protein to an extract of a control tobacco plant and diluted 1:40 in extraction buffer.

Example 4: Comparison of *Nicotiana tabacum* Varieties by Transient Expression

This example describes the comparisons of (i) the expression of a monoclonal antibody C5-1 in more than 90 *Nicotiana tabacum* varieties after agroinfiltration and (ii) the phenotypic characteristics of the plants prior to and after infiltration.

*Nicotiana tabacum* Varieties.

Over ninety (>90) *Nicotiana tabacum* varieties as listed in Table 1 are tested with the aim of identifying tobacco lines that are suitable for transient expression of a recombinant protein. Tobacco lines are chosen such that they included the largest possible diversity of tobacco types grown worldwide, including flue cured tobacco, burley, oriental, semi oriental and cigar wrapper tobacco lines. The following tobacco varieties are tested: *N. tabacum* AA 37-1, *N. tabacum* B 13P, *N. tabacum* Xanthi (Mitchell-Mor), *N. tabacum* KTRD#3 Hybrid 107, *N. tabacum* Bel-W3, *N. tabacum* 79-615, *N. tabacum* Samsun Holmes NN, F4 from cross *N. tabacum* BU21 x *N. tabacum* Hoja Parado, line 97, *N. tabacum* KTRDC#2 Hybrid 49, *N. tabacum* KTRDC#4 Hybrid 110, *N. tabacum* Burley 21, *N. tabacum* PM016, *N. tabacum* KTRDC#5 KY 160 SI, *N. tabacum* KTRDC#7 FCA, *N. tabacum* KTRDC#6 TN 86 SI, *N. tabacum* PM021, *N. tabacum* K 149, *N. tabacum* K 326, *N. tabacum* K 346, *N. tabacum* K 358, *N. tabacum* K 394, *N. tabacum* K 399, *N. tabacum* K 730, *N. tabacum* KY 10, *N. tabacum* KY 14, *N. tabacum* KY 160, *N. tabacum* KY 17, *N. tabacum* KY 8959, *N. tabacum* KY 9, *N. tabacum* KY 907, *N. tabacum* MD 609, *N. tabacum* McNair 373, *N. tabacum* NC 2000, *N. tabacum* PG 01, *N. tabacum* PG 04, *N. tabacum* PO1, *N. tabacum* PO2, *N. tabacum* PO3, *N. tabacum* RG 11, *N. tabacum* RG 17, *N. tabacum* RG 8, *N. tabacum* Speight G-28, *N. tabacum* TN 86, *N. tabacum* TN 90, *N. tabacum* VA 509, *N. tabacum* AS44, *N. tabacum* Banket A1, *N. tabacum* Basma Drama B84/31, *N. tabacum* Basma I Zichna ZP4/B, *N. tabacum* Basma Xanthi BX 2A, *N. tabacum* Batek, *N. tabacum* Besuki Jember, *N. tabacum* C104, *N. tabacum* Coker 319, *N. tabacum* Coker 347, *N. tabacum* Criollo Misionero, *N. tabacum* PM092, *N. tabacum* Deicrest, *N. tabacum* Djebel 81, *N. tabacum*. DVH 405, *N. tabacum* Galpão Comum, *N. tabacum* HB04P, *N. tabacum* Hicks Broadleaf, *N. tabacum* Kabakulak Elassona, *N. tabacum* PM102, *N. tabacum* Kutsage E1, *N. tabacum* KY 14xL8, *N. tabacum* KY 171, *N. tabacum* LA BU 21, *N. tabacum* McNair 944, *N. tabacum* NC 2326, *N. tabacum* NC 71, *N. tabacum* NC 297, *N. tabacum* NC 3, *N. tabacum* PVH 03, *N. tabacum* PVH 09, *N. tabacum* PVH 19, *N. tabacum* PVH 2110, *N. tabacum* Red Russian, *N. tabacum* Samsun, *N. tabacum* Saplak, *N. tabacum* Simmaba, *N. tabacum* Talgar 28, *N. tabacum* PM132, *N. tabacum* Wislica, *N. tabacum* Yayaldag, *N. tabacum* NC 4, *N. tabacum* TR Madole, *N. tabacum* Prilep HC-72, *N. tabacum* Prilep P23, *N. tabacum* Prilep PB 156/1, *N. tabacum* Prilep P12-2/1, *N. tabacum* Yaka JK-48, *N. tabacum* Yaka JB 125/3, *N. tabacum* TI-1068, *N. tabacum* KDH-960, *N. tabacum* TI-1070, *N. tabacum* TW136, *N. tabacum* PM204, *N. tabacum* PM205, *N. tabacum* Basma, *N. tabacum* TKF 4028, *N. tabacum* L8, *N. tabacum* TKF 2002, *N. tabacum* TN90, *N. tabacum* GR141, *N. tabacum* Basma xanthi, *N. tabacum* GR149, *N. tabacum* PM216, *N. tabacum* PM217, *N. tabacum* GR153, *N. tabacum* Petit Havana, *N. tabacum* PM215.

Tobacco varieties can be obtained from the *Nicotiana* collection of North Carolina State University, Crop Science Department (Oxford, N.C., USA). For all lines, agronomical (biomass, fertility, homogeneity) and analytical parameters (total soluble protein, total proteases, total alkaloids) are measured. To this end, tobacco plants are grown individually in 12 cm pots under a conventional float bed system in a greenhouse. Agronomical and analytical parameters are measured at harvest. Transient expression studies are performed by syringe co-infiltration of a first and a second *Agrobacterium tumefaciens* suspension. The first *A. tumefaciens* suspension is *A. tumefaciens* AGL1 bacteria harbouring a binary vector comprising the coding sequence of a monoclonal antibody under control of plant regulatory elements. The second *A. tumefaciens* suspension is AGL1 bacteria harbouring the coding sequence of the p19 suppressor of gene silencing of cucumber necrosis virus under control of plant regulatory elements. All infiltration experiments are performed in triplicate in three plants each. One additional plant is kept as a control for each tobacco line.

Gene Constructs.

Gene construct C7 is a pCambia-derived binary vector containing two expression cassettes comprising the heavy and light chain of monoclonal antibody C5-1 under control of the plastocyanin pPC promoter and terminator sequence. Gene construct C32 is a pKYLX7 derived binary vector containing an expression cassette comprising the p19 suppressor of gene silencing of cucumber necrosis virus (CNV) under control of the cauliflower mosaic virus 35S promoter and terminator. All binary vectors are in *Agrobacterium tumefaciens* strain AGL1.

Transient Expression of C5-1 Monoclonal Antibody.

Tobacco plants are grown individually in a 12 cm pot in the greenhouse. Three plants of each tobacco variety are infiltrated with a bacterial suspension using a syringe as described in Example 1. At 6 days post infiltration, all infiltrated leaves from one plant are collected in a heat-sealable bag, frozen to −80° C. and then ground to a fine powder and fully homogenized. Of each plant, total soluble proteins are extracted from approximately 1 g frozen weight of ground leaf powder in 3 ml extraction buffer. The extraction buffer is 50 mM Tris (pH 7.4), 150 mM NaCl, 0.1% Triton X-100, 4M Urea and 2 mM DTT. As a reference, an identical extract is prepared of *Nicotiana benthamiana* plants infiltrated at the same time with the same *Agrobacterium* suspensions. For analysis of expression of C5-1, plant extracts are diluted 200-fold and serial dilutions are spotted on a nitrocellulose membrane using the Easy-titer ELIFA dot-blot immunoassay system (Pierce). Nitrocellulose membranes are incubated with a HRP-labelled antibody from Jackson ImmunoResearch (cat. No. #115-0.5-205) at a 1:5,000 dilution. Signals on the membranes are analysed visually and a score is given to each plant based on the visual interpretation of the signal intensity in comparison with that of serial dilutions of the reference *N. benthamiana* extract. Scoring is as follows:

+=spot detectable but below 25% of signal of reference sample,

++=between 25 and 50% of signal of reference sample,

+++=between 50 and 100% of signal of reference sample.

Results.

No signal is detected in control plants and out of the 90 varieties tested, 26 varieties show reasonable expression and have a ++ score. 64 varieties do not show any or had only little expression. A list of the 26 varieties showing expression of monoclonal antibody C5-1 is presented in Table 2.

Example 5: Effect of Suppressors of Gene Silencing on Transient Expression of Green Fluorescent Protein in *N. tabacum*

In this example a comparison of the effect of various suppressors of gene silencing on the expression of a reporter gene construct in a number of tobacco varieties using agroinfiltration, is described. Also described is the effect of (i) the promoter driving the expression of the suppressor of gene silencing and (ii) the ratio of target protein to suppressor of gene silencing.

Reporter and Suppressor of Gene Silencing Constructs.

The green fluorescent protein gene is the TurboGFP (tGFP) gene of Evrogen (see Example 3). The TurboGFP gene is cloned under the control of the cauliflower mosaic virus 35S promoter and HT-CPMV sequence and the NOS terminator sequence in pBINPLUS resulting in gene construct pC91. The following suppressors of gene silencing are tested: the p19 protein of cucumber necrotic virus (CNV), the p1 protein of rice yellow mottle virus (RYMV), the p25 protein of potato virus X (PVX), the AC2 protein of African cassava mosaic virus (ACMV), the 2b protein of cucumber mosaic virus (CMV) and the helper-component proteinase (HcPro) of tobacco etch virus (TEV). Suppressors of gene silencing p1 of RYMV, p25 of PVX, AC2 of ACMV, 2b of CMV, HcPro of PVY and p19 of CNV are blunt-end cloned in the SmaI site of pBIN61 (Bendahmane et al., Plant J, 2000, 21:73-81) in sense orientation under the control of the cauliflower mosaic virus 35S promoter and terminator sequence to generate gene constructs pC18, pC19, pC20, pC21, pC120 and pC32, respectively. All sequences are public available Promoter Gene Constructs.

To test the effect of various promoters driving expression of a suppressor of gene silencing, p19 of CNV as present in gene construct pC32 under control of the cauliflower mosaic virus 35S promoter and terminator, is also placed under (i) the control of the nopaline synthase pNOS promoter (gene construct pC224) and (ii) the *Medicago sativa* cultivar WL357HQ plastocyanin promoter pPC (GenBank EF628506.1) resulting in a pBIN61-related gene construct pC226.

Plant Material.

*N. benthamiana* and *N. tabacum* PM67, PM81, PM92, PM128, PM132, PM133 and PM204 plants are grown in the greenhouse as described in Example 4.

Infiltration and Analysis of Expression.

Six and seven week old plants are infiltrated by vacuum infiltration as described in Example 1. All gene constructs are in *A. tumefaciens* strain AGL1. A18 is AGL1(pC18), A19 is AGL1(pC19), A20 is AGL1(pC20), A21 is AGL1(pC21), A32 is AGL1(pC32), A120 is AGL1(pC120), A224 is AGL1 (pC224), A226 is AGL1(pC226) and A91 is AGL1(pC91). Analysis of expression of the green fluorescent protein is as described in Example 3.

Results of Testing Various *N. tabacum* Varieties and Suppressors of Gene Silencing.

Figure 2:
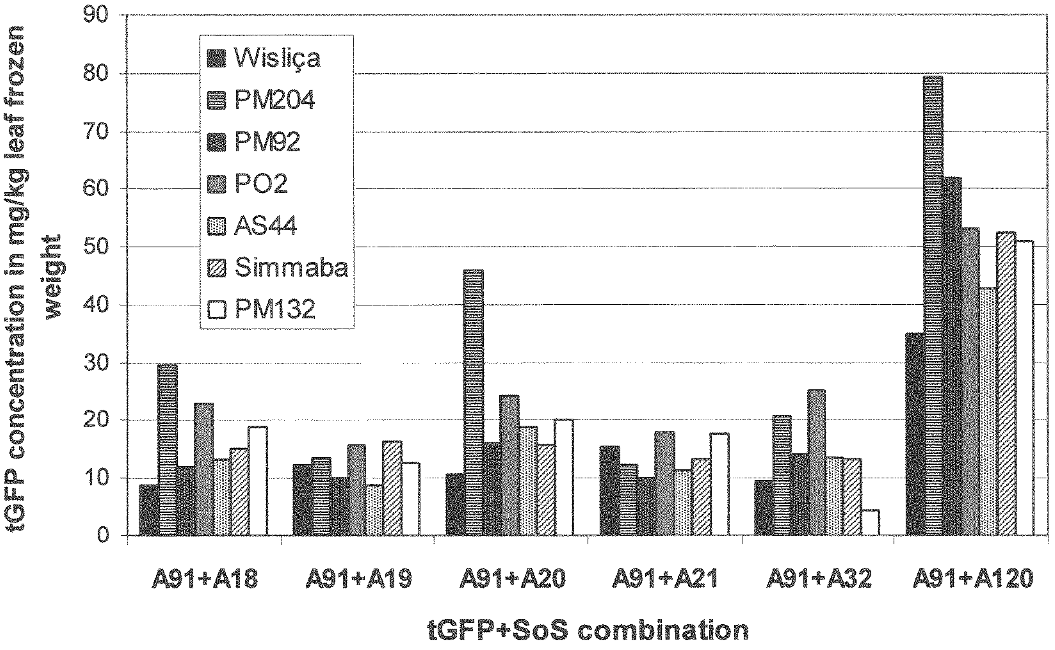

The efficiency of the various suppressors of gene silencing to enhance tGFP expression in tobacco is compared to that in *N. benthamiana* plants. Two varieties, PM92 and *N. tabacum* Wisliça displayed a more pronounced necrosis and chlorosis. None of the suppressors of gene silencing caused visible stress symptoms in *N. benthamiana*. Expression of tGFP in *N. benthamiana* is checked under blue light at 6 DPI and best results are obtained with plants co-transfected with the pC120 gene construct that produced a very strong GFP fluorescence signal. tGFP fluorescence in *N. tabacum* leaves is highest when tobacco plants of all seven varieties tested are co-transfected with the HcPro suppressor of gene silencing as in pC120 (FIG. 2). Reasonable expression is also found when *N. tabacum* PM204 is co-infiltrated with the p1 suppressor of gene silencing of RYMV (pC18 in A18; FIG. 2) and the AC2 suppressor of gene silencing of ACMV (pC20 in A20; FIG. 2). Best results are obtained for *N. tabacum* PM204 for three of the suppressors of gene silencing tested and highest expression is found when co-infiltrated with HcPro (pC120), followed by AC2 (pC20) and p1 (pC18).

Results of Testing *N. tabacum* PM132 and 204 and Suppressors of Gene Silencing.

The effects of the HcPro of TEV, AC2 of ACMV and p19 of CNV suppressors of gene silencing on tGFP expression in PM132 and PM204 is tested in 6 weeks old plants. In addition, the effects of three different plant expressible promoters driving the p19 suppressor of gene silencing of CNV is tested. The following promoters are tested: the cauliflower mosaic virus 35S promoter and terminator in pC32, the nopaline synthase promoter and terminator in pC224 and the pPC plastocyanin promoter and terminator in pC226. Quantification of tGFP expression levels at 6 days post-infiltration showed that high expression is obtained only when the HcPro suppressor of silencing is used in combination with A91 harbouring the tGFP gene construct. Expression levels in PM132 and PM204 are more than 3 times higher than those obtained for the other suppressors of gene silencing. Remarkably, up to a 10-fold increase in tGFP expression levels in PM132 and PM204 is observed when 6 week-old tobacco plants are infiltrated compared to 7 week-old plant.

Example 6: Comparison of Biomass Productivity, Alkaloid, Total Soluble Protein and Total Proteinase Activity of Tobacco Varieties This example provides a comparison of the biomass productivity, total soluble protein contents, proteinase content and alkaloid content of a number of *N. tabacum* varieties.

Plant Material.

All tobacco varieties listed in Table 1 and described in Example 5 are grown in 288 cell Styrofoam trays (0.25 $m^2$/tray) using a conventional float bed system. Tobacco varieties are grown in two replicates using a randomized block design in the greenhouse. Leaves are harvested at various stages to determine total soluble protein content, total protease and alkaloid content of leaves. Leaves of greenhouse grown tobacco plants are collected in the greenhouse, quickly frozen in liquid nitrogen and ground to a fine powder which is transferred to 50 ml tubes and stored at −80° C. until assays are performed.

Extraction of Leaf Material for Enzyme Assay.

Ground tobacco leaf powder is mixed with four volumes of extraction buffer containing 50 mM potassium phosphate, buffered with NaOH to pH 7.5, 1% insoluble PVP and 0.1% β-mercaptoethanol. Homogenates are centrifuged for 10 minutes at 1,200 g and the supernatant is used to determine protease enzyme activity and for the determination of total soluble protein content.

Enzyme Assay.

Azocoll-digesting activity (azocollase) is determined by measuring the release of the red dye from Azocoll (Calbiochem) as described by Ragster and Chrispeels, Plant Physiology, 1979, 64: 857-862. Twenty mg Azocoll substrate is mixed with 50-100 μl of enzyme extract in 25 mM Tris-HCl, pH 9.0 buffer in a total volume of 2 ml and incubated in a water bath at 37° C. for 15 minutes. The reaction is terminated by cooling the tubes to 2° C. for 15 min and then centrifuged at 2,000 g for 10 minutes. The supernatant is placed in the spectrophotometer and the extinction is measured at 520 nm.

Determination of Alkaloids.

0.1 g of ground tobacco leaf powder is transferred into a glass vial and 0.5 ml sodium hydroxide solution (2N NaOH) is added. After 15 minutes, 5 ml of a methyl-tert butyl ether solution containing 0.4 mg/ml quinoline is added and the sample is shaked for 2.5 hours. The top layer of fluid is transferred to a fresh glass scintillation vial and loaded onto a Perkin Elmer Autosystem XL Gas Chromatograph autosampler for measurement. The amount of alkaloid is measured as described by Chen et al., Beitrage zur Tabakforschung International, 2005, 21: 369-379.

Total Soluble Protein.

Total soluble protein (TSP) content in leaf extracts is determined using Coomassie-Plus Assay reagent (Pierce) by absorbance measurement on a microplate reader at 595 nm as described in Bradford, Analytical Biochemistry, 1976, 72: 248-254. Extracts are diluted 1:10 in ultrapure water and 10 μL is loaded in triplicate on a flat-bottom microplate.

Results.

The protease activity of extract of Coker 347, PM132, PM092, PM204, PM102 and Saplak was 145.6, 118.4, 116.6, 109.8, 39.7 and 15.1, respectively. Leaf biomass productivity in g/sq m of F4 (BU21 x Hoja Parado)/97, PM102, PM132, PM204, PM092 was 400938, 318306, 190506, 187442 and 187422, respectively. The alkaloid content of PM016, PM021, PM092, PM102, PM132 and PM204 in mg/g leaf tissue is 3.57, 1.79, 0.41, 3.2, 0.79 and 0.66 respectively. The protein content of extracts of PM016, PM021, PM092, PM102, PM132 and PM204 in μg/mL extract is 525, 374, 317, 288, 261 and 311 respectively.

Example 7: Effect of *Agrobacterium* Strains on Transient Expression

In this example, the effect of using six different *Agrobacterium tumefaciens* strains for agroinfiltration of tobacco varieties, on the expression of a target protein is described.

*Agrobacterium* Strains and Binary Vectors.

To test the effect of *Agrobacterium* strains on transient expression, tobacco plants are vacuum-infiltrated as described in Example 1 with *A. tumefaciens* strains AGL1, EHA105, GV2260, GV3101, Cry5 and LBA4404 each harbouring the gene construct pC91. pC91 contained a tGFP gene under control of the cauliflower mosaic virus 35S promoter and HT-CPMV leader sequence and a nopaline synthase terminator sequence in a pBINPLUS binary vector. All are co-infiltrated with AGL1 harbouring pC120 which comprises the expressible sequence of HcPro. A91 is AGL1 (pC91), E91 is EHA105(pC91), G91 is GV2260(pC91), L91 is LBA4404(pC91), V91 is GV3101(pC91), Y91 is Chry5 (pC91) and A120 is AGL1(pC120).

Preparation of Inoculum.

*Agrobacterium* cultures are grown in LB Miller MES pH 5.6, supplemented with appropriate antibiotics, to a final optical density ($OD_{600}$) of >2.0. Bacteria are harvested by centrifugation and resuspended in infiltration solution (10 mM MgCl2, 5 mM MES, pH5.6). In each experiment, an *Agrobacterium* suspension harboring construct pC91 is mixed in equal volumes with an *Agrobacterium* suspension carrying the gene for a suppressor of silencing to generate a 6× concentrated inoculum. On the day of infiltration, the concentrated inoculum is diluted to 1× final concentration (corresponding to an $OD_{600}$ of about 0.3) in infiltration solution and equilibrated to room temperature.

Plant Material.

*N. tabacum* Burly 21, PM6, PM21, K149, PO1, PO2, PM92, Simmaba, PM132, Wisliça, Yaka JB 125/3 and PM204 plants are grown in the greenhouse in 12 cm pots under a photoperiod regime of 20 hour light and 4 hour dark, in a temperature of 26° C./20° C. day/night and a relative humidity of 70%/50% day/night.

Infiltration of Plants.

Plants are infiltrated under vacuum as described in Example 1. Artificial lighting (80-100 μmol photon/cm$^2$) is kept on during the whole infiltration process to ensure consistent light conditions. Following infiltration, plants are placed back in the greenhouse until harvesting. Apparition of stress symptoms such as chlorosis (leaf yellowing) and necrotic lesions ("dead" spots) are monitored visually by comparing infiltrated plants to the non-infiltrated controls. Growth conditions such as fertilization, photoperiod and temperature are the same as used before infiltration but now water and fertilizer are administered to plants using a drip irrigation system. Four to six days after infiltration, plants are placed under blue light and all infiltrated leaves showing fluorescence are collected, placed in a zip-bag and stored at −80° C. until processed for analysis.

Turbo GFP Imaging and Quantitation.

Accumulation of tGFP in the harvested leaves is monitored under blue light in a dark chamber. Harvested leaves are homogenized to a fine powder under dry ice and samples of 1.00 g+/−0.05 g frozen weight of powder are extracted in 3 ml extraction buffer (50 mM Tris base; 100 mM NaCl; EDTA 1 mM; 0.2% Triton X-100; pH 7.5) by two steps of vortexing for 20 seconds, followed by centrifugation at 20,000 g for 15 min. Soluble extracts are kept on ice for analysis. *N. tabacum* extracts are diluted 1:50 in extraction buffer and 200 uL are loaded in triplicate on a black 96-well plate (Corning). TurboGFP concentration in the extracts is determined by fluorescence measurement on a Modulus microplate reader (Turner Biosystems) with Blue optical kit (Excitation wavelength: 490 nm/Emission wavelength: 510-570 nm). Samples fluorescence is corrected by subtracting auto-fluorescence of extracts of non-infiltrated control plants. A standard curve is prepared by adding TurboGFP control protein (rTurbo GFP, Evrogen #FP552) in a concentration range of 4000 to 125 ng/ml to a non-infiltrated extract diluted 1:50 final in extraction buffer.

Results.

Figure 3A:
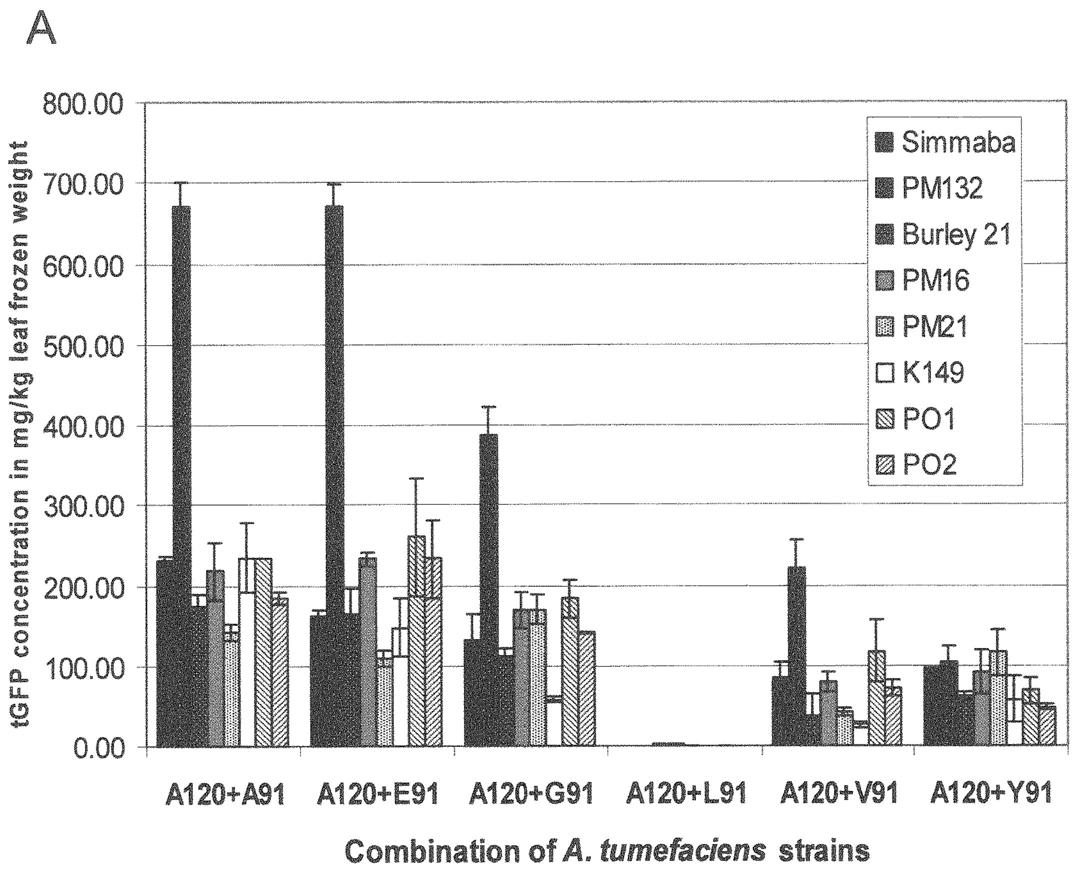
Figure 3B:
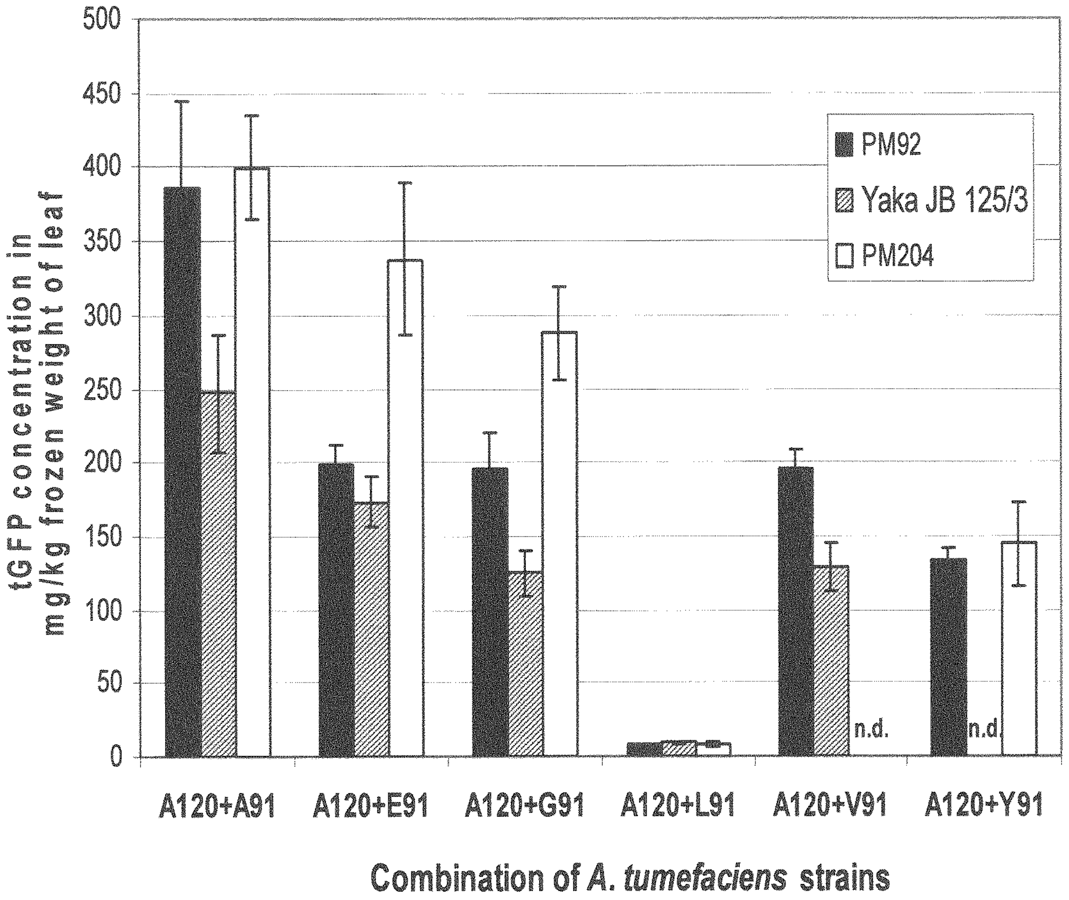

Plants are infiltrated in two batches. First, *N. tabacum* Burley 21, PM016, PM21, K149, PO1, PO2, Simmaba and PM132 are infiltrated and analysed for expression of tGFP. Six days after infiltration it could be observed that *Agrobacterium* strains Cry5 and GV2260 caused severe stress responses including chlorosis and necrotic lesions on leaves of the majority of tobacco varieties tested. In addition, tobacco varieties PM016, PM21 and K149 appeared to be highly sensitive to agroinfiltration and strong necrosis is observed with many of the strains tested. Highest expression for all strains tested is consistently with PM132 (FIG. 3A). Surprisingly, more than two-fold higher expression is obtained for *Agrobacterium* strains AGL1 and EHA105 harbouring the pC91 gene construct reaching approximately 700 mg tGFP/kg frozen leaf weight compared to 400 mg tGFP/kg frozen leaf weight for GV2260, 200 mg tGFP/kg frozen leaf weight for GV3101 and less than 100 mg tGFP/kg frozen leaf weight for Cry-5 and LBA4404. The tobacco varieties Burley 21, PM016, PM21, K149, PO1, PO2, and Simmaba produced far less tGFP varying from zero to approximately 200 mg tGFP/kg frozen leaf weight maximum depending on the *Agrobacterium* strain used. The tobacco varieties PM92 and PM204 produced up to 400 mg tGFP/kg frozen leaf weight when using AGL1 to deliver both gene constructs. Remarkably, PM204 also produces up to 400 mg tGFP/kg frozen leaf weight when using EHA105 but the other tobacco varieties PM92 and PM181 produce only half this amount using the same bacterium for delivery (FIG. 3B).

Conclusion

The combination consisting of *A. tumefaciens* AGL1 or EHA105 carrying the construct of interest (represented by a tGFP reporter gene in a HT-CPMV-based expression cassette) and AGL1 carrying the suppressor of silencing (HcPro) led to the highest accumulation of tGFP in this experiment. The two tobacco varieties PM132 and PM204 are the ones that accumulated the highest levels of tGFP and PM132 is tested further for the recombinant production of influenza haemagglutinin H5 polypeptide (see Example 8).

Example 8: Transient Expression of Haemagglutinin H5 in *N. tabacum*

In this example, the transient expression of haemagglutinin H5 in a *N. tabacum* variety using agroinfiltration is described.

*Agrobacterium* Strains, Gene Constructs and Plants.

Gene construct pC71 is a pBIN61-derived binary vector comprising a coding sequence of haemagglutinin 5 (H5) gene of influenza H5N1 strain placed under the control of a minimal cauliflower mosaic virus 35S promoter and 5' UTR of HT-CPMV, and at the 3' end the nopaline synthase terminator and 3' UTR of HT-CPMV. pC120 is co-infiltrated as described above to provide Hc-Pro suppressor of gene silencing. Both pC71 and pC120 are present in the same AGL1 strain. Fourteen PM132 plants are grown and infiltrated with AGL1(pC71) and AGL1(pC120) as described before in Example 7.

Extraction and Western Analysis.

All leaves are harvested, frozen to −80° C., ground to a powder and homogenized as described previously. Detection of recombinantly produced H5 protein is by western blot using crude extracts of infiltrated *N. tabacum* PM132 and control *N. benthamiana* plants infiltrated with the same agrobacteria and transiently expressing H5 protein. FIG. 4 shows the results of Western analysis of crude extracts and a band of the expected molecular weight for H5 (75 kDa). From FIG. 4 it is also apparent that the intensity of H5 is comparable for extracts of *N. tabacum* PM132 and *N. benthamiana*. No band at 75 kDa is detected in the non-infiltrated wild-type controls.

Haemagglutinin Activity of Extracts.

Haemagglutinin has the ability to bind to monosaccharide sialic acid which is present on the surface of erythrocytes in red blood cells. Haemagglutination can be used to determine the relative activity of a haemagglutinin protein and is used to determine the biological activity of recombinant H5 present in crude extracts of *N. tabacum* PM132 and *N. benthamiana* transiently expressing H5 as described before. 1.5-fold serial dilutions of plant extract are prepared and mixed in a 96-well microplate with red blood cells. Red blood cells that are not bound to haemagglutinin will sediment and settle to form a tight button. Red blood cells that are bound to haemagglutinin form a lattice that coats the well. Only correctly assembled homo-trimeric haemagglutinin will bind erythrocytes. A haemagglutination assay performed on extracts of aforementioned tobacco plants transiently expressing an H5 protein showed that extracts of PM132 had haemagglutinating activity indicating that correctly-folded trimeric H5 is produced in vacuum-infiltrated *N. tabacum* PM132.

Example 9: Transient Expression of Rituximab Monoclonal Antibody

Construction of Rituximab Monoclonal Antibody Expression Vectors.

Rituxumab is a murine/human chimeric monoclonal IgG1 antibody that binds human CD20. Rituximab is used in the treatment of many lymphomas, leukemias, transplant rejection and some autoimmune disorders. An expression cassette comprising the full coding sequences of the rituximab monoclonal antibody light and heavy chain as in CAS registry number 174722-31-7 or WO02/060955 is made by chemical synthesis with codons optimized for expression in a tobacco plant cell.

```
>rituximab mature heavy chain (tobacco optimized)
sequence as in C148
                                      (SEQ ID NO: 18)
caagttcaacttcaacaaccaggtgctgaacttgttaagcctggtgctt

ctgttaagatgtcttgcaaggcttctggatacactttcacatcctacaa

catgcattgggttaagcaaactccaggacgtggacttgaatggattgga

gatatctaccctggaaacggtgatacttcctacaaccagaagttcaagg

gaaaggctactcttactgctgataagtcctcttccactgcttacatgca

actttcttcactcacttccgaggattctgctgtttattactgcgctagg

tccacttattatggtggagattggtacttcaatgtttggggagctggaa

ctactgttactgtgtctgctgcttctactaagggaccatctgtttttcc

acttgctccatcttctaagtctacttccggtggaactgctgctcttgga

tgccttgtgaaggattatttcccagagccagtgactgtttcttggaact

ctggtgctcttacttctggtgttcacactttcccagctgttcttcagtc

atctggactttactccctttcttctgttgttactgtgccatcttcttca

cttggaactcagacttacatctgcaacgttaaccacaagccatctaaca

caaaagtggataagaaggcagagccaaagtcttgtgataagactcatac

ttgtccaccatgtccagctccagaacttcttggtggtccatctgttttc

ttgttcccaccaaagccaaaggatactctcatgatctctaggactccag

aagttacttgcgttgttgtggatgtttctcatgaggacccagaggttaa

gttcaactggtacgtggatggtgttgaagttcacaacgctaagactaag

ccaagataggaacagtacaactctacttaccgtgttgtgtctgtgctta

ctgttcttcaccaggattggcttaacggaaaagagtacaaatgcaaggt

ttccaataaggctttgccagctccaattgaaaagactatctccaaggca

aaaggacagcctagagagccacaggtttacactcttccaccatatagag

atgagcttactaagaaccaggtttcccttacttgtcttgtgaagggatt

ctacccatctgatattgctgttgagtgggagtcaaacggacagcctgag

aacaactacaagactactccaccagtgcttgattctgatggttccttct
```

-continued tcctctactccaaactcactgtggataagtctagatggcagcagggaaa tgttttctcttgctccgttatgcatgaggctctccataatcactacact cagaagtccctttctttgtctcctggaaagtga (SEQ ID NO: 19)

qvqlqqpgaelvkpgasvkmsckasgytftsynmhwvkqtpgrglewig aiypgngdtsynqkfkgkatltadksssstaymqlssltsedsavyycar styyggdwyfnvwgagttvtvsaastkgpsvfplapsskstsggtaalg clvkdyfpepvtvswnsgaltsgvhtfpavlqssglyslssvvtvpsss lgtqtyicnvnfikpsntkvdkkaepkscdkthtcppcpapellggpsv flfppkpkdtlmisrtpevtcvvvdvshedpevkfnwyvdgvevhnakt kpr*eqynstyrvvsvltvlhqdwlngkeykckvsnkalpapiektisk akgqprepqvytlppsrdeltknqvsltclvkgfypsdiavewesngqp ennykttppvldsdgsfflyskltvdksrwqqgnvfscsvmhealhnhy tqkslslspgk*

The mature heavy chain sequence is synthesized with a patatin signal peptide and placed under control of the HT-CPMV promoter and HT-CPMV untranslated 5' and 3' UTR sequences as in patent WO09/087,391 and cauliflower mosaic virus 35S terminator sequence.

SEQ ID NO: 16: atggccactactaaatcttttttaattttatttttatgatattagcaactactagttcaacatgtgct is an example of a nucleotide sequence that encodes the patatin signal peptide which is inserted at the 5' end of the immunoglobulin heavy chain coding sequence in pC148.

The light chain with patatin signal peptide is placed under control of a plastocyanin promoter and terminator sequence as in patent WO01/25455.

>rituximab mature light chain (tobacco optimized) sequence as in C148

(SEQ ID NO: 20)

cagattgtgctttctcagtctccagctattctttctgcttccccaggt gaaaaggttacaatgacttgccgtgcttcttcttctgtgtcctacatt cattggttccaacagaagccaggatcttctccaaagccatggatctac gctacttctaaccttgcttctggtgttccagttaggttttctggatct ggatctggtacttcttactcccttactatttctagagtggaggctgaa gatgctgctacttactactgccaacagtggacttctaatccaccaact ttcggaggtggaactaagcttgagatcaagaggactgttgctgctcca tctgtgtttatttttcccaccatctgatgagcaacttaagtctggaact gcttctgttgtgtgccttctcaacaatttctacccaagggaagctaag gttcagtggaaagtggataatgctctccagtctggaaattctcaagag tctgtgactgagcaggattctaaggattccacttactccatttcttct actcttactctctccaaggctgattatgagaagcacaaggtttacgct tgcgaagttactcatcagggactttcttcaccagtgacaaagtccttc aaccgtggagagtgttga (SEQ ID NO: 21)

QIVLSQSPAILSASPGEKVTMTCRASSSVSYIHWFQQKPGSSPKPWIY

ATSNLASGVPVRFSGSGSGTSYSLTISRVEAEDAATYYCQQWTSNPPT

-continued

FGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC*

The 5' end of the immunoglobulin light chain coding sequence in pC148 is linked to a nucleotide sequence of SEQ ID NO: 17 that encodes the patatin signal peptide, wherein codon usage has been optimized for expression in tobacco. atggccactactaagtccttcttatcctcttcttcatgatccttgctactacttcttctacatgtgct (SEQ ID NO: 17)

Both expression cassettes are cloned in the T-DNA part of pC100 as described in Example 2 to generate pC148. pCambia-2300 (GenBank: AF234315.1; Hajdukiewicz et al., 1994. Plant. Mol. Biol. 25: 989-994) is amplified by PCR using primers PC201F (5'-AGAAGGCCTTCCGGGACGGCGTCAG-3'; SEQ ID NO: 6) and PC202R (5'-ATGGCGCGCCCCCCTCGGGATCA-3'; SEQ ID NO: 7) resulting in unique StuI and AscI restriction endonuclease cleavage sites. The pCambia-2300 fragment is ligated to the StuI/AscI fragment of pC148 comprising the rituximab expression cassette to generate pCambia-Rituximab.

The invention contemplates vectors according to any one of the preceding embodiments and as described above comprising, in the T-DNA region and operably linked to a plant regulatory element, a nucleotide sequence encoding the mature heavy chain of an immunoglobulin that binds human CD20 exhibiting at least 90%, 92%, 94%, 96%, 98%, 99% or 99.5% sequence identity to SEQ ID NO: 18.

The invention also contemplates vectors according to any one of the preceding embodiments and as described above comprising, in the T-DNA region and operably linked to a plant regulatory element, a nucleotide sequence encoding the mature light chain of an immunoglobulin that binds human CD20 exhibiting at least 90%, 92%, 94%, 96%, 98%, 99% or 99.5% sequence identity to SEQ ID NO: 20.

Infiltration of *Nicotiana benthamiana* Plants.

All binary vectors used in this study are introduced in *Agrobacterium tumefaciens* AGL1. Bacteria are grown in YEB-medium comprising 2 g/L Beef extract, 0.4 g/L Yeast extract, 2 g/L Bacto-Peptone, 2 g/L Sucrose, 0.1 g/L MgSO4 and proper antibiotics for selection of the respective *Agrobacterium* strain and binary vector, in an Erlenmeyer flask at 28° C. and 250 rpm on a rotary shaker up to an OD600>1.6. The culture is then diluted 1:100 in fresh LB Broth Miller medium containing 10 mM MES and suitable antibiotics and further grown at 28° C. and 250 rpm on a rotary shaker up to an OD600>2. After growth, bacteria are collected by centrifugation at 8,000 g and 4° C. for 15 min. Pelleted bacteria are resuspended in infiltration solution to $OD_{600}$>2. Four weeks old *Nicotiana benthamiana* plants are co-infiltrated with cells of *Agrobacterium tumefaciens* strain AGL1, one containing (i) an expressible tomato bushy stunt virus (TBSV) p19 suppressor of gene silencing (Swiss-Prot P50625); and the other (ii) pC148 or pCambia-Rituximab, at 1:1 ratio and a final $OD_{600}$=0.3. The coding sequence for the TBSV p19 suppressor of gene silencing is under control of a double cauliflower mosaic virus 35S promoter and terminator sequence in pBin19 (Bevan M W (1984) Nucleic Acids Res. 12: 8711-8721). Vacuum infiltration, harvesting and material sampling are carried out as described in Example 1 except the extraction buffer contains 50 mM Tris (pH 7.4), 150 mM NaCl, 0.1% Triton X-100, 4M Urea and 2 mM DTT. The expression of rituximab monoclonal antibody is quantified in the soluble extracts by ELISA. Microtiter plates (Immulon 2HB, Thermofisher) are coated overnight at 4° C. with a capture antibody (Goat anti-mouse IgG1 heavy chain specific Sigma, #M8770) at a concentration of 2.5 μg/ml. A standard curve (4-80 ng/ml) is prepared using mouse IgG1 control protein (Bethyl, #MI10-102) in mock extract (prepared from leaf material infiltrated only with the p19 suppressor of gene silencing bacterial suspension). Soluble extracts are diluted 1:1000 in dilution buffer (50 mM Tris pH 7.4, 150 mM NaCl, 0.1% Triton X-100) and standards and samples are loaded in triplicate and incubated for 1 hour at 37° C. The antibody for detection is a peroxidase-conjugated goat anti-mouse IgG Fc-specific from Jackson ImmunoResearch (#115-035-205) which is used at a dilution of 1:40,000 and incubated for 1 hour at 37° C. Total soluble protein in the extracts is determined using the Coomassie-Plus Assay reagent from Pierce (#24236). Results of six experiments for each of the combinations, pC148 with p19 suppressor of gene silencing and pCambia-Rituximab with p19 suppressor of gene silencing, indicate that the average expression of rituximab in *Nicotiana benthamiana* leaves is 136,30 mg/kg fresh weight (FW) leaves for pC148 compared to 122,60 mg/kg FW for pCambia-Rituximab.

Example 10: Transient Expression of Influenza H5 Virus-Like Particle in Tobacco

Gene Constructs.

The gene coding for the HcPro suppressor of gene silencing of tobacco etch virus (TEV) isolate TEV7DA (GenBank: DQ986288.1) is cloned in the unique EcoRI site of pC100 to generate pC120. The coding sequence is under the control of a double cauliflower mosaic virus 35S promoter, the 5' untranslated region of TEV7DA and the nopaline synthase terminator sequence, Segment 4 of haemagglutinin H5N1 virus (GenBank: EF541394.1) comprising the coding sequence for the mature haemagglutinin H5, is cloned under control of a minimal cauliflower mosaic virus 35 promoter, 5'- and 3'-untranslated regions of HT-CPMV and the nopaline synthase terminator sequence in the unique EcoRI site of pPMP1 (see Example 2) resulting in pC229.

Infiltration of *Nicotiana tabacum* Plants and Sample Preparation.

All gene constructs are introduced in *Agrobacterium tumefaciens* AGL1. *Nicotiana tabacum* plants are grown in the greenhouse in rockwool blocks with 20 hours light period, 4 hours might period, 26° C./20° C. day/night temperature and 70%/50% day/night relative humidity. Bacteria are grown as described in Example 9 to a final OD600 of 3.5. *Agrobacterium* cultures containing the pC229 gene construct and pC120 suppressor of gene silencing construct are mixed at a 3:1 ratio and diluted to a OD600=0.8 in infiltration solution. Plants are infiltrated by decreasing air pressure to 900 mbar below atmospheric pressure within 15 s, a 60 s holding time followed by a return to atmospheric pressure in approximately 2 s. Leaves of infiltrated plants are collected from 10 plants at 5 days post infiltration and homogenized using a screw press (Green Star Corrupad, GS 1000, Korea Co.). Sodium metabisulphite is added to 10 mM final concentration to reduce sample oxidation. The pH of the extract is adjusted to pH 5.3 and subsequently incubated at room temperature for 20-30 min without stirring. Celpure P300 (Sigma-Aldrich)(10%) is then added to the extract and mixed for 1 minute. The solution is filtrated through a Whatman filter paper pre-coated with Celpure P300 (10% Celpure P300 slurry in 10 mM sodium metabisulphite). For ultracentrifugation, three sucrose cushions are prepared in ultracentrifuge tubes as follows: 1) 3 ml of 80% sucrose; 2) 1.5 ml each of 60 and 45% sucrose; and 3) 1 ml each of 60, 45 and 35% sucrose. Clarified and filtered extract samples (up to 13 ml) are gently placed on top of the sucrose gradients and subjected to ultracentrifugation in a swinging bucket type rotor (Sorvall Surespin 630; Kendro) at 24,000 rpm for 1 hour at 4° C. (135,000 RCFmax). Sucrose concentrated samples are pre-filtered using a 0.45 μm filter and subjected to size exclusion chromatography (SEC) under isocratic conditions on an automated AKTA chromatography system. The running buffer is TBS, pH 7.5 and sample size is 4 ml under a flow rate of 1 ml/min on a HiLoad 16/60 Superdex 200 column (GE Healthcare, 17-1069-01). Fractions containing purified H5 are pooled and concentrated to about 0.3 mg/ml using a 30 kDa cut-off Centricon ultrafiltration membrane device (Millipore) and further analysed.

Gel Electrophoresis and Western Blotting.

Samples of pooled fractions are subjected to SDS-PAGE, western blotting and Blue Native-PAGE using standard techniques. SDS-PAGE is on a 4-12% SDS-PAGE gel. As a control (Ctrl+) commercially available recombinant H5 (Immune Technology Corp., New York, cat. #IT-003-0052p) is used. After separation, proteins are stained with Imperial M protein stain (Pierce #24615). For Western blotting, the primary antibody is a rabbit anti-HA antibody (H5N1 VN1203/04 #IT 003-005V, Immune Technology Corp., New York). For detection, an HRP-labelled affiniPure goat-anti-rabbit IgG FC-fragment is used (Jackson Laboratories, #111-035-046). Detection is done by chemiluminescence using an Immuno-star HRP Chemiluminescent Kit (BIO-RAD Laboratory, 170-5040). Results are captured using Chimio-Capt 3000 and show the presence of H5 in extracts of plants infiltrated with the pC229 gene construct. The molecular weight is similar to that of commercial recombinant H5. Native-PAGE is performed on 4-16% Bis-Tris pre-cast polyacrylamide gels (Novex, Invitrogen, USA). For loading, samples are treated with digitonin in native polyacrylamide gel electrophoresis (PAGE) sample buffer and incubated for 1 h at 4° C. Subsequently, Native-PAGE G-250 sample additive (Novex, Invitrogen, USA) is added to a final concentration of 0.5% and samples are loaded and run on a 4-16% Bis-Tris PAGE gel. Gels are run at 4° C. at 150V constant for the first 60 min. Subsequently, voltage is increased to 250V for another 30 min and gels are stained with Imperial M protein stain. Results of native-PAGE and Western blotting show the successful expression of H5 following transient expression in tobacco.

Haemagglutination.

Natural trimeric haemagglutinin (HA), such as the H5 protein, has the ability to bind to the monosaccharide sialic acid, which is present on the surface of erythrocytes (red blood cells). This property known as hemagglutination is the basis of a rapid assay and is used here to determine the biological activity of the recombinant protein. Haemagglutinating activity of tobacco-produced H5 is measured by incubating 1.5-fold serial dilutions of the plant extract as well as extract purified by size-exclusion chromatography in a 96-well plate with a specific amount of red blood cells. Red blood cells not bound to H5 sink to the bottom of a well and form a precipitate. It is important to note that only H5 correctly assembled as homo-trimer will bind erythrocytes. Haemagglutinating activity is observed in extracts of tobacco plants infiltrated with the pC229 gene construct, as well as fractions of pC229 enriched by size exclusion chromatography.

Example 11: Optimization of Inoculum Density for Tobacco Transfection

The following experiments describe optimization of the methods of the invention. Three factors are analyzed: (i) the final concentration of bacteria in the inoculum (ranging from 0.05 to 0.85), (ii) the ratio of construct of interest (COI) and suppressor silencing SoS, that is COI:SoS (ranging from 3.00 to 0.33); (iii) and the tobacco varieties used in expression (*N. tabacum* Burley 21, PM132 and PM204). The level of TurboGFP expression in infiltrated leaves are measured at 6 days post infiltration (DPI). The experiment used a circumscribed central composite design with 4 center points (OD600=0.45, ratio COI:SoS=1.67:1) and 3 replicates for a total of 48 runs. As controls, three non-infiltrated plants of each variety are grown in the same compartment and conditions as infiltrated plants.

Inoculum Preparation.

Two *Agrobacterium* cultures of AGL1 harboring the expression cassettes for the reporter gene tGFP (A91) as COI, and the suppressor of silencing HcPro (A120) as SoS are grown in "Animal free" LB Miller (10 g/L NaCl+10 g/L Vegetable Tryptone+5 g/L Yeast extract), supplemented with carbenicillin and kanamycin, to a final optical density ($OD_{600}$) of 2.0. Bacteria are harvested by centrifugation and resuspended in infiltration solution as described above. On the day of infiltration, the concentrated inocula of A91 and A120 are mixed together at three different ratios, 3:1, 1.67:1 and 1:3 and diluted in infiltration solution to a final OD600 of 0.85 each. The three inocula are equilibrated for 30 minutes to room temperature. The three inocula at OD600=0.85 are further sequentially diluted to OD600=0.45 and 0.05 in infiltration solution to asses the effects of using lower bacterial densities.

*Agrobacterium*-Mediated Infiltration and Biomass Harvesting.

Tobacco plants are infiltrated, incubated and harvested as described in Example 1. Extraction and quantification of tGFP are performed as described in Example 3. A standard curve is prepared by adding TurboGFP control protein (Evrogen) in a concentration range of 4000 to 125 ng/ml to a non-infiltrated extract diluted 1:50 final in extraction buffer.

Results.

In order to determine whether the *Agrobacterium* OD600 and the COI:SoS influence tGFP expression levels in *N. tabacum* varieties, a limited set of experiments is performed in which both factors are varied simultaneously. Tobacco plants of varieties Burley 21, PM132 and PM204 are infiltrated with A91 and A120 at OD600 of 0.85, 0.45 and 0.05 and at COI:SoS ratios of 3.00, 1.67 and 0.33. As expected from previous experiments, stress response to agroinfiltration such as leaf yellowing is observed at 6 DPI in the three tobacco varieties tested. Symptoms increased with bacterial density in the inoculum. Variety Burley 21 displayed more pronounced leaf yellowing even at the lowest density. Small necrotic lesions are visible on leaves of PM132 and PM204 infiltrated with inoculum at OD600=0.85, but are mostly limited to the basal part of the leaves. Stress symptoms are mainly due to inoculum density and no apparent effect of COI:SoS ratio is observed.

Figure 5:
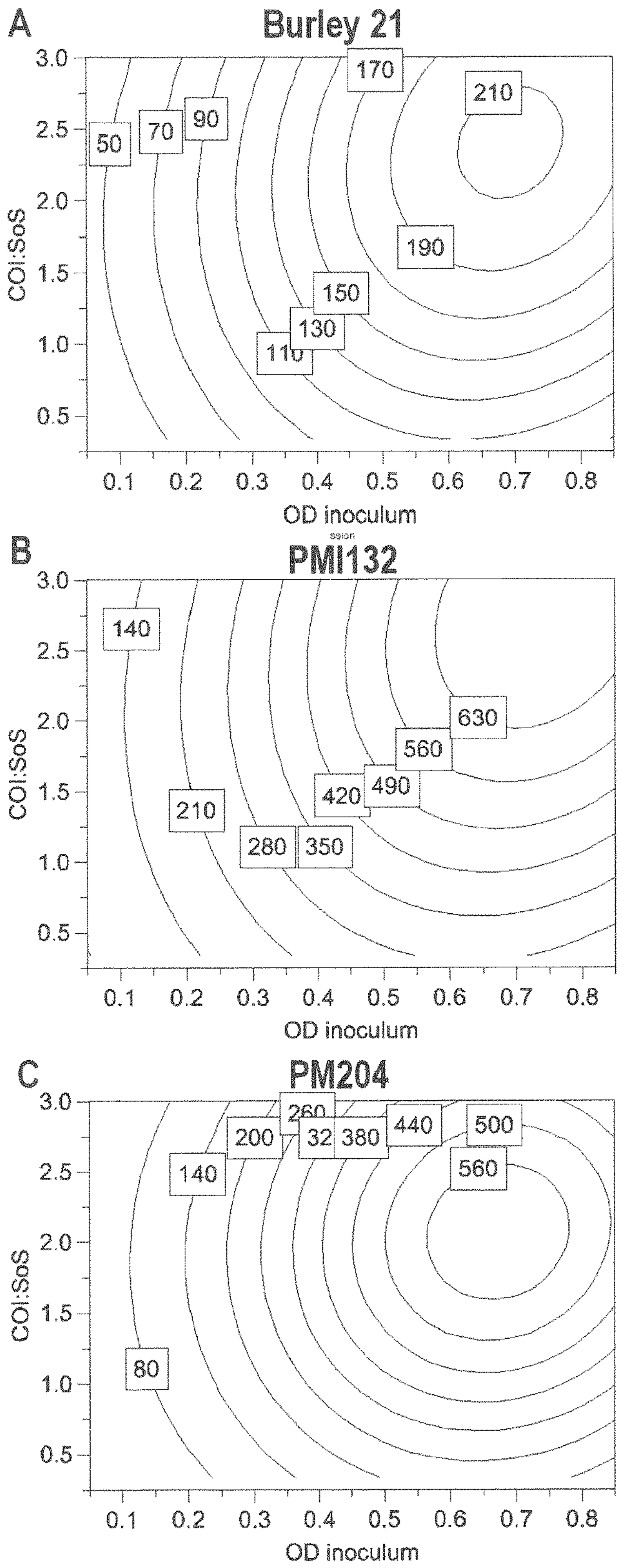

Next, a regression model is used, which is reliable for all three tobacco varieties, to interpolate tGFP expression inside the experimental space. Results are shown to be statistically relevant. Despite the symptoms observed, fluorimetric quantification of TurboGFP shows no negative correlation between plant stress response to increasing optical density and expression levels within the tested range. Leaves that display strong yellowing or even necrotic lesions at high OD still express higher tGFP levels than at low OD. The predicted response to inoculum density and COI:SoS ratio is similar for all three tobacco varieties and for all three maximum expression could be achieved at high *Agrobacterium* optical densities in the inoculum and high COI:SoS ratio (FIG. 5), confirming that both factors influence transient recombinant protein expression. Highest expression levels were observed for PM132 and PM204 (FIGS. 5 B and C).

Optimal parameters that are identified for each of the three varieties are: OD600=0.69; COI:SoS=2.40 for Burley 21, OD600=0.7428; COI:SoS=2.8058 for PM132 and OD600=0.6729; COI:SoS=2.0805 PM204. These parameters produced 215, 698 and 603 mg tGFP per kg frozen weight, respectively. However, the predicted optimum values for PM132 are almost outside the conditions chosen for this experiment (FIG. 5 B). Hence, a second experiment is performed using a final $OD_{600}$ of inoculum ranging from 0.6 to 1.2 and a COI:SoS ratio ranging from 2.0 to 4.5. In this case the model reproducibility is low, meaning there is a large pure error with high noise, nevertheless indicating the existence of a plateau around the optimum predicted in the first experiment.

Using an ANOVA with a general linear model procedure to compare all possible pairs of level means, the best model included the interactions and the test indicated that the level of tGFP expression in PM132 is significantly higher than those in Burley 21 and PM204.

Before optimization, the standard conditions used are $OD_{600}$=0.32 and a ratio of COI:SoS=1.00. A 2.0-2.5 times higher recombinant protein expression is achieved by increasing both the concentration of *Agrobacterium* cells in the inoculum and the ratio of construct of interest to suppressor of silencing.

Example 12: Improved Scalability of Inoculum Preparation for *Agrobacterium*-Mediated Transient Expression Plant Material.

Regular batches of *N. tabacum* plants Burley 21, PM132 and PM204 are grown at 35 plants/$m^2$ in the greenhouse compartment A in rockwool blocks with 20 hour light period, 26° C./20° C. day/night temperature and 70%/50% day/night relative humidity. Plants are tert-irrigated by sub-irrigation.

*Agrobacterium* Inoculum Preparation.

*Agrobacterium* cultures of strain AGL1 harboring the expression cassettes for either the reporter gene tGFP (A91) or the suppressor of silencing HcPro (A120) are grown in "Animal free" LB Miller (10 g/L NaCl+10 g/L Vegetable Tryptone+5 g/L Yeast extract), supplemented with carbenicillin and kanamycin, to a final $OD_{600}$ of >2.0 (if not otherwise stated). Depending on the conditions tested as described below, the bacteria are either harvested by centrifugation and resuspended in infiltration solution to $OD_{600}$>2.0, or the bacteria is kept in culture medium to generate concentrated inocula. On the day of infiltration, the concentrated inocula of A91 and A120 are mixed in a ratio of 1:1, diluted in infiltration solution to a final $OD_{600}$ of 0.32 and equilibrated for 30 minutes to room temperature.

*Agrobacterium*-Mediated Infiltration and Biomass Harvesting.

Tobacco plants are infiltrated, incubated and harvested as described in Example 1. Extraction and quantification of tGFP are performed as described in Example 3. A standard curve is prepared by adding TurboGFP control protein (Evrogen) in a concentration range of 4000 to 125 ng/ml to a non-infiltrated extract diluted 1:50 final in extraction buffer.

Determination of Total Soluble Protein Content.

Total soluble protein (TSP) content in the extracts is determined using the Coomassie-Plus Assay reagent (Pierce) by absorbance measurement on a microplate reader at 595 nm. Extracts are diluted 1:20 in ultrapure water and 10 μL are loaded in triplicate on a flat-bottom microplate.

Results.

Figure 6:
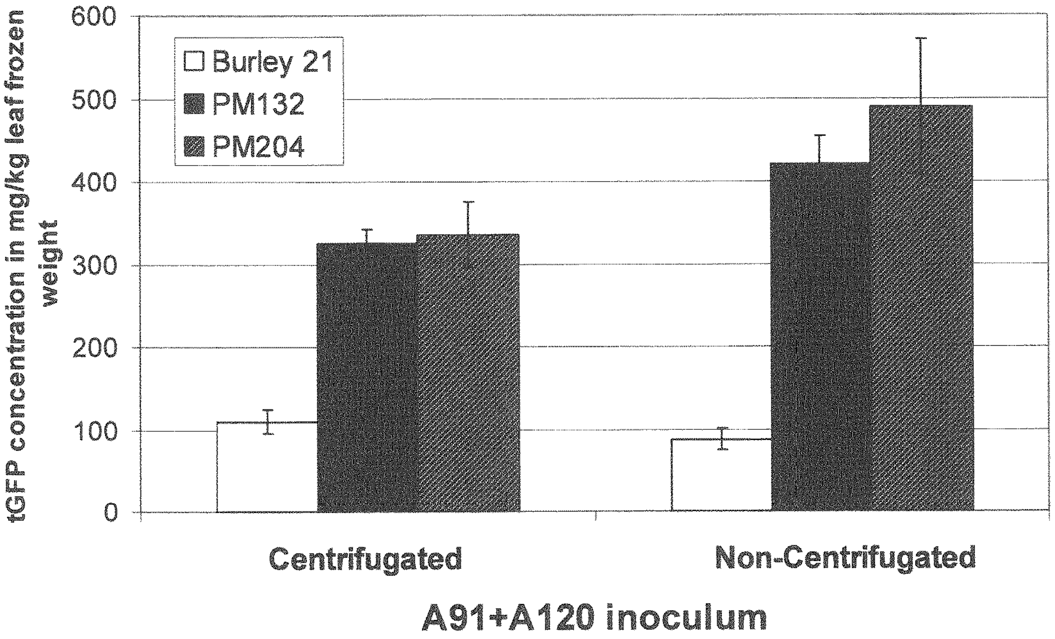

First, the possibility to prepare the final inoculum by diluting directly the *Agrobacterium* cultures in infiltration solution is investigated. As shown in FIG. 6, transient expression of tGFP in infiltrated tobacco Burley 21, PM132 and PM204 is not affected by the omission of the centrifugation/resuspension step. Moreover, plants of PM132 and PM204 infiltrated with an inoculum prepared directly from liquid cultures even led to significantly higher tGFP expression. Noticeably, expression levels in PM132 and PM204 are similar in both conditions and, thus, further experiments are performed using PM132 only.

After centrifugation and resuspension in the non-nutritive infiltration solution, inocula are usually stored for up to six days at 4° C. without any significant change in transfection efficiency and transient expression levels. Yet, omitting the centrifugation and resuspension steps raises the questions of storage conditions and storage time period. It is commonly assumed that *Agrobacterium* cells stored in LB medium are essentially left in a rich nutritive environment which could continue to promote bacterial growth and, as a result, lead to degradation of the culture. In a next step, storage stability of non-centrifugated inoculum is tested. Concentrated cultures of A91 (tGFP) and A120 (SoS) at $OD_{600}>2.0$ are stored for 5 to 0 days at 4° C. and diluted shortly before infiltration. An inoculum prepared from centrifugated cultures is used as positive control. Quantification of tGFP levels at 6 days post infiltration indicates that non-centrifugated inoculum is stable for 5 days at 4° C. without any change in expression efficiency as compared to inoculum stored for 1 day. Surprisingly, the use of inoculum prepared from fresh cultures resulted in lower expression of tGFP when it is compared to cultures that had been stored, suggesting that a short storage time at 4° C. is needed for the induction of *Agrobacterium* virulence and optimal transfection. These results also confirm that non-centrifugated inoculum is significantly and surprisingly more efficient than centrifugated inoculum in producing higher levels of recombinant protein.

Bacterial growth in liquid culture is characterized by the four successive phases: lag, log, stationary and death phases. During the log phase, bacteria are metabolically active and grow rapidly until they reach the stationary phase, where one or more nutrient in the medium is depleted and limits further growth. For successful transformation, bacteria are usually collected at early- to mid-log phase. Pilot experiments are carried out that aim at determining the growth curve of *Agrobacterium* strain AGL1. The data show that log phase occurred between $OD_{600}=0.3$ and $OD_{600}=3.8$-4.0, before entering stationary phase. In order to decrease the volume of culture needed in the preparation of the final inoculum, it is tested whether the use of cultures grown to late-log phase, i.e. at higher densities, could affect expression levels in tobacco. PM132 tobacco plants are infiltrated with inoculum prepared from cultures grown to either the usual $OD_{600}$ of 2.0 or to an $OD_{600}$ of 3.8 and directly diluted in infiltration solution. Remarkably, analysis of tGFP levels at 6 days post infiltration indicates that transient expression is not affected by using *Agrobacterium* cultures at late-log phase for inoculum preparation.

Together, these data demonstrate that scaling-up of inoculum preparation for transient *Agrobacterium*-mediated transformation of tobacco can be greatly facilitated, without affecting transient recombinant protein expression, by the use of cultures at high cell densities (up to $OD_{600}=3.8$) as well as by omitting the steps of centrifugation and resuspension when preparation the inoculum.

Example 13: Increased Expression of Recombinant Proteins by Incubation of Infiltrated Tobacco Plants in an Inverted Position This example describes a surprising discovery that incubation of infiltrated tobacco plant in an inverted position leads to increased expression of recombinant protein. The discovery is made while searching for a solution to the problem that infiltrated tobacco plants, especially when incubated at high densities in a greenhouse, tend to fall over because it cannot sustain the weight of the infiltrated leaves. The solution provided is by incubating the infiltrated plants upside down. Remarkably, incubation of the inverted infiltrated plants resulted in a significant increase in recombinant protein production compared to the tobacco plants incubated in the normal upright position.

Tobacco plants are vacuum-infiltrated with cells of *Agrobacterium* strain AGL1 harboring either the plasmids pC91 that comprises the tGFP expression cassette or pC71 that comprises the H5 expression cassette, as described above. All the tobacco plants are also co-infiltrated with pC120 that comprises an expressible HcPro suppressor of gene silencing as described above.

Plants and Infiltration.

Five to six week old plants of *N. tabacum* PM132 grown in rockwool and all at approximately 28 cm in height, are vacuum-infiltrated as described before with cells of *Agrobacterium* strain AGL1 harboring either the plasmids pC91 that comprises the tGFP expression cassette or pC71 that comprises the H5 expression cassette, as described above. All the tobacco plants are also co-infiltrated with pC120 that comprises an expressible HcPro suppressor of gene silencing as described above. Immediately after infiltration, infiltrated plants are incubated upside-down while illumination is provided from a position above the plants in a greenhouse. At 4 and 6 days after infiltration, 4 plants from each treatment group are harvested and three leaf disks per plant are used to measure tGFP expression. Leaf discs are frozen under liquid nitrogen and ground to a fine powder in a 2 ml eppendorf tube and extraction of tGFP is performed as described above. For the quantification of tGFP expression, 5 μL of each of the extracts is diluted to 200 μL and fluorescence is measured as described. Three replicates are made.

Results.

Figure 7:
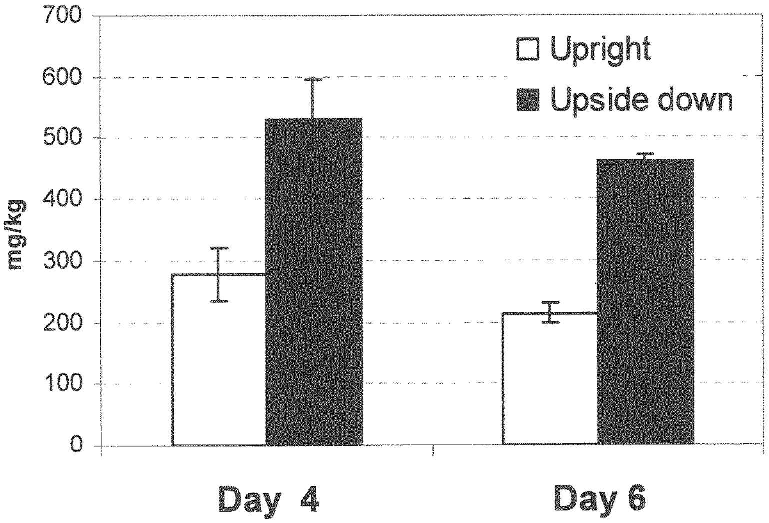
FIG. 7 shows tGFP expression 4 and 6 days post infiltration in mg/kg fresh weight leaf biomass in PM132 tobacco plants that are kept upright as normal or upside-down.

Plants did not show symptoms of water stress. A few days after hanging the plants upside-down, the stems of plants bend towards the light shone from a position higher above, forming a hook-like structure. From FIG. 7 it can be seen that tGFP expression and fluorescence is on average two times higher for plants incubated in an inverted position (that is, upside-down) as compared to the normally treated plants that are incubated in an upright position (FIG. 7).

Example 14: Enhanced Expression of tGFP and H5 by Increasing the Density of Growth of Tobacco Plants Prior to Infiltration This example describes the surprising effect of growing tobacco plants before infiltration at a high density on the expression of tGFP and recombinant H5. The experiment shows that two tobacco varieties PM132 and PM217 when grown at high density prior to infiltration, remarkably produced approximately 40% more tGFP and 70% more recombinant H5, on a weight-of-infiltrated biomass basis relative to plants grown at lower densities when incubated under normal upright conditions.

Plants and Infiltrations.

To study the effects of growing tobacco at different planting densities, *Nicotiana tabacum* PM132 and PM217 plants are grown at two densities: 25 and 100 plants per square meter. At day 46 after sowing, plants are vacuum infiltrated with *A. tumefaciens* strain AGL1 comprising either pC91 containing the tGFP expression cassette or pC71 containing the H5 expression cassette, and each together with *A. tumefaciens* strain AGL1 comprising pC120 containing the HcPro suppressor of gene silencing, as described before. The final $OD_{600}$ used in infiltration is 0.32. For plants grown at both densities, the average plant height, diameter of stomata, chlorophyll content, leaf thickness and water content are measured before infiltration. As can be seen from Table 3, plants grown at high densities are larger, had less chlorophyll and thinner leaves, but the diameter of stomata is the same. For PM132, the water content is the same for plants grown at low or high density but for PM217, the water content is much lower when grown at low density. Following infiltration, half of the plants are incubated upright or inverted (upside-down). Measurements are performed on a total of 9 (nine) plants per treatment spread over three replicates of each 3 plants.

Results.

Leaves are harvested 5 days post infiltration, an extract is prepared and analysis of tGFP expression are performed, as described above. The extract is diluted 1:1 in GFP buffer and 5 μL is mixed with 200 μL of GFP buffer for fluorescence quantification. The expression of recombinant H5 is quantified by ELISA. Results are summarized in Table 4.

As can be seen from Table 4, the expression of tGFP in mg/kg fresh weight leaf biomass for both varieties when incubated in normal upright position, is on average 41% higher for plants grown at high density prior to infiltration when compared to plants grown at low density. Similar results are obtained for H5 which showed an average increase of expression when grown at high density between 21-40% when compared to plants grown at low density and incubated in normal upright position post infiltration. To study the effects of inverted incubation on expression of tGFP and H5, half of the infiltrated plants are incubated in an inverted position after infiltration. As can be seen from Table 4, there is a significant increase of expression of both tGFP and H5 for plants incubated in an inverted position and grown at low density but much less increase of expression for plants grown at high density prior to infiltration. For PM132 plants grown at low density in an inverted position, it results in an increase of 40% of tGFP and 71% of H5. For plants grown at high density prior to infiltration, the increase is only 3% for tGFP and 7% for H5, compared to plants incubated in a normal upright position. Total soluble protein (TSP) is established and the expression of tGFP and H5 is estimated relative to TSP. The expression of tGFP and H5 is always higher for plants grown at high density and incubated in an inverted position. In an upright position, plants grown at low density had an increase of tGFP expression of approximately 10.5%. For plants grown at high density, the increase is approximately 13.6%. For H5, the increase in yield for plants incubated in upright position and grown at low density prior to infiltration is 0.25%, whereas the increase in yield for plants grown at high density is 0.37%. For both tGFP and H5, incubation in an inverted position resulted in an increase of expression (as measured in percentage of TSP). For plants grown at low density, incubation at an inverted position resulted in an increase of biomass by 40-60%. For plants grown at high density, incubation in an inverted position resulted in an increase of 20%. For tGFP the highest protein yield is 16.2% and is obtained when the plants are grown at high density before infiltration and are incubated in an inverted position. This represented an increase of 54% in protein yield in terms of % TSP compared to plants grown at low density and incubated in normal upright position (10.5% of TSP).

To evaluate whether reduced light reaching the upper surface of the leaves of plants grown at high density and incubated in an inverted position might have caused the increased expression, plants infiltrated with the tGFP expression vector are incubated under total darkness. Remarkably, the data indicate that incubation in total darkness is detrimental for tGFP expression. As can be seen from FIG. 18, plants incubated in the dark produced on average 45% less tGFP compared to plants grown in the light.

Additional experiments were performed to investigate the effect of three higher growth densities, 122, 529 and 961 plants per $m^2$ on biomass production in PM132. The experiments were carried out in a complete randomized block design with five replications. The growth substrate was rock wool blocks that were 30 cm×30 cm×7 cm and a wooden dibble was fabricated according to the plant densities. The dibbles were pressed into the blocks to create small divots approximately 5 mm deep. The seedlings were transplanted into the blocks by hand. The entire area of 30 cm×30 cm of the block contained plants spaced to achieve the desired density, but at the time of infiltration, only plants located in the middle 15 cm×15 cm area were infiltrated. This practice allowed the formation of borders around the middle area to eliminate any border effects. Prior to infiltration, the border plants were clipped and discarded. Infiltrations were performed on plants at two developmental stages, plant height at 25 cm and 35 cm. The infiltrated plants were incubated in the greenhouse for 5 days in normal or inverted position.

An inoculum was prepared as described above except that the ratio of AGL1 culture carrying the TurboGFP expression cassette to AGL1 culture carrying HcPro was 3:1 and the final OD600 was 0.8. The plants were infiltrated under 50 mbar pressure which was reached within 1 minute 45 seconds and released quickly in 1.5 seconds.

Five days after infiltration, total biomass, leaf and stem fresh weight, leaf thickness and other biomass measurements were made. Whole plant materials including stems were quickly frozen in dry ice and stored at −80 C.

Characteristics of biomass of tobacco plants planted at 122, 529 and 961 plants per $m^2$ indicated that at these ranges of plant density, no significant differences in average plant height, % leaf biomass and leaf thickness were observed. However, there is a decrease in the weight of individual plants with increasing density even the % leaf biomass remained relatively constant. An increase in biomass per unit of growth area was observed at both time points at the density of 529 plants/$m^2$. A maximum yield of approximately 5 kg leaf fresh weight per $m^2$ or 10 kg total biomass per $m^2$ was obtained when plants were infiltrated when their height was at 35 to 45 cm and planted at 529 plants/per $m^2$. The yield of TurboGFP per unit area were obtained by multiplying the TurboGFP concentration in the biomass by the calculated yields of biomass per square meter. The highest yield of TurboGFP per unit area was obtained at a density of 529 plants/per $m^2$. Further increase in planting density to 961 plants per $m^2$ had a negative impact on yield of recombinant protein.

Example 15: Enhanced Recombinant Protein Expression by Incubation Under Short Day Conditions Post Infiltration This example describes the result of an experiment in which tobacco plants are incubated under short (8 h light per day) day and long (20 h light per day) day conditions post infiltration. The experiment shows that for plants incubated in normal upright position as well as upside-down, the expression of tGFP is greatly enhanced when plants are kept under short day conditions post infiltration.

Plants and Infiltrations.

*N. tabacum* PM132 plants are grown at a density of 75 plants per sq m. 42 day old plants are infiltrated with a mix of two *A. tumefaciens* AGL1 strains containing pC91 (tGFP binary expression vector) and pC120 (HcPro suppressor of gene silencing binary expression vector) in a 1:1 ratio and final $OD_{600}$=0.32. Plants are on average 43.4 cm tall and had an average stomatal conductance of 559.6 $\mu$molm$^{-2}$ s$^{-1}$ indicating adequate stomatal opening for inoculum uptake (Table 5). Following infiltration, plants are incubated under two different light cycles: 8 h light per day or 20 h light per day. Half of the plants under each light treatment are placed in normal upright position and the other half in an inverted position. In total, 4 treatments are performed. Plants are harvested at 0, 3, 5, 7 and 9 days post infiltration. For each measurement, 4 plants are harvested per treatment and 3 leaf disks per plant are taken for tGFP expression analysis. For tGFP quantification, leaf disks are ground in 1 ml of GFP buffer and 5 $\mu$L of the extract is mixed with 200 $\mu$L of GFP buffer for fluorescence measurement as described before.

Results.

Figure 8:
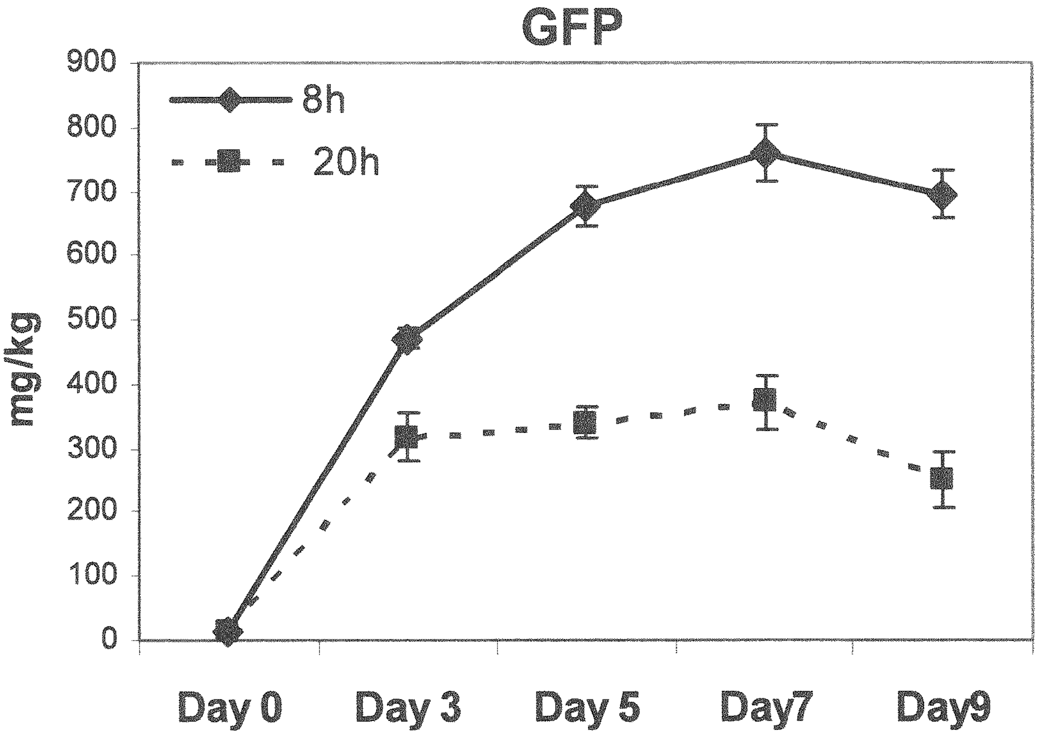
FIG. 8 shows time-course of tGFP expression in mg tGFP/kg fresh leaf biomass in tobacco plants incubated under low 8 h light compared to long 20 h light, post infiltration.

Quantification of tGFP expression (mg tGFP/kg fresh weight biomass) under two light regimes post infiltration revealed significant light effects on recombinant protein production (FIG. 8). Regardless of the position of the plant (upright or inverted), plants incubated under short day conditions produced significantly higher amounts of tGFP as can be seen from FIG. 8. At day 7 post infiltration, in plants incubated at 8 h light, the expression of tGFP is twice the amount compared to plants incubated under 20 h light post infiltration.

At day 7 post infiltration, tGFP expression in upright plants under 8 h is 104% higher than tGFP expression in similar plants incubated under 20 h light regime. For plants incubated upside-down, the trend is similar with plants under 8 h light producing 50% more tGFP than plants incubated under 20 h light regime. Incubation in an inverted position also enhanced tGFP expression in plants grown under the two light regimes (8 hours of light and 20 hours of light). Enhanced expression is more pronounced at 20 hour light compared to 8 hour light treatment and could be increased from 371.2 mg tGFP/kg fresh weight biomass for plants grown in normal upright position and 20 h light, to 857.5 mg tGFP/kg fresh weight biomass for plants incubated in upside-down position at 8 h light, which represents a 130% increase in recombinant protein yield.

Example 16: Optimized Infiltration of Plants by *Agrobacterium*

This example describes the result of an experiment in which the stomatal aperture of tobacco plants prior to infiltration is investigated. The results indicate that prior to infiltration, tobacco plants should be exposed to light such that the stomatal conductance is at a range that is characteristics of the tobacco plant grown under well-lit conditions. Tobacco plants were grown at a density of about 9 plants/$m^2$ in order to avoid any competition for light or space. Experimental units were monitored daily to assure a uniform and stable growing environment. Irrigation solution had an electric conductivity value (EC) of 2.4 and a nitrogen content equal to 206 mg/L in order to assure adequate nutrient supply. Watering regime was adjusted according to the needs of the plants in order to avoid any stress caused by over or under watering.

Two varieties, PM132 and PM15, of *N. tabacum* plants at 39 days old were transformed with *Agrobacterium* (Agl1) containing an expression cassette encoding TurboGFP (pC91) in combination with *Agrobacterium* (Agl1) expressing Hc-Pro as described above. Expression of the GFP was driven by a minimal CaMV35S plus promoter and a 5'UTR of cowpea mosaic virus (HT-CPMV) while expression of HC-Pro was driven by a double CaMV35S promoter. Bacterial concentrations in the infiltration mixture were kept at 0.16 for a single construct treatment (GFP or Suppresor of Silencing (SoS)) and 0.32 for the two-construct treatments (GFP+SoS). Plants were infiltrated at 50 mbar for 1 min following standard infiltration protocols.

Before infiltrations half of the plants were placed in a dark compartment while the other half were placed inside a compartment with natural light supplemented with artificial light. During this time, stomatal conductance was recorded using a steady state porometer SC-1 (Decagon Devices, USA). Measurements were taken in three fully expanded consecutive leaves at positions 4, 5 and 6 (where 1 is the first leaf at the apical shoot which is perpendicular to the stem). Water content of the growing substrate (Rockwool) was measured with WET-2 sensor (Delta-T devices, USA).

Stomatal conductance differences were highly significant between light and dark treatments for both tobacco varieties. Plants kept in the light exhibited conductance values between 4 and 8 times higher than dark-kept plants: PM132 plants in the light showed an average value of 260.6 $\mu$mol m$^{-2}$ s$^{-1}$ while in dark of 70.4 $\mu$mol m$^{-2}$ s$^{-1}$. Likewise, PM15 plants in light showed an average value of 440.1 $\mu$mol m$^{-2}$ s$^{-1}$ while in dark of 53.6 $\mu$mol m$^{-2}$ s$^{-1}$. These results indicate that stomatal aperture in tobacco can be regulated by the quantity of light given to the plants: while keeping plants under well-lit conditions promotes stomatal opening, decreasing the amount of light significantly reduces stomatal aperture (lower stomatal conductance). It is also worth noting that differences in stomatal conductance between tobacco varieties are also observed, with PM15 exhibiting 1.7 times higher conductance in light than PM132. Accordingly, it is preferred that prior to infiltration, the stomatal conductance of PM132 is in a range that is greater than about 70 $\mu$mol m$^{-2}$ s$^{-1}$, greater than 100 $\mu$mol m$^{-2}$ s$^{-1}$, greater than 150 $\mu$mol m$^{-2}$ s$^{-1}$, greater than 200 $\mu$mol m$^{-2}$ s$^{-1}$, greater than 250 $\mu$mol m$^{-2}$ s$^{-1}$, or greater than 300 $\mu$mol m$^{-2}$ s$^{-1}$.

Infiltrated leaves were frozen and ground to powder in dry ice. GFP was extracted and fluorescence measured. For both tobacco varieties, GFP content was significantly higher for light-incubated plants than dark-incubated plants. In PM132 light-incubated plants showed 40% more fluorescence than dark-incubated plants. For PM15 light-incubated plants showed 200% more fluorescence than dark-incubated plants.

The data showed that stomata in tobacco rapidly respond to changes in light conditions. Plants placed under low light showed between 4 and 8 times less stomatal conductance than well-lit plants. Stomatal closure caused by low light negatively impacts vacuum infiltration efficiency and hence reduces GFP expression in tobacco. Plants incubated in the dark exhibited large areas of non-infiltrated leaf tissue and a reduction of GFP expression of more than 50%, compared to plants grown under normal light conditions.

Example 17: Infiltration of Tobacco Plants with Enzymes

This example describes the result of an experiment in which tobacco plants previously infiltrated with *Agrobacterium* are treated with enzymes that degrade or digest plant cell wall to aid the extraction and isolation of the heterologous protein. The tobacco plants have been infiltrated by the gene construct pC71 comprising a coding sequence for H5 as described above, and incubated under greenhouse conditions that enable the transient expression and production of H5. An aqueous mixture of enzymes was prepared: 0.05% Macerozyme, 0.4% cellulose, 0.066% Driselase, 0.6M mannitol, 0.7 g/l 2-(N-morpholino)ethanesulfonic acid (MES) at pH 5.6. In one sample of the enzyme mixture, glycine is added to a concentration of 15 g/l.

The enzyme mixture was injected into the underside of tobacco leaves by syringe at a volume of 0.3 ml per gram of leaf. For comparison, thin cut strips of leaves were submerged and incubated in the same mixture. The leaves were incubated for 12 hours before harvesting and extraction of H5. Western blotting with anti-H5 antibody showed that similar amounts of H5 was obtained with enzyme mixtures with or without glycine. The efficiency of extraction by syringe infiltration and by submerging cut leaves was also similar. The results show that infiltration of tobacco leaves with cell wall-digestive enzymes can be used to assist the extraction of heterologous protein from tobacco plants.

While the invention has been described in detail and foregoing description, such description are to be considered illustrative or exemplary and not restrictive. It will be understood that changes and modifications may be made by those of ordinary skill within the scope and spirit of the following claims. Various publications and patents are cited throughout the specification. The disclosures of each of these publications and patents are incorporated by reference in its entirety.

Tables

TABLE 1

| Species | Variety |
|---|---|
| *N. tabacum* | AA 37-1 |
| *N. tabacum* | B 13P |
| *N. tabacum* | Xanthi (Mitchell-Mor) |
| *N. tabacum* | Bel-W3 |
| *N. tabacum* | Samsun Holmes NN |
| *N. tabacum* | F4 from the cross BU21 × Hoja Parado, line 97 |
| *N. tabacum* | Burley 21 |
| *N. tabacum* | PM016 |
| *N. tabacum* | PM021 |

TABLE 1-continued

| Species | Variety |
|---|---|
| *N. tabacum* | K 149 |
| *N. tabacum* | K 326 |
| *N. tabacum* | K 346 |
| *N. tabacum* | K 358 |
| *N. tabacum* | K 394 |
| *N. tabacum* | K 399 |
| *N. tabacum* | K 730 |
| *N. tabacum* | KY 10 |
| *N. tabacum* | KY 14 |
| *N. tabacum* | KY 160 |
| *N. tabacum* | KY 17 |
| *N. tabacum* | KY 8959 |
| *N. tabacum* | KY 9 |
| *N. tabacum* | KY 907 |
| *N. tabacum* | MD 609 |
| *N. tabacum* | McNair 373 (MN 373) |
| *N. tabacum* | NC 2000 |
| *N. tabacum* | PG 01 |
| *N. tabacum* | PG 04 |
| *N. tabacum* | PO1 |
| *N. tabacum* | PO2 |
| *N. tabacum* | PO3 |
| *N. tabacum* | RG 11 |
| *N. tabacum* | RG 17 |
| *N. tabacum* | RG 8 |
| *N. tabacum* | Speight G-28 |
| *N. tabacum* | TN 86 |
| *N. tabacum* | TN 90 |
| *N. tabacum* | VA 509 |
| *N. tabacum* | AS44 |
| *N. tabacum* | Banket A1 |
| *N. tabacum* | Basma Drama B84/31 |
| *N. tabacum* | Basma I Zichna ZP4/B |
| *N. tabacum* | Basma Xanthi BX 2A |
| *N. tabacum* | Batek |
| *N. tabacum* | Besuki Jember |
| *N. tabacum* | C104 |
| *N. tabacum* | Coker 319 |
| *N. tabacum* | Coker 347 |
| *N. tabacum* | Criollo Misionero |
| *N. tabacum* | PM092 |
| *N. tabacum* | Delcrest |
| *N. tabacum* | Djebel 81 |
| *N. tabacum* | DVH 405 |
| *N. tabacum* | Galpão Comum |
| *N. tabacum* | HB04P |
| *N. tabacum* | HICKS |
| *N. tabacum* | Kabakulak Elassona |
| *N. tabacum* | PM102 |
| *N. tabacum* | Kutsaga 51E |
| *N. tabacum* | Kutsaga E1 |
| *N. tabacum* | KY 14xL8 |
| *N. tabacum* | KY 171 |
| *N. tabacum* | LA BU 21 |
| *N. tabacum* | McNair 944 (MN 944) |
| *N. tabacum* | NC 2326 |
| *N. tabacum* | NC 71 |
| *N. tabacum* | NC 297 |
| *N. tabacum* | NC 3 |
| *N. tabacum* | PVH 03 |
| *N. tabacum* | PVH 09 |
| *N. tabacum* | PVH 19 |
| *N. tabacum* | PVH 2110 |
| *N. tabacum* | Red Russian |
| *N. tabacum* | Samsun |
| *N. tabacum* | Saplak |
| *N. tabacum* | Simmaba |
| *N. tabacum* | Talgar 28 |
| *N. tabacum* | PM132 |
| *N. tabacum* | Wisliça |
| *N. tabacum* | Yayaldag |
| *N. tabacum* | NC 4 |
| *N. tabacum* | TR Madole |
| *N. tabacum* | Prilep HC-72 |
| *N. tabacum* | Prilep P23 |
| *N. tabacum* | Prilep PB 156/1 |
| *N. tabacum* | Prilep P12-2/1 |
| *N. tabacum* | Yaka JK-48 |

TABLE 1-continued

| Species | Variety |
|---|---|
| *N. tabacum* | Yaka JB 125/3 |
| *N. tabacum* | TI-1068 |
| *N. tabacum* | KDH-960 |
| *N. tabacum* | TI-1070 |
| *N. tabacum* | TW136 |
| *N. tabacum* | PM204 |
| *N. tabacum* | PM205 |
| *N. tabacum* | Basma |
| *N. tabacum* | TKF 4028 |
| *N. tabacum* | L8 |
| *N. tabacum* | TKF 2002 |
| *N. tabacum* | TN90 (GR141) |
| *N. tabacum* | Basma xanthi |
| *N. tabacum* | GR149 |
| *N. tabacum* | GR153 |
| *N. tabacum* | Petite Havana |
| *N. tabacum* | PM215 |
| *N. tabacum* | PM216 |
| *N. tabacum* | PM217 |
| *N. tabacum* | Denizli |
| *N. tabacum* | Izmir |
| *N. tabacum* | Coker 371 Gold |
| *N. tabacum* | Dac Mata Fina |
| *N. tabacum* | BY-64 |
| *N. tabacum* | Kasturi Mawar |
| *N. tabacum* | Karabalgar |
| *N. tabacum* | Xanthi NN |
| *N. tabacum* | Samsun NN |
| *N. tabacum* | Turkish Samsun |

TABLE 2

| Accession | Expression in 3 plants | Phenotype of infiltrated leaves | Phenotype of control plant |
|---|---|---|---|
| PM092 | +++, +++, +++ | green to light green | green |
| PO2 | +++, +++, +++ | green | green |
| PM016 | +++, +++, +++ | yellowish | light green |
| AS44 | +++, +++, +++ | light green - yellowish | green |
| RG17 | +++, +++, +++ | yellowish | green |
| RG8 | +++, +++, +++ | light green - yellowish | green |

TABLE 2-continued

| Accession | Expression in 3 plants | Phenotype of infiltrated leaves | Phenotype of control plant |
|---|---|---|---|
| BY-64 | +++, +++, +++ | yellowish | light green |
| Coker 371 Gold | ++/+++, ++, ++/+++ | light green - yellowish | green |
| HB04P | +++, +++, +++ | yellowish | green |
| Basma Xanthi BX 2A | +++, +++, +++ | light green - yellowish | green |
| Coker 319 | +++, +++, +++ | light green - yellowish | green |
| Hicks | +++, +++, +++ | tight green - yellowish | green |
| Dac Mata Fina | +++, +++, +++ | green to light green | green |
| McNair 944 (MN 944) | +++, +++, +++ | light green | green |
| Burley 21 | +++, ++, +++ | yellowish | light green |
| K149 | +++, ++, +++ | light green - yellowish | light green |
| Yaka JB 125/3 | +++, ++, +++ | green | green |
| PM102 | +++, ++, +++ | green to yellowish | green |
| NC 297 | ++/+++, ++/+++, ++/+++ | light green - yellowish | green |
| PM021 | ++/+++, ++, ++/+++ | light green - yellowish | green |
| PO2 | ++/+++, ++, ++/+++ | green | green |
| Kasturi Mawar | +++, ++, +++ | green to yellowish | green |
| Wislica | ++/+++, ++/+++, ++ | light green | green |
| Simmaba | ++, ++, ++/+++ | light green | green |
| PM132 | ++, ++, ++ | light green | green |
| AA37-1 | ++, ++, ++ | yellowish | green, bottom leaves yellow |
| Turkish Samsun | ++, ++, ++ | light green | green |
| B13P | ++, ++, ++ | yellowish | green |
| F4 from the cross BU21 × Hoja Parado, line 97 | ++, ++, ++ | yellowish | light green |
| PM204 | ++, ++, ++ | green to light green | green |
| PO1 | ++, ++, ++ | light green | green |
| Samsun NN | ++, ++, ++ | green to light green | green |

TABLE 3

| Biomass characteristics | | | | | | | | | | |
|---|---|---|---|---|---|---|---|---|---|---|
| | Plant height (cm) | | Stomatal conductance (μmol m − 2 s − 1) | | Chlorophyl content L4 | | Leaf thickness (mm) | | Water content (%) | |
| Density | Mean | SE | Mean | SE | Mean | SE | Mean | SE | Mean | SE |
| PM132 | | | | | | | | | | |
| 25 | 32.9 | 0.6 | 956.6 | 78.1 | 28.63 | 1.4 | 0.290 | 0.005 | 62.3 | 1.4 |
| 100 | 51.5 | 0.9 | 985.1 | 204.3 | 18.32 | 1.8 | 0.230 | 0.005 | 61.69 | 0.7 |
| PM217 | | | | | | | | | | |
| 25 | 40.1 | 1.0 | 817.7 | 123.1 | 41.53 | 1.8 | 0.249 | 0.006 | 36.07 | 1.3 |
| 100 | 50.7 | 1.3 | 824.7 | 159.0 | 28.19 | 1.3 | 0.211 | 0.005 | 60.69 | 0.6 |

TABLE 4

| GFP and H5 concentration mg/kg of leaves fresh weight | | | | | | | | | |
|---|---|---|---|---|---|---|---|---|---|
| | Upright | | Upside-down | | | Upright | | Upside-down | |
| GFP | Mean | SE | Mean | SE | H5 | Mean | SE | Mean | SE |
| PM132 | | | | | PM132 | | | | |
| 25 | 343.4 | 15.5 | 482.4 | 19.0 | 25 | 19.5 | 5.4 | 33.4 | 2.4 |
| 100 | 483.0 | 63.9 | 499.8 | 60.1 | 100 | 27.1 | 2.8 | 29.0 | 3.8 |
| PM217 | | | | | PM217 | | | | |
| 25 | 314.8 | 29.3 | 441.8 | 10.7 | 25 | 20.5 | 3.4 | 28.9 | 1.2 |
| 100 | 449.4 | 36.5 | 439.7 | 25.7 | 100 | 24.8 | 1.0 | 29.9 | 1.2 |

TABLE 5

| Plant characteristics | | | | | | | | | | |
|---|---|---|---|---|---|---|---|---|---|---|
| | Height (cm) | | Stomatal conductance (μmol m − 2 s − 1) | | Chlorophyl content L4 | | Leaf thickness (mm) | | Water content (%) | |
| | Mean | SE | Mean | SE | Mean | SE | Mean | SE | Mean | SE |
| 8 & 20 h | 43.4 | 1.52 | 559.6 | 92.87 | 27.37 | 1.71 | 0.253 | 0.005 | 60.3 | 1.16 |
| 8, 14 & 20 h | 41.5 | 1.6 | 250.1 | 53.0 | 16.7 | 0.9 | 0.243 | 0.010 | 67.0 | 0.5 |

DEPOSIT

The following seed samples were deposited with NCIMB, Ferguson Building, Craibstone Estate, Bucksburn, Aberdeen AB21 9YA, Scotland, UK on Jan. 6, 2011 under the provisions of the Budapest Treaty in the name of Philip Morris Products S.A:

Until the grant of a patent or for 20 years from the date of filing if the application is refused or withdrawn, a sample shall only be issued to an independent expert nominated by the requester (Rule 13bis.6 PCT).

| PM seed line designation | Deposition date | Accession No |
|---|---|---|
| PM016 | 6 Jan. 2011 | NCIMB 41798 |
| PM021 | 6 Jan. 2011 | NCIMB 41799 |

-continued

| PM seed line designation | Deposition date | Accession No |
|---|---|---|
| PM092 | 6 Jan. 2011 | NCIMB 41800 |
| PM102 | 6 Jan. 2011 | NCIMB 41801 |
| PM132 | 6 Jan. 2011 | NCIMB 41802 |
| PM204 | 6 Jan. 2011 | NCIMB 41803 |
| PM205 | 6 Jan. 2011 | NCIMB 41804 |
| PM215 | 6 Jan. 2011 | NCIMB 41805 |
| PM216 | 6 Jan. 2011 | NCIMB 41806 |
| PM217 | 6 Jan. 2011 | NCIMB 41807 |

The invention claimed is:

1. A transient expression based method for producing large quantities of a heterologous polypeptide in *Nicotiana tabacum* comprising the steps of:

(i) infiltrating a whole plant of *Nicotiana tabacum* line PM132, seeds of which were deposited under accession number NCIMB 41802 strain with a suspension of the strain of *Agrobacterium tumefaciens* strain AGL1 or of *Agrobacterium tumefaciens* strain EHA105 at an $OD_{600}$ of between 0.1 and 4.0, the strain comprising an expressible nucleotide sequence encoding the heterologous polypeptide; and (ii) incubating the infiltrated plant for a period of between 5 days and 10 days under conditions that allow expression of the expressible nucleotide sequence in the infiltrated plant and accumulation of the heterologous polypeptide;

such that approximately 700 mg TurboGFP/kg (tGFP/kg) frozen leaf weight can be obtained in *Nicotiana tabacum* plants of line PM 132 when using an assay system comprising *Agrobacterium* strains AGL1 and EHA105, respectively, harboring a gene construct comprising the tGFP gene cloned under the control of the cauliflower mosaic virus 35S promoter and HT-CPMV sequence and the NOS terminator sequence, under the proviso that *Agrobacterium* strain AGL1 and EHA105, respectively, does not contain a virus expression vector.

2. The method according to claim 1, wherein the expressible nucleotide sequence encoding the polypeptide is cloned in a minimally-sized binary vector which has a polynucleotide sequence of SEQ ID NO: 1.

3. The method of claim 1, wherein the suspension of *Agrobacterium* cells used in step (i) for infiltrating *Nicotiana tabacum* line PM132, seeds of which were deposited under accession number NCIMB 41802, has a cell density ($OD_{600}$) in the range of 0.6 to 0.9.

4. The method of claim 1, wherein a suppressor of gene silencing is transiently expressed in the *N. tabacum* plant when the nucleotide sequence encoding the heterologous polypeptide is expressed.

5. The method of claim 4, wherein the nucleotide sequence encoding a suppressor of gene silencing is located on a first binary vector and the nucleotide sequence encoding the heterologous polypeptide is located on a second binary vector.

6. The method of claim 1, wherein a helper-component proteinase (HcPro) of a potyvirus is transiently expressed in the *N. tabacum* plant when the nucleotide sequence encoding the heterologous polypeptide is expressed.

7. The method of claim 6, wherein a helper-component proteinase (HcPro) of a potyvirus is transiently expressed in the *N. tabacum* plant using a second binary vector that is separate from the first binary vector comprising the nucleotide sequence encoding the heterologous polypeptide.

8. The method of claim 6, wherein the helper-component proteinase (HcPro) of a potyvirus is encoded by a nucleic acid molecule comprising the nucleotide sequence set forth in SEQ ID NO: 5.

9. The method claim 4, wherein the first binary vector is provided in a first *Agrobacterium* strain and the second vector is provided in a second *Agrobacterium* strain and wherein in step (i), the ratio of cells of the first *Agrobacterium* strain comprising the first binary vector comprising the nucleotide sequence encoding a heterologous protein, to cells of the second *Agrobacterium* strain comprising the second binary vector, is in a range from 3:1 to 1.6:1.

10. The method of claim 1, wherein seeds of *Nicotiana tabacum* line PM132 were deposited under accession number NCIMB 41802 and wherein the seed depositary is NCIMB in Aberdeen, Scotland.

11. The method of claim 1, wherein the heterologous polypeptide is an influenza haemagglutinin or an immunogenic fragment thereof.

12. The method of claim 1, wherein the plants are exposed to light prior to infiltration, such that the stomatal conductance is in a range of between 70 $\mu mol\ m^{-2}\ s^{-1}$ and 600 $\mu mol\ m^{-2}\ s^{-1}$.

13. The method of claim 1, wherein step (ii) comprises incubating the plant under daylight conditions for seven to nine hours per day.

14. The method of claim 1, wherein step (ii) comprises incubating the infiltrated plant in an inverted position.

15. The method of claim 1, further comprising (a) prior to infiltration, growing whole tobacco plant of *N. tabacum* line PM132, seeds of which were deposited under accession number NCIMB 41802, at a density of at least 100 plants per square meter, or (b) after infiltration, incubating the infiltrated whole plants at a density of at least 100 plants per square meter, or (c) prior to infiltration, growing whole tobacco plant of *N. tabacum* line PM132, seeds of which were deposited under accession number NCIMB 41802, at a density of at least 100 plants per square meter, and after infiltration, incubating the infiltrated whole plants at a density of at least 100 plants per square meter.

16. The method of claim 15, wherein the plants are grown in a density of between 200 and 600 plants per square meter.

17. The method of claim 1, further comprising after step (ii), a step (iii) of infiltrating the whole *Agrobacterium*-infiltrated plant with one or more enzymes that degrade plant cell wall.

18. The method of claim 1, wherein step (i) comprises infiltrating the whole plant by one or more pressure cycle(s) wherein at least one of the pressure cycle(s) comprises an increase in pressure relative to atmospheric pressure.

19. The method of claim 1, wherein the expressible nucleotide sequence encoding the polypeptide is cloned in a binary vector comprising a T-DNA region that comprises one or two or more copies of a FLt promoter or a functional fragment thereof, wherein the FLt promoter is that of MMV, FMV or PCISV.

20. The transient expression-based method of claim 1, wherein the gene construct comprises a TurboGFP gene cloned under control of a cauliflower mosaic virus 35S promoter and HT-CPMV sequence and a NOS terminator sequence.

* * * * *